United States Patent
Gillig et al.

(10) Patent No.: US 7,132,456 B2
(45) Date of Patent: Nov. 7, 2006

(54) MCH RECEPTOR ANTAGONISTS

(75) Inventors: James Ronald Gillig, Indianapolis, IN (US); Lawrence Joseph Heinz, Pittsboro, IN (US); Michael Dean Kinnick, Indianapolis, IN (US); Yen-Shi Lai, Chapel Hill, NC (US); John Michael Morin, Brownsburg, IN (US); Nancy June Snyder, Lizton, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/536,053

(22) PCT Filed: Dec. 3, 2003

(86) PCT No.: PCT/US03/37071

§ 371 (c)(1),
(2), (4) Date: May 24, 2005

(87) PCT Pub. No.: WO2004/052848

PCT Pub. Date: Jun. 24, 2004

(65) Prior Publication Data

US 2006/0052449 A1    Mar. 9, 2006

Related U.S. Application Data

(60) Provisional application No. 60/432,701, filed on Dec. 11, 2002.

(51) Int. Cl.
*A61K 31/165*   (2006.01)
*C07C 55/06*    (2006.01)
*C07C 323/42*   (2006.01)

(52) U.S. Cl. ................. 514/618; 562/597; 564/162
(58) Field of Classification Search ............. 514/618; 562/597; 564/162
See application file for complete search history.

(56) References Cited

U.S. PATENT DOCUMENTS 3,535,330 A    10/1970    Griot
3,928,449 A    12/1975    Griot
4,206,072 A    6/1980     Meyer et al.

FOREIGN PATENT DOCUMENTS

DE    27 52 361           6/1979
WO    WO 01/21577         3/2001
WO    WO 200121577 A2 *   3/2001

OTHER PUBLICATIONS

Kutzki, et al., "Development of a potent Bcl-xL antagonist based on alpha-helix mimicry," Journal of the American Chemical Society, XP002277113, vol. 124, No. 40, pp. 11838-11839 (2002).
Shimizu, et al., "Synthesis and thermal behaviour of 9-substituted 9-thia-10-azaphenanthrenes," Journal of the Chemical Society, XP002277114, Perkin Transactions 1, No. 7, pp. 1733-1747 (1991).
Wilson, et al., "Substituent parameter analysis of the carbon-13 nuclear magnetic resonance chemical shifts of 4-substituted p-terphenyls,"Journal of Organic Chemistry, XP002277115, vol. 47, No.7, pp. 1184-1188 (1982).
Cramer, et al., "Prospective identification of biologically active structures by topomer shape similarity searching," Journal of Medicinal Chemistry, XP002149047, vol. 42, No. 19, pp. 3919-3933 (1999).
Carini, et al., "Nonpeptide angiotensin II receptor antagonists: the discovery of a series of N-(biphenylylmethyl) imidazoles as potent, orally active antihypertensives," Journal of Medicinal Chemistry, XP000674205, vol. 34, No. 8, pp. 2525-2547 (1991).

* cited by examiner

*Primary Examiner*—Joseph K. McKane
*Assistant Examiner*—Joseph R. Kosack
(74) *Attorney, Agent, or Firm*—Francis O Ginah

(57) ABSTRACT

The present invention relates to a melanin concentrating hormone antagonist compound of Formula I: (I) wherein $Ar^1$, $Ar^2$, $Ar^3$, $L^1$, $L^2$ and Q areas defined, or a pharmaceutically acceptable salt, solvate, enantiomer or mixture of diastereomers thereof useful in the treatment, prevention or amelioration of symptoms associated with obesity and Related Diseases $$Ar^1-L^1-Ar^2-Ar^3-L^2-Q. \qquad (I)$$

8 Claims, No Drawings

MCH RECEPTOR ANTAGONISTS

This United States patent application claims priority from International Application No. PCT/US2003/037071, filed Dec. 3, 2003, which claims priority from U.S. Provisional Application No. 60/432,701, filed Dec. 11, 2002.

FIELD OF THE INVENTION

The present invention is in the field of medicine, particularly in the treatment of obesity and diseases caused by or exacerbated by obesity. More specifically, the present invention relates to antagonists of melanin concentrating hormone useful in the prevention and/or treatment of obesity and related diseases.

BACKGROUND OF THE INVENTION

The affluence of the 90's along with the exponential increase in food production particularly in Western and Asian economies has resulted in feeding patterns that lead to obesity. Obesity is defined as being excessively overweight. Excessive weight is generally characterized by excessive body fat, because unused energy is stored in the adipose tissues as fat.

Obesity has associated with it, economic and social costs. Obese people, an increasing proportion of most western societies, are regarded as having out of control feeding habits often associated with low self-esteem. Moreover, obese persons are more likely to have medical problems associated with or exacerbated by the excess body weight. Examples of medical conditions caused, exacerbated or triggered by excessive weight include bone fractures, pains in the knee joints, arthritis, increased risk of hypertension, artherosclerosis, stroke, diabetes, etc.

Melanin concentrating hormone (MCH) is a 19 amino acid neuropeptide produced in the lateral hypothalamic area and zona incerta, although MCH-expressing neurons project to numerous regions of the brain. MCH is processed from a larger pre-prohormone that also includes a second peptide, NEI, and possibly a third, NGE (Nahon, Crit Rev in Neurobiology, 8:221–262, 1994). MCH mediates its effects through at least two G protein-coupled receptors, MCHR1 and MCHR2 (Saito et al. Nature 400: 265–269, 1999; Hill et al., J Biol Chem 276: 20125–20129, 2001). Both receptors are expressed in regions of the brain consistent with MCH neuronal projection and known MCH physiologic function (Hervieu et al., Eur J Neuroscience 12: 1194–1216, 2000; Hill et al., J Biol Chem 276: 20125–20129, 2001; Sailer et al., Proc Nat Acad Sci 98: 7564–7569, 2001).

Extensive evidence exists to support the orexigenic activity of MCH. MCH mRNA is elevated in rodent models of obesity and in the fasted state (Qu et al., Nature 380: 243–247, 1996). Intracerebroventricularly administered MCH increases feeding and blocks the anorexic effect of α-melanocyte stimulating hormone (Ludwig et al., Am J Physiol 274: E627–E633, 1998). MCH knock-out mice ($MCH^{-/-}$ mice) are lean, hypophagic and hypometabolic (Shimada et al., Nature 396: 670–674, 1998), while MCH over-expressing transgenic mice are obese and insulin resistant (Ludwig et al., J Clin Invest 107: 379–386, 2001). $MCHR1^{-/-}$ mice have recently been reported to be lean and hypermetabolic, indicating that the R1 isoform mediates at least some of the metabolic effects of MCH (Marsh et al., Proc Nat Acad Sci 99:3240–3245, 2002; Chen et al., Endocrinology, 2002, in press).

In addition to its effects on feeding, MCH has been implicated in regulation of the hypothalamic-pituitary-adrenal axis through modulation of CRF and ACTH release (Bluet-Pajot et al., J Neuroendocrinol 7: 297–303, 1995). MCH may also play a role in the modulation of reproductive function (Murray et al., J Neuroendocrinol 12: 217–223, 2000) and memory (Monzon et al., Peptides 20: 1517–1519, 1999).

The current preferred treatment for obesity as well as Type II non-insulin dependent diabetes is diet and exercise with a view toward weight reduction and improved insulin sensitivity for diabetics. Patient compliance, however, is usually poor. The problem is compounded by the fact that there are currently only two medications approved for the treatment of obesity (sibutramine, or Meridia™ and orlistat, or Xenical™.

PCT application number WO 01/21577 (JP00/06375) filed Sep. 19, 2000, discloses compounds reportedly useful as antagonists of the MCH receptor. In particular the WO 01/21577 application claims a compound of formula A

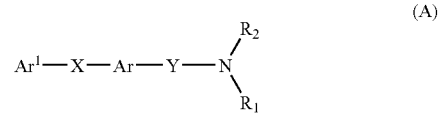

(A)

wherein:
$Ar^1$ is a cyclic group that may have substituents;
X is a spacer having a main chain of 1 to 6 atoms;
Y is a bond or a spacer having a main chain of 1 to 6 atoms;
Ar is a monocyclic aromatic ring which may be condensed with a 4 to 8 membered non-aromatic ring, and may have further substituents;
$R^1$ and $R^2$ are independently hydrogen atom or a hydrocarbon group which may have substituents;
$R^1$ and $R^2$ together with the adjacent nitrogen atom may form a nitrogen-containing hetero ring which may have Substituents; $R^2$ may form a spiro ring together with Ar; or $R^2$, together with the adjacent nitrogen atom and Y, may form a nitrogen-containing hetero ring which may have substituents; or salts thereof.

PCT application number WO 01/82925 also discloses compounds reportedly usefull as antagonists of the MCH receptor. In particular the WO 01/82925 application claims a compound of formula B

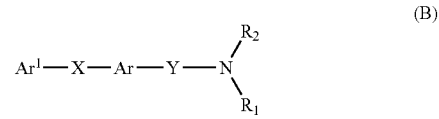

(B)

wherein:
$Ar^1$ is an optionally substituted cyclic group;
X and Y are independently a spacer having a $C_{1-6}$ main chain;
Ar is an optionally substituted fused polycyclic aromatic ring;
$R^1$ and $R^2$ are independently hydrogen atom or an optionally substituted hydrocarbon group; or alternatively $R^1$ and $R^2$ together with the nitrogen atom adjacent thereto may form a nitrogenous heterocycle, or $R^2$ together with the nitrogen atom adjacent thereto and Y may form an optionally substituted nitrogenous heterocycle, or R² together with the nitrogen atom adjacent thereto, Y, and Ar may form a fused ring.

PCT application number WO 01/87834 also discloses compounds reportedly useful as antagonists of the MCH receptor. In particular the WO 01/87834 application claims a compound of formula C.

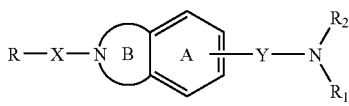

wherein;
R represents hydrogen, halogen, or an optionally substituted cyclic group; X represents a bond or a spacer in which the main chain has one to ten atoms; Y represents a spacer in which the main chain has one to six atoms; ring A represents a benzene ring which may have other substituents; ring B represents a five- to nine-membered nitrogenous nonaromatic heterocycle which may have other substituents; and R¹ and R² are the same or different and each represents hydrogen, an optionally substituted hydrocarbon group, or an optionally substituted heterocyclic group, or R¹ and R² may form an optionally substituted nitrogenous heterocycle in cooperation with the adjacent nitrogen atom and R² may form an optionally substituted nitrogenous heterocycle in cooperation with the adjacent nitrogen atom and Y.

Japanese patent application number JP2001-226269A also discloses compounds reportedly useful as antagonists of the MCH receptor. In particular the JP2001-226269A application claims a compound of formula D.

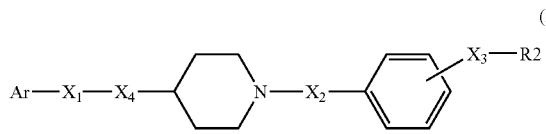

wherein:
Ar is a substituted group-contg. arom. ring, X₁ is a substituted group-contg. divalent main chain of 1–5 atoms, X₂, X₃ and X₄ are linking arms, and R2 is a basic substituting group, and its salts.

PCT application number WO 01/21169 also discloses compounds reportedly useful as antagonists of the MCH receptor. In particular the 01/21169 application claims a compound of formula E.

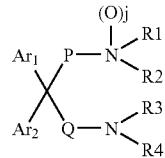

Wherein:
Ar₁ and Ar₂ are each an optionally substituted aromatic group; P and Q are each a divalent aliphatic hydrocarbon group which may contain ethereal oxygen or sulfur in the carbon chain and may be substituted; R1 and R3 are each (i) hydrogen, (ii) acyl, or (iii) optionally substituted hydrocarbyl; R2 and R4 are each (i) hydrogen, (ii) optionally substituted alkyl, or (iii) optionally substituted alkylcarbonyl; alternatively R1 and R2 or R3 and R4 together with the nitrogen atom adjacent thereto may form a monocyclic or fused nitrogenous heterocyclic group; and j is 0 or 1, salts of the same, or prodrugs thereof.

PCT application number WO 02/04433 also discloses compounds reportedly useful as antagonists of the MCH receptor. In particular the 02/04433 application claims a compound of formula F.

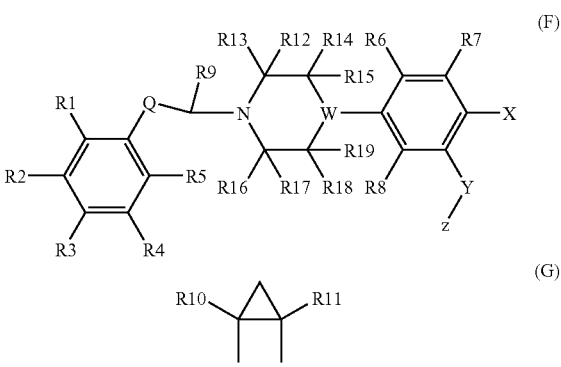

Wherein:
Q=(E)- or (Z)-CR10:CR11, C.triplebond.C, Formula G (wherein A=(un)substituted alkylene); R1–R8=H, halo, CN, etc.; R9–R19=H, allyl; W=N, CRa (Ra=H, OH, alkoxy, etc.); X=halo, CN, NO2, etc.; Y=O, S, SO, SO2; Z allyl, mono, di or trifluoromethyl, etc.

PCT application number WO 02/06245 also discloses compounds reportedly useful as antagonists of the MCH receptor. In particular the 02/06245 application claims compounds of formula H, I, J, K, L, and M.

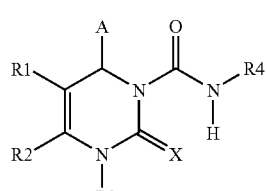

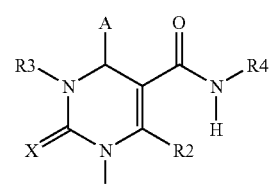

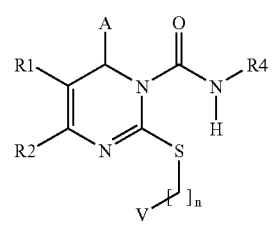

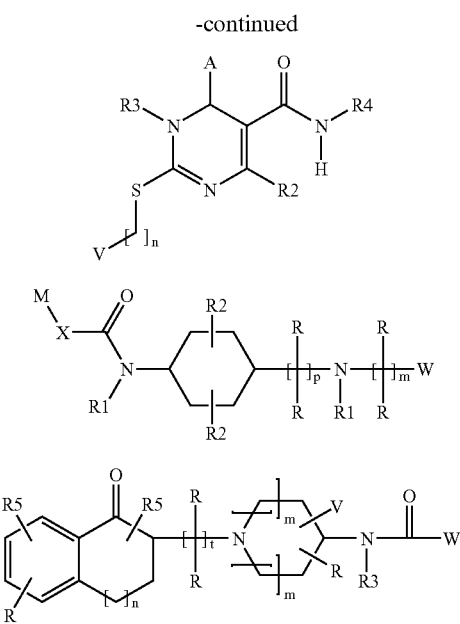

PCT application number WO 02/057233 also discloses compounds reportedly useful as antagonists of the MCH receptor. In particular the 02/057233 application claims a compound of formula N

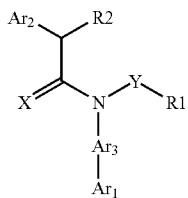

Wherein:
Ar$_1$=(un)substituted (hetero)aryl; Ar$_2$=(un)substituted (hetero)aryl, aralkyl; or Ar$_1$ and Ar$_2$ together form (un)substituted fluorene, fluorenone with the proviso that Ar$_3$ must be arylene; A$_3$=(un)substituted (hetero)arylene; X=O, S, N(CN); Y=a single bond, alkylene; R1=thiazole, (hetero)aryl, etc.; R2=H, alkyl].

PCT application number WO 02/51809 also discloses compounds reportedly useful as antagonists of the MCH receptor. In particular the 02/51809 application claims a compound of formula O

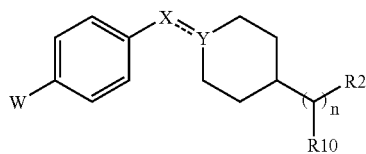

Wherein:
W=R1-CR3R12NR4C(O), R11C(O)NR4; X=CHR8, C(O), C(=NOR9), when the double bond is present CR8=; Y=CH, C(OH), C(alkoxy) or when the double bond is present C; R1=R5-cycloalkyl, R5-(hetero)aryl, R5-heterocycloalkyl; R2=R6-(hetero)aryl; n=1–3; R3=alkyl, (hetero)aryl; R4=H, alkyl; R5=H, alkyl, halo, OH, alkoxy, CF3, alkoxycarbonyl, SO2NHR4, C(O)NHR4, NR4C(O)NHR4, NR4C(O)R4, NR4SO2R4, etc.; R6=H, alkyl, halo, OH, SH, S(alkyl), CN, alkoxy, alkylcarboxy, CF3, NO2, NH2, alkylamino, Ph, alkoxycarbonyl, R7-phenoxy, etc.; R7=H, alkyl, halo, OH, alkoxy, CF3; R8=H, alkyl, alkoxyalkyl; R9=H, alkyl, arylalkyl; R10=H, alkyl, aryl; R11=cyclopropylphenyl or when R2=R6-heteroaryl or R10 is not H, R11 can also be R5-phenyl-alkyl; m=1–5; R12=H, alkyl; R13=H, alkyl, halo, OH, alkoxy, CF3, OCF3, NO2, C(O)CH3; R14=H, alkyl, halo, OH, alkoxy, CF3.

PCT application number WO 02/10146 also discloses compounds reportedly useful as antagonists of the MCH receptor. In particular the 02/10146 application claims a compound of formula P

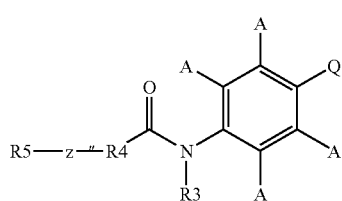

Wherein:
A=H, C1–6alkyl optionally substituted by hydroxyl, C1–6alkoxy, C1–6alkenyl, C1–6 acyl, halogeno, OH, CN, CF3; R3=H, CH3, CH3CH2; R4=arom carbocycle, heterocycle; Z=O, S, NH, CH2, single bond, at the 3 or 4 position of R4 relative to the carbonyl group; R5=arom. carbocycle, heterocycle; Q=XYNR1R2; X=O, S; Y=C2–4 alkylene, C5–6 cycloalkylene; R1, R2 independently=C1–6 alkyl, phenyl-C1–6 alkyl; R1R2=5-, 6-, 7-membered ring optionally contg. one or more heteroatom selected from O, S, N; etc.

PCT application number WO 02/76947 also discloses compounds reportedly useful as antagonists of the MCH receptor. In particular the 02/76947 application claims a compound of formula Q

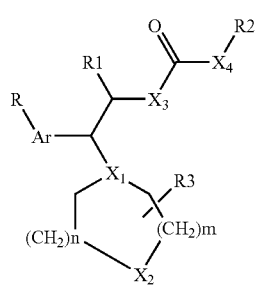

Current treatments targeted at obesity have side effects. Examples of such treatments include phen-fen®, and various over-the-counter appetite suppressants. These agents have not been proven effective for all patients and for sustainable periods of time.

Therefore, there is a need for new and/or improved therapeutically effective agents useful as antagonists of melanin concentrating hormone to better control the dietary habits, minimize the preponderance of obesity and treat, prevent and/or ameliorate the effects of obesity including for example diabetes.

SUMMARY OF THE INVENTION

The present invention relates to a compound of formula I:

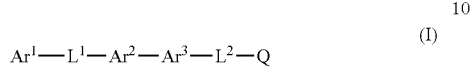

or a pharmaceutically acceptable salt, solvate, enantiomer, mixture of diastereomers, or prodrug thereof; wherein $Ar^1$ is a cyclic group optionally substituted with one to five groups selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, aryl, $C_3$–$C_8$ cycloalkyl, $C_1$–$C_8$ alkylcycloalkyl, cyano, —$(CH_2)_n NR^1R^2$, $C_1$–$C_8$ haloalkyl, halo, $(CH_2)_n COR^6$, $(CH_2)_n NR^5SO_2R^6$, —$(CH_2)_n C(O)NR^1R^2$, and $C_1$–$C_8$ alkylheterocyclic;

wherein the alkyl, alkenyl, cycloalkyl, phenyl, and aryl are each optionally substituted with one to three groups selected from hydroxy, $C_1$–$C_8$ alkoxyalkyl, $C_1$–$C_8$ alkyl, halo, $C_1$–$C_8$ haloalkyl, nitro, cyano, amino, carboxamido, and oxo;

$L^1$ is a bond or a linker having a main chain of 1 to 14 atoms or represented by the formula $X_2$—$(CR^3R^4)_m$—$X_3$ wherein $R^3$ and $R^4$ are independently hydrogen, $C_1$–$C_8$ alkyl, $C_2$–$C_8$ alkylene, $C_2$–$C_8$ alkynyl, phenyl, aryl, $C_1$–$C_8$ alkylaryl, $(CH_2)_n NR^5SO_2R^6$, $(CH_2)_n C(O)R^6$, $(CH^2)_n CONR^1R^2$ or $(CH_2)_n C(O)OR^6$; wherein the alkyl, alkenyl, phenyl, and aryl groups are optionally substituted with one to five substitutents independently selected from oxo, nitro, cyano, $C_1$–$C_8$ alkyl, aryl, halo, hydroxy, $C_1$–$C_8$ alkoxy, $C_1$–$C_8$ haloalkyl, $(CH_2)_n C(O)R^6$, $(CH_2)_n$ CONR$^1$R$^2$ and $(CH_2)_n C(O)OR^6$;

$X_2$ is independently —O, —CH, —CHR$^6$, —NR$^5$, S, SO, or SO$_2$;

$X_3$ is independently —O, —CH, —CHR$^6$, —NR$^5$, S, SO, or SO$_2$;

$Ar^2$ is a 6-member monocyclic carbocyclic or heterocyclic group or positional isomer thereof, having 0, 1, 2, or 3 heteroatoms independently selected from nitrogen, oxygen and sulfur; and optionally substituted with one to three substitutents selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, aryl, $C_3$–$C_8$ cycloalkyl, $C_1$–$C_8$ alkylcycloalkyl, cyano, $C_1$–$C_8$ haloalkyl, halo, $(CH_2)_n C(O)R^6$, $(CH_2)_n C(O)OR^6$, $(CH_2)_n NR^5SO_2R^6$, $(CH_2)_n C(O)NR^1R^2$, and $C_1$–$C_8$ alkylheterocyclic;

provided that the result of the substitution is a stable fragment or group;

$Ar^3$ is a 6-member monocyclic aromatic or nonaromatic, carbocyclic or heterocyclic ring having 0, 1, 2, or 3 heteroatoms selected from nitrogen, oxygen and sulfur and optionally substituted with one to three substitutents independently selected from halo, —NHR$^5$, $C_1$–$C_8$ haloalkyl, $C_3$–$C_8$ cycloalkyl, $C_1$–$C_8$ alkyl, hydroxy, alkoxy, $(CH_2)_n C(O)R^6$, $(CH_2)_n C(O)OR^6$, $(CH_2)_n NR^5SO_2R^6$, $(CH_2)_n C(O)NR^1R^2$, phenyl, $C_1$–$C_8$ alkylaryl, and aryl;

provided that $Ar^2$ and $Ar^3$ or positional isomnersz thereof are linked by a bond;

$L^2$ is a bond or a divalent linker having a chain length of between 1 and 14 atoms in the main chain or represented by the formula:

$X_4$—$(CR^3R^4)_m$—$X_5$ wherein $R^3$ and $R^4$ are independently hydrogen, $C_1$–$C_8$ alkyl, $C_2$–$C_8$ alkylene, $C_2$–$C_8$ alkynyl, phenyl, aryl, $C_1$–$C_8$ alkylaryl, $(CH_2)_n NR^5SO_2R^6$, $(CH_2)_n C(O)R^6$, $(CH_2)_n CONR^1R^2$ or $(CH_2)_n C(O)OR^6$; wherein the alkyl, alkenyl, phenyl, and aryl groups are optionally substituted with one to five substitutents independently selected from oxo, nitro, cyano, $C_1$–$C_8$ alkyl, aryl, halo, hydroxy, $C_1$–$C_8$ alkoxy, $C_1$–$C_8$ haloalkyl, $(CH_2)_n C(O)R^6$, $(CH_2)_n CONR^1R^2$ and $(CH_2)_n C(O)OR^6$;

wherein $X_4$ is selected from the group consisting of —CH, CHR$^6$, —O, —NR$^5$, —NC(O)—, —NC(S), —C(O)NR$^5$—, —NR$^6$C(O)NR$^6$, —NR$^6$C(S)NR$^6$, —NRSO$_2$R$^7$, and —NR$^6$C(NR$^5$)NR$^6$;

$X_5$ is selected from the group consisting of —CH$_2$, —CH, —OCH$_2$CH$_2$, —SO, —SO$_2$, —S, and —SCH$_2$; wherein the group $X_4$—$(CR^3R^4)_m$—$X_5$ imparts stability to the compound of formula (1) and may be a saturated or unsaturated chain or linker;

Q is a basic group or a group represented by —NR$^1$R$^2$; wherein $R^1$ and $R^2$ are independently selected from hydrogen, $C_1$–$C_8$ alkyl, $C_2$–$C_8$ alkenyl, $C_3$–$C_8$ cycloalkane, $C_1$–$C_8$ alkylaryl, —C(O)C$_1$–$C_8$ alkyl, —C(O)OC$_1$–$C_8$ alkyl, $C_1$–$C_8$ alkylcycloalkane, $(CH_2)_n C(O)OR^5$, $(CH_2)_n C(O)R^5$, $(CH_2)_n C(O)NR^1R^2$, and $(CH_2)_n NSO_2R^5$; wherein each of the alkyl, alkenyl, aryl are each optionally substituted with one to five groups independently selected from $C_1$–$C_8$ alkyl, $C_2$–$C_8$ alkenyl, phenyl, and alkylaryl; and wherein $R^1$ and $R^2$ may combine together, and with the nitrogen atom to which they are attached or with 0, 1, or 2 atoms adjacent to the nitrogen atom to form a nitrogen containing heterocycle which may have substituents;

$R^5$ is hydrogen, $C_1$–$C_8$ alkyl, $C_2$–$C_8$ alkenyl, $C_5$–$C_8$ alkylaryl, $(CH_2)_n NSO_2C_1$–$C_8$ alkyl, $(CH_2)_n NSO_2$phenyl, $(CH_2)_n NSO_2$aryl, —C(O)C$_1$–$C_8$ alkyl, or —C(O)OC$_1$–$C_8$ alkyl; and $R^6$ is a group independently selected from hydrogen, $C_1$–$C_8$ alkyl, phenyl, aryl, $C_1$–$C_8$ alkylaryl, and $C_3$–$C_8$ cycloalkyl;

wherein m is an integer from 0 to 4; and n is an integer from 0 to 3.

The present invention also relates to a pharmaceutical formulation comprising, a compound of formula I.

In another embodiment, the pharmaceutical formulation of the present invention may be adapted for use in treating obesity and related diseases.

The present invention also relates to a method for treating obesity in a patient in need thereof, wherein such treatment comprises administering an effective amount of a compound of formula I in association with a pharmaceutically acceptable carrier, diluent or excipient.

The present invention also relates to a method of antagonizing the binding of MCH to MCH receptors useful for the treatment of diseases caused, or exercabated by melanin concentrating hormone.

The present invention is related to the use of a compound of formula I for the manufacture of a medicament for treating obesity and related diseases.

DETAILED DESCRIPTION

For the purposes of the present invention, as disclosed and claimed herein, the following terms are defined below.

The term "main chain" as used herein describes the number of atoms in the shortest distance between two ends of a variable or radical and includes the distance in number of atoms when traversing a straight chain, branched chain or atoms in a mono or bicyclic ring from one end of the variable or radical to the other. For example the compound Ph-OCH$_2$CH$_2$CH$_2$S—CH$_2$Ph, if it represents the groups Ar$^1$L$_1$Ar$^2$, has a chain length of 6 for L$_1$.

The term "C$_1$–C$_8$ alkyl" represents a straight or branched hydrocarbon moiety having from one to eight carbon atoms, including but not limited to methyl, ethyl, n-propyl, isopropyl, n-butyl, isobutyl, sec-butyl, t-butyl, cyclobutyl, pentyl, hexyl, and the like. The term "C$_1$–C$_8$ alkyl" refers more preferably to methyl, ethyl, n-propyl, isopropyl, cyclopropyl, n-butyl, isobutyl, sec-butyl, and t-butyl and the like. Similarly, the term C$_2$–C$_8$ alkenyl refers to a straight or branched hydrocarbon chain having from 1 to 3 double bonds including positional, regio and sterochemcial isomers.

The term "C$_3$–C$_8$ cycloalkyl" as used herein refers to a cyclic hydrocarbon radical or group having from 3 to 8 carbon atoms and having no double bonds. Examples of C$_3$–C$_8$ cycloalkyl groups include but are not limited to cyclopropyl, cyclobutyl, cyclopentyl, cyclohexyl, cycloheptyl, cyclooctyl.

The term "C$_3$–C$_8$ cycloalkenyl" as used herein referes to a cyclic hydrocarbon radical or group having from 3 to 8 carbon atoms and having from 1 to 3 double bonds. Specific examples of C$_{3-8}$ cycloalkenyl include cyclopropenyl, cyclobutenyl, cyclopentenyl, cyclohexenyl, cycloheptenyl, cyclooctenyl, tetrahydrothiophene, tetrahydrofuran.

The term "halo" means halogens including iodo, chloro, bromo and fluoro.

The term "C$_1$–C$_4$ haloalkyl" refers to a C$_1$–C$_4$ alkyl group substituted with one, two or three halogen atoms as possible and as appropriate. Examples of C$_1$–C$_4$ haloalkyl include but are not limited to trifluoromethyl, chloroethyl, and 2-chloropropyl. Similarly, a "C$_1$–C$_8$ haloalkyl" group is a C$_1$–C$_8$ alkyl moiety substituted with up to six halo atoms, preferably one to three halo atoms.

A "C$_1$–C$_8$ alkoxy" group is a C$_1$–C$_8$ alkyl moiety connected through an oxy linkage. The term includes "optionally halogenated C$_1$–C$_8$ alkoxy" groups including for example, C$_1$–C$_8$ alkoxy (e.g. methoxy, ethoxy, propoxy, butoxy, pentyloxy, etc.), which may have 1 to 5, preferably 1 to 3, halogen atoms (e.g. fluorine, chlorine, bromine, iodine, etc.). Concrete examples of alkoxy groups include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy.

The term "cyclic" as used herein refers to substituted or unsubstituted aromatic and non-aromatic ring structures containing hydrocarbon groups, and substituted or unsubstituted aromatic and non-aromatic heterocyclic groups. Cyclic groups may also be monocyclic, bicyclic or polycyclic unless otherwise specified. Examples of aromatic groups include, for example, benzene, thiophene, furan, pyrrole, imidazole, pyrazole, thiazole, isothiazole, oxazole, isoxazole, pyridine, pyrimidine, pyrazine, pyrimidine, pyridazine, 1,2,4-oxadiazole, 1,3,4-oxadiazole, 1,2,4,-thiadiazole, 1,3,4-thiadiazole, pyrrolidine, imidazoline, imidazolidine, pyrazoline, pyrazolidine, tetrahydrothiazole, tetrahydroisothiazole, tetrahydrooxazole, tetrahydroisoxazole, piperidine, tetrahydropyridine, dihydropyridine, piperazine, morpholine, thiomorpholine, tetrahydropyrinidine, tetrahydropyridazine, hexamethyleneimine, benzofuran, benzimidazole, benzoxazole, benzothiazole, benzisothiazole, naphtho[2,3-b]thiophene, isoquinoline, quinoline, indole, quinoxaline, phenanthridine, phenothiazine, phenoxathlin, phenoxazine, naphthylidene, quinazoline, carbazole, b-carboline, acridine, phenazine, phthalimide, and thioxanthene each of which may be optionally substituted.

The term alkylcycloalkyl" as used herein refers to an alkylgroup on which a cycloalkyl group is substituted. Exemplary of alkylcycloalkyl groups are methylcyclopropyl, methylcyclohexyl, methylcycloheptyl, ethylcyclopropyl, etc. The alkylcycloalkyl group may optionally be sustituted independently with one to five groups selected from C$_1$–C$_8$ alkyl, phenyl, aryl, halo, amino, alkylsulfonyl, alkylsulfonamide, haloalkyl, carboxyalkyl, carboxamide, alkoxy, and perfluoroalkoxy.

The term "optionally substituted" as used herein and unless otherwise specified, means an optional substitution of one to five, preferably one to two groups independently selected from halo, hydroxy, oxo, cyano, nitro, phenyl, benzyl, triazolyl, tetrazolyl, 4,5-dihydrothiazolyl, halo, C$_1$–C$_6$ alkyl, C$_1$–C$_4$ haloalkyl, C$_1$–C$_6$ alkoxy, COR$^7$, CONR$^7$R$^7$, CO$_2$R$^7$, NR$^7$R$^7$, NR$^7$COR$^7$, NR$^7$SO$_2$R, OCOR$^8$, OCO$_2$R$^7$, OCONR$^7$R$^7$, SR$^7$, SOR$^8$, SO$_2$R$^8$ and SO$_2$(NR$^7$R$^7$), where R$^7$ is independently at each occurrence H, C$_1$–C$_6$ alkyl phenyl or benzyl and R$^8$ is independently at each occurrence C$_1$–C$_6$ alkyl, phenyl or benzyl.

The term "heterocycle" or "heterocyclic" represents a stable, saturated, partially unsaturated, fully unsaturated or aromatic 4, 5, or 6 membered ring, said ring having from one to three heteroatoms that are independently selected from the group consisting of sulfur, oxygen, and nitrogen. The heterocycle may be attached at any point which affords a stable structure. Representative heterocycles include 1,3-dioxolane, 4,5-dihydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole. The heterocycle is further optionally substituted with one-to three, preferably one or two groups independently selected from halo, hydroxy, oxo, cyano, nitro, phenyl, benzyl, triazolyl, tetrazolyl, 4,5-dihydrothiazolyl, C$_1$–C$_6$ alkyl, C$_1$–C$_4$ haloalkyl, C$_1$–C$_6$ alkoxy, COR$^7$, CONR$^7$R$^7$, CO$_2$R$^7$, NR$^7$R$^7$, NR$^7$COR$^7$, NR$^7$SO$_2$R$^8$, OCOR$^8$, OCO$_2$R$^7$, OCONR$^7$R$^7$, SR$^7$, SOR$^8$, SO$_2$R$^7$ and SO$_2$(NR$^7$R$^7$), where R$^7$ is independently at each occurrence H, C$_1$–C$_6$ alkyl, phenyl or benzyl and R$^8$ is independently at each occurrence C$_1$–C$_6$ alkyl, phenyl or benzyl.

The term "alkylheterodyclic" as used herein refers to an alkyl group further substitued with a heterocyclic group. Examples of alkylheterocycles include but are not limited to 2-methylimidazoline, N-methylmorpholinyl, N-methylpyrrolyl and 2-methylindolyl.

The term "basic radical" refers to an organic radical which is a proton acceptor. Illustrative basic radicals are amidino, guanidino, amino, piperidyl, pyridyl, etc.

The term "basic group" refers to an organic group containing one or more basic radicals. A basic group may comprise only a basic radical.

Suitable basic radicals contain one or more nitrogen atoms and include amino, imino, amidino, N-alkylamidines, N, N'-dialkylamidines, N-arylamidines, aminomethyleneamino, iminomethylamino, guanidino, aminoguanidino, alkylamino, dialkylamino, trialkylaniino, alkylideneamino, pyrrolyl, imidazolyl, pyrazolyl, pyridyl, pyrazinyl, pyrimidinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, amide, thioamide, benzamidino, pteridinyl, 4H-carbazolyl, carbazolyl, beta-carbolinyl, phenanthridinyl, acridinyl, pyrimidinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, or any of the preceding substituted with amino, imino, amidino, aminomethyleneamino, iminomethylamino, guanidino, alkylamino, dialkylamino, trialkylamino, tetrahydroisoquinoline, dihydroisoindole, alkylideneamino, groups, or a group represented by the formula $NR^1R^2$.

The term "suitable solvent" refers to any solvent, or mixture of solvents, inert to the ongoing reaction, that sufficiently solubilizes the reactants to afford a medium within which to effect the desired reaction.

As used herein, the term "patient" includes human and non-human animals such as companion animals (dogs and cats and the like) and livestock animals. Livestock animals are animals raised for food production. Ruminants or "cudchewing" animals such as cows, bulls, heifers, steers, sheep, buffalo, bison, goats and antelopes are examples of livestock. Other examples of livestock include pigs and avians (poultry) such as chickens, ducks, turkeys and geese. Also included are exotic animals used in food production such as alligators, water buffalo and ratites (e.g., emu, rheas or ostriches). The preferred patient of treatment is a human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is sufficient for treating a condition, or detrimental effects thereof, herein described, or an amount of a compound of formula I that is sufficient for antagonizing the MCHR1 receptor to achieve the objectives of the invention.

The term "pharmaceutically acceptable" is used herein as an adjective and means substantially non-deleterious to the recipient patient.

The term "formulation", as in pharmaceutical formulation, is intended to encompass a product comprising the active ingredient(s) (compound(s) of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier, or a compound of the formula I and a pharmaceutically acceptable co-antagonist of MCHR1 useful for the treatment and/or prevention of obesity or a related disease where antagonism of a MCH receptor may be beneficial.

The terms "diseases related to obesity" or "related diseases" as used herein refer to such symptoms, diseases or conditions caused by, exacerbated by, induced by or adjunct to the condition of being obese. Such diseases, conditions and/or symptoms include but are not limited to eating disorders (bulima, anorexia nervosa, etc.), diabetes, diabetic complications, diabetic retinopathy, sexual/reproductive disorders (such as ercetile dysfunction, loss of libido), depression, anxiety, epileptic seizure, hypertension, cerebral hemorrhage, conjestive heart failure, sleeping disorders, atherosclerosis, rheumatoid arthritis, stroke, hyperlipidemia, hypertriglycemia, hyperglycemia, and hyperlipoproteinenamia.

The term "unit dosage form" refers to physically discrete units suitable as unitary dosages for human subjects and other non-human animals (as described above), each unit containing a predetermined quantity of active material calculated to produce the desired therapeutic effect, in association with a suitable pharmaceutical carrier.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkalines, and the like.

Because certain compounds of the invention contain a basic moiety (e.g., amino), the compound of formula I may also exist as a pharmaceutical acid addition salt. Such salts include the salicylate, sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and like salts. Preferred acid addition salts include the hydrochloride and glycolate salts. Acid addition salts are typically formed by reacting an equivalent amount of acid (based on moles of available basic i.e free pairs of electrons on nitrogen atoms, or a slight excess thereof) with the free base compound of the invention. The addition salt product is often isolated as the crystallization product. The crystallization may be spontaneous or may be facilitated by cooling and or seeding. Other methods of isolating the acid addition salts are known to one of skill in the art.

PREFERRED COMPOUNDS OF THE INVENTION

Certain compounds of the invention are particularly preferred. The following listing sets out several groups of preferred variables and/or compounds. It will be understood that each of the listings may be combined with other listings to create additional groups of preferred compounds.

Preferred $Ar^1$

Preferred $Ar^1$ groups are cyclic groups selected from cycloalkyl and cycloalkene groups such as the group consisting of cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl; and groups selected from tetrahydrothiophene, tetrahydrofuran, pyrrolidine, imidazoline, imidazolidine, indole, isoindolylyl, pyrazoline, pyrazolidine, tetrahydrothiazole, tetrahydroisothiazole, tetrahydrooxazole, phenyl, tetrahydroisoxazole, piperidine, tetrahydropyridine, benzothiophene, benzofuran, naphthyl, dihydropyridine, piperazine, morpholine, thiomorpholine, tetrahydropyrimidine, tetrahydropyridazine, hexamethyleneimine, each optionally substituted with $C_1$–$C_6$ alkyl, $C_1$–$C_6$ cycloalkyl, $C_1$–$C_6$ haloalkyl, hydroxy, alkoxyalkyl, cyano, halo, phenyl, aryl, carboxamide, and $C_1$–$C_6$ carboxyalkyl. More preferred $Ar^1$ groups include cycloalkyl, cycloalkenyl, phenyl, benzothiophene, benzofuran and naphthyl.

Preferred $L^1$ Groups

Preferred $L^1$ groups are selected from the group consisting of —$CH_2$—, —$CH_2CH_2$—, —$CH_2CH_2CH_2$—, —$SCH_2$—, —$OCH_2$—, —$CH_2SCH_2$—, —$CH_2OCH_2$—, —$OCH_2CH_2SCH_2$—, —$OCH_2CH_2OCH_2$—, —$O(CH_2)_3SCH_2$—, —$OCH(Et)CH_2CH_2SCH_2$, —$OCH(iPr)CH_2CH_2SCH_2$, —$OCH(CH_3)CH_2CH_2SCH_2$—$O(CH_2)_3SCH(CH_3)$—, —$O(CH_2)_2SCH(CF_3)$—, —$OCH_2CH(NO_2)SCH_2$—, —$OCH(CN)CH_2SCH_2$, —$OCH_2CH(NH_2)SCH_2$—, —$CH_2O(CH_2)_3CH_2O$—, and —$CH_2O(CH_2)_2CH_3O$—.

Also preferred is an $L_1$ group having the formula $X_2$—$(CR^3R^4)_m$—$X_3$ wherein a preferred $X_2$ group is selected from O, S, and —$NR^6$, wherein $R^6$ is selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl.

Preferred $X_3$ Groups

Also preferred is an $L^1$ group wherein, when $L^1$ is $X_2$—$(CR^3R^4)_m$—$X_3$; $X_3$ is a group selected from —$OCH_2$, —$SCH_2$, —$NR^6C(O)CH_2$, —$NHCH_2$, wherein $R^6$ is selected from the group consisting of hydrogen, $C_1$–$C_6$ alkyl, $C_2$–$C_6$ alkenyl, $C_3$–$C_8$ cycloalkyl, phenyl, benzyl, and aryl. More preferred is an $X_3$ group selected from —$OCH_2$, and —$SCH_2$.

Also preferred is a compound of formula I wherein $L^1$ is $X_2$—$(CR^3R^4)_m$—$X_3$, and wherein the chain between $X_2$ and $X_3$ i.e., —$(CR^3R^4)_m$— is an alkyl chain of 3 to 8 carbon atoms, or an alkenyl chain of 3 to 8 carbon atoms and optionally having an alkyl, phenyl, amino, or cycloalkyl group as a side chain.

Preferred $Ar^2$ Groups

A preferred $Ar^2$ group is a 6-member monocyclic carbocyclic or heterocyclic group having 0, 1 or 2 heteroatoms selected from oxygen, sulfur, and nitrogen. More preferred is a group selected from pyridazinyl, pyrimidinyl, pyran, piperidinyl, phenyl, cyclohexyl, pyridinyl and piperazinyl. Most preferred $Ar^2$ is the group phenyl, preferably attached in a 1,2. or 1,3 relationship to the $Ar^3$ group.

Preferred $Ar^3$ Groups

A preferred $Ar^3$ group is a 6-member carbocyclic or heterocyclic group having 0, 1, 2, or 3 heteroatoms independently selected from oxygen, sulfur, and nitrogen and optionally substituted with one to two groups. More preferred is a cyclic group selected from phenyl, pyran, piperidine, pyridine, pyridazine, and piperazine. Most preferred $Ar^3$ is phenyl.

Preferred $L^2$ Groups

Certain preferred $L^2$ groups are selected from the group consisting of —$OCH_2CH_2$—, —$O(CH_2)_3$—, —$CH_2$, —$CH_2CH_2$, —$CH_2CH_2CH_2$, —$CH=CH$, —$CH_2CH_2CH=CH$— and $X_4$—$(CR^3R^4)_m$—$X_5$.

Preferred $X_4$ Groups

Preferred $X_4$ groups include divalent groups, radicals, or fragments of the formula —$C(O)NR^6$ wherein $R^6$ is selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl.

Also preferred is an $X_4$ group selected from O, S, —$NR^6C(O)NR^6$, —$C(S)NR^6$, $NR^6C(S)NR^6$, $NR^6C(NR^6)NR^6$, —$NR^6SO_2$—, wherein $R^6$ is independently selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl.

Preferred $X_5$ Groups

Preferred is an $X_5$ group selected from —$OCH_2$, —$SCH_2$, O, —$NR^6C(O)$, —$NR^6C(S)$, —$C(O)NR^6$, —$C(S)NR6$, $NR^6C(S)NR^6$, $NC(NR^6)N$, $NR^6C(O)NR^6$, —$NR^6SO_2$ wherein $R^6$ is independently selected from the group consisting of hydrogen, $C_1$–$C_6$ alkyl, $C_2$–$C_6$ alkenyl, $C_3$–$C_8$ cycloalkyl, phenyl, benzyl, $C_1$–$C_8$ alkylamine, and aryl. More preferred is an $X_5$ group selected from —$OCH_2$, $SCH_2$ and O.

Also preferred is a compound of formula I wherein the chain between $X_4$ and $X_5$ is preferably an alkyl chain of 2 to 8 carbon atoms, or an alkenyl chain of 2 to 8 carbon atoms and optionally contains an allyl, phenyl, or cycloalkyl group as a side chain.

Preferred Q Groups:

The substituent Q of formula I is a basic group. A basic group is an organic group containing one or more basic radicals. Preferred Q groups are those represented by the formula —$NR^1R^2$.

Preferred $R^1$ and $R^2$ Groups

Preferred $R^1$ and $R^2$ groups are independently selected from the group consisting of hydrogen, $C_1$–$C_6$ alkyl, $C_2$–$C_6$ alkenyl, $C_3$–$C_8$ cycloalkyl, $C_3$–$C_8$ alkylcycloalkyl, phenyl, benzyl, $COR^9$, $SO_2R^9$, and $(CH_2)_nSO_2R^6$.

Also preferred are $R^1$ and $R^2$ groups which combine with each other, and the nitrogen atom to which they are attached to form a heterocycle selected from morpholino, thiomorpholino, pyrrole, 2H-pyrrole, 2-pyrroline, pyrrolidine, oxazole, thiazole, imidazoline, imidazolidine, pyrazole, pyrazoline, piperazinyl, piperadinyl, pyrazinyl, pyrimidine each optionally substituted with a $C_1$–$C_8$ alkyl group.

Also preferred is a compound of the invention having $R^1$ and $R^2$ groups wherein the $R^1$ and $R^2$ groups combine with the nitrogen atom to which they are attached and with a carbon atom one or two atoms removed from the nitrogen atom to form a cycle such as for example, azepine, diazepine, pyridine, piperidine, indolyl, N-methylpyrrolidinyl, pyrrolidinyl, morpholino, piperidinyl, and the like.

Most preferred are $R_1$ and $R_2$ which singly or in combination with each other and/or the nitrogen atom to which they are attached form the groups independently selected from methyl, ethyl, propyl, isopropyl, isobutyl, cyclopentyl, cyclohexyl, N-morpholino, azepane, diazepine, pyridine, pyrrolidine, piperidine, N-methylpiperidine, and N-methylpiperazine.

Preferred $R^3$ and $R^4$ Groups:

Preferred $R^3$ and $R^4$ are independently selected from hydrogen, $C_1$–$C_8$ alkyl, $C_2$–$C_8$ alkylene, $C_2$–$C_8$ alkynyl, phenyl, aryl, $C_1$–$C_8$ alkylaryl, $(CH_2)_nNR^5SO_2R^6$, $(CH^2)_nC(O)R^6$ $(CH_2)_nCONR^1R^2$ and $(CH_2)_nC(O)OR^6$; wherein the alkyl, alkenyl, phenyl, and aryl groups are optionally substituted with one to three substitutents independently selected from oxo, nitro, cyano, $C_1$–$C_8$ alkyl, aryl, halo, hydroxy, $C_1$–$C_8$ alkoxy, $C_1$–$C_8$ halaoalkyl, $(CH_2)_nC(O)R^6$, $(CH^2)_nCONR^1R^2$ and $(CH_2)_nC(O)OR^6$.

Most preferred $R^3$ and $R^4$ substituents are independently selected from hydrogen, $C_1$–$C_8$ alkyl, $C_2$–$C_8$ alkylene, $C_2$–$C_8$ alkynyl, phenyl, and benzyl; and wherein n is 0, or 1, and wherein $R^5$ is hydrogen, $C_1$–$C_8$ alkyl, phenyl or benzyl; and wherein $R^6$ is hydrogen, $C_1$–$C_8$ alkyl, phenyl or benzyl.

Preferred $R^5$ Groups

A preferred $R^5$ group is a group independently selected from hydrogen, $C_1$–$C_8$ alkyl, $C_1$–$C_8$ alkoxy, $C_2$–$C_8$ alkenyl, $C_5$–$C_8$ alkylaryl, $(CH_2)_nNSO_2C_1$–$C_8$ alkyl, $(CH_2)_nNSO_2$phenyl, $(CH_2)_nNSO_2$aryl, —$C(O)C_1$–$C_8$ alkyl, and —$C(O)OC_1$–$C_8$ alkyl.

Preferred $R^6$ Groups

A preferred $R^6$ group is a group independently selected from hydrogen, $C_1$–$C_8$ alkyl, phenyl, aryl, alkylaryl, and $C_3$–$C_8$ cycloalkyl.

A particularly preferred compound of the present invention is a compound selected from the group consisting of:

4'-(2-phenoxy-ethylsulfanylmethyl)-biphenyl-3-carboxylic acid(3-dimethylamino-propyl)-amide oxalate

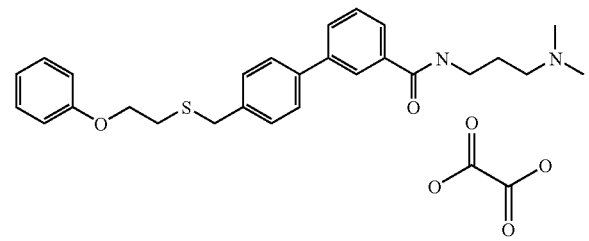

4'-(2-phenoxy-ethylsulfanylmethyl)-biphenyl-3-carboxylic acid(2-dimethylamino-ethyl)-amide oxalate,

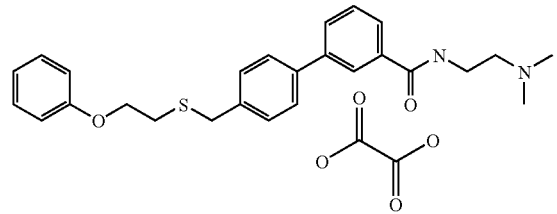

4'-(2-phenoxy-ethylsulfanylmethyl)-biphenyl-3-carboxylic acid(4-dimethylamino-butyl)-amide oxalate,

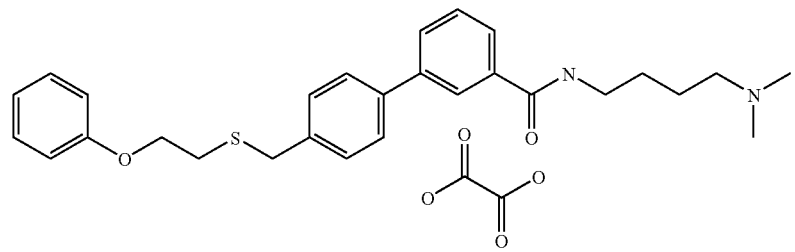

4'-(2-phenoxy-ethylsulfanylmethyl)-biphenyl-4-carboxylic acid(2-dimethylamino-ethyl)-amide oxalate,

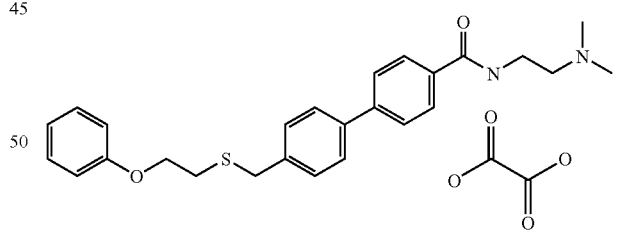

4'-(2-phenoxy-ethylsulfanylmethyl)-biphenyl-4-carboxylic acid(3-dimethylamino-propyl)-amide hydrochloride,

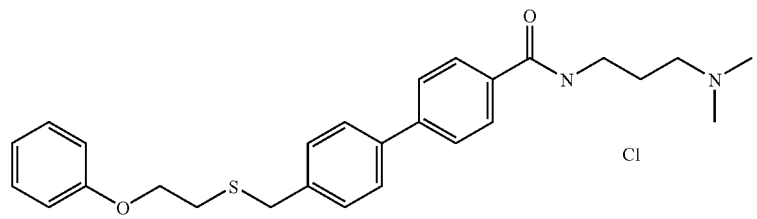

4'-(2-phenoxy-ethylsulfanylmethyl)-biphenyl-4-carboxylic acid(4-dimethylamino-butyl)-amide oxalate,

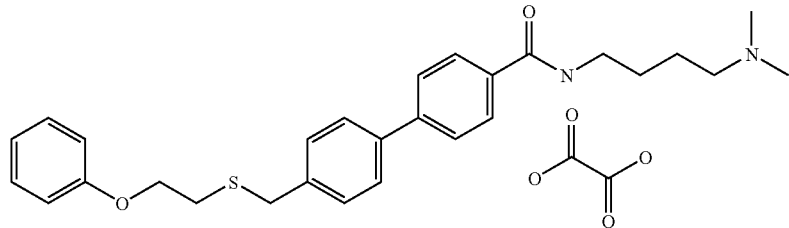

4'-(2-phenoxy-ethylsulfanylmethyl)-biphenyl-2-carboxylic acid(2-dimethylamino-ethyl)-amide oxalate,

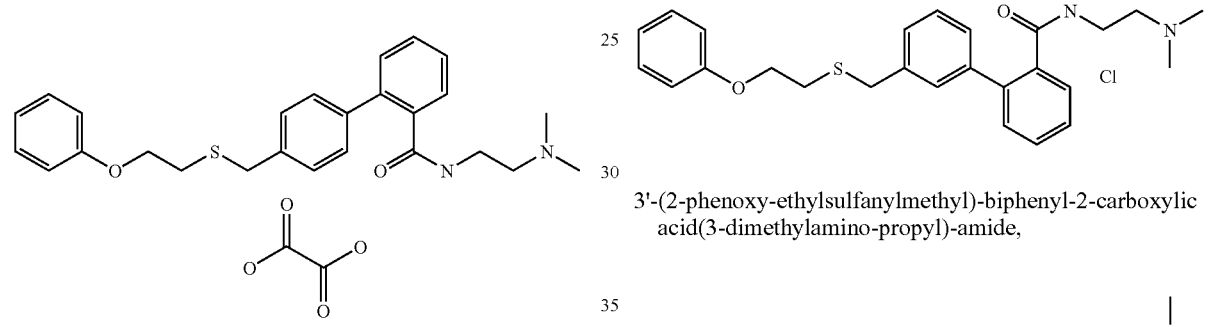

4'-(2-phenoxy-ethylsulfanylmethyl)-biphenyl-2-carboxylic acid(3-dimethylamino-propyl)-amide,

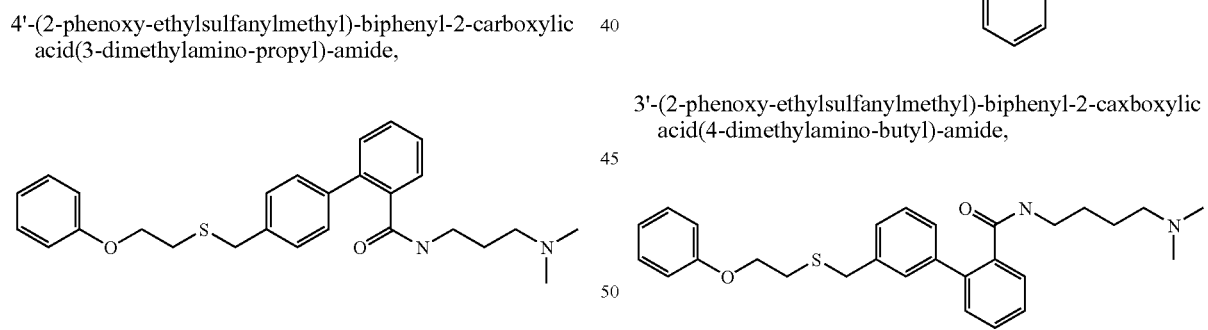

4'-(2-phenoxy-ethylsulfanylmethyl)-biphenyl-2-carboxylic acid(4-dimethylamino-butyl)-amide oxalate,

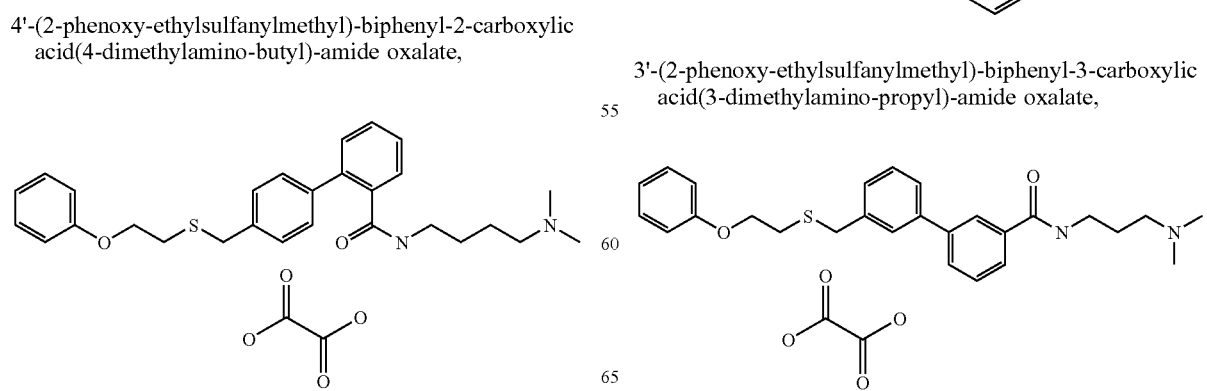

3'-(2-phenoxy-ethylsulfanylmethyl)-biphenyl-2-carboxylic acid(2-dimethylamino-ethyl)-amide hydrochloride, 3'-(2-phenoxy-ethylsulfanylmethyl)-biphenyl-2-carboxylic acid(3-dimethylamino-propyl)-amide, 3'-(2-phenoxy-ethylsulfanylmethyl)-biphenyl-2-caxboxylic acid(4-dimethylamino-butyl)-amide, 3'-(2-phenoxy-ethylsulfanylmethyl)-biphenyl-3-carboxylic acid(3-dimethylamino-propyl)-amide oxalate, 3'-(2-phenoxy-ethylsulfanylmethyl)-biphenyl-4-carboxylic acid(2-dimethylamino-ethyl)-amide,

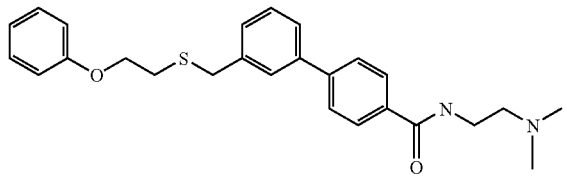

3'-(2-phenoxy-ethylsulfanylmethyl)-biphenyl-4-carboxylic acid(3-dimethylamino-propyl)-amide oxalate,

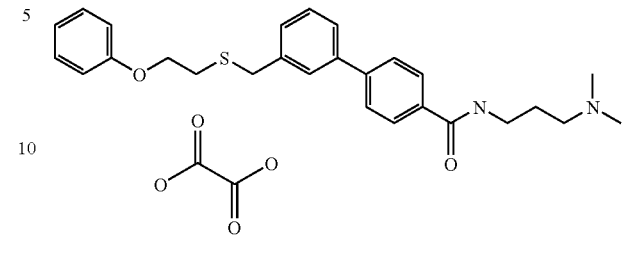

3'-(2-phenoxy-ethylsulfanylmethyl)-biphenyl-4-carboxylic acid(4-dimethylamino-butyl)-amide oxalate,

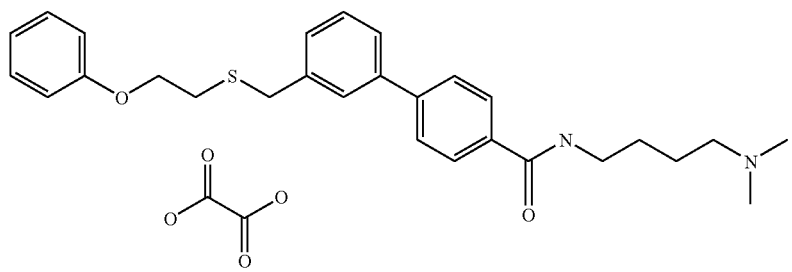

2'-(2-phenoxy-ethylsulfanylmethyl)-biphenyl-2-carboxylic acid(2-dimethylamino-ethyl)-amide oxalate,

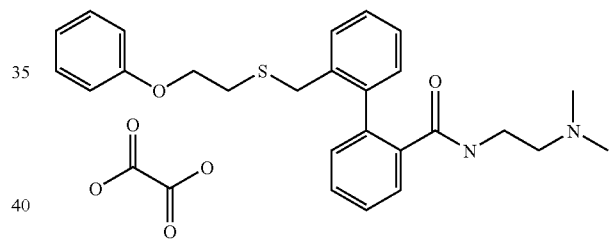

2'-(2-phenoxy-ethylsulfanylmethyl)-biphenyl-2-carboxylic acid(3-dimethylamino-propyl)-amide,

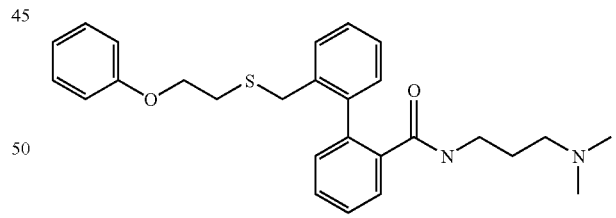

2'-(2-phenoxy-ethylsulfanylmethyl)-biphenyl-2-carboxylic acid(4-dimethylamino-butyl)-amide oxalate,

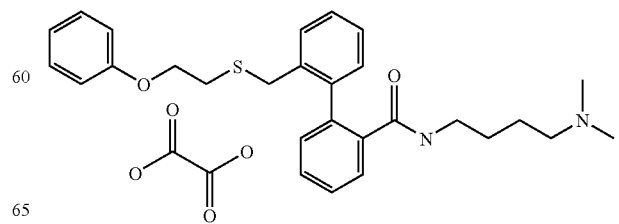

2'-(2-phenoxy-ethylsulfanylmethyl)-biphenyl-3-carboxylic acid(2-dimethylamino-ethyl)-amide oxalate,

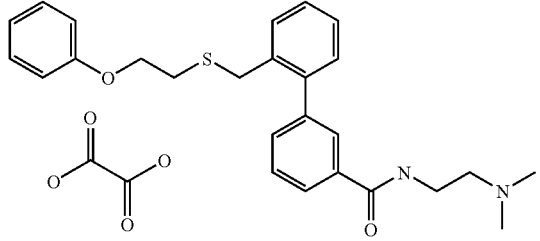

2'-(2-phenoxy-ethylsulfanylmethyl)-biphenyl-3-carboxylic acid(3-dimethylamino-propyl)-amide oxalate,

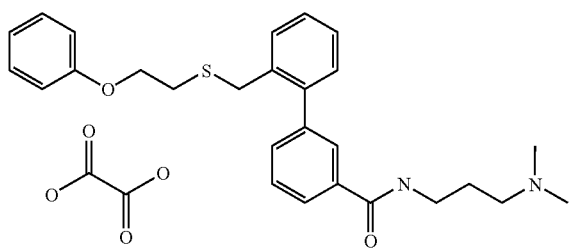

2'-(2-phenoxy-ethylsulfanylmethyl)-biphenyl-3-carboxylic acid(4-dimethylamino-butyl)-amide oxalate,

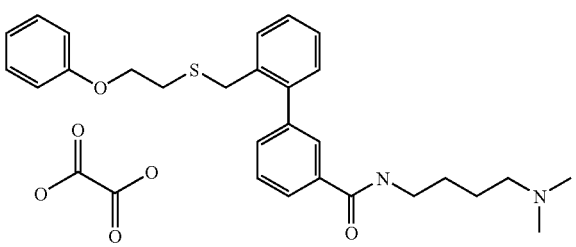

2'-(2-phenoxy-ethylsulfanylmethyl)-biphenyl-4-carboxylic acid(2-dimethylamino-ethyl)-amide,

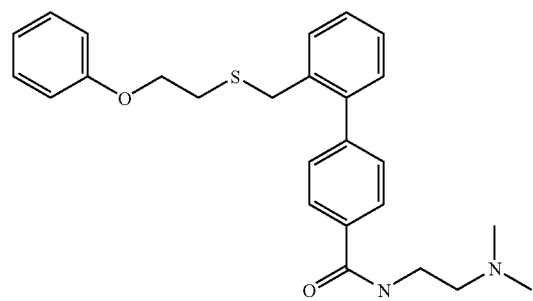

2'-(2-phenoxy-ethylsulfanylmethyl)-biphenyl-4-carboxylic acid(3-dimethylamino-propyl)-amide,

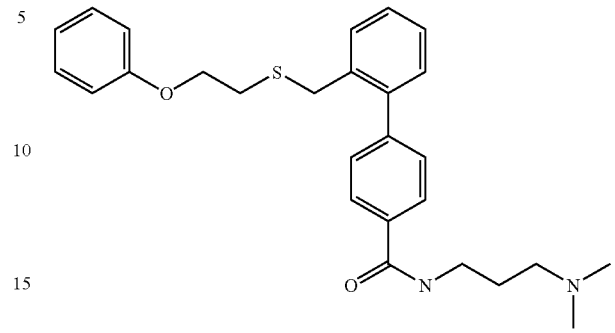

2'-(2-phenoxy-ethylsulfanylmethyl)-biphenyl-4-carboxylic acid(4-dimethylamino-butyl)-amide,

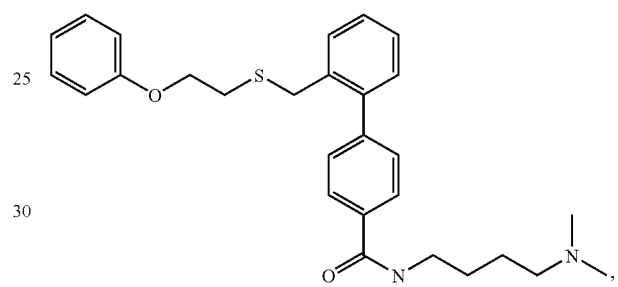

or a pharmaceutically acceptable salt, enatiomer, solvate or prodrug thereof.

PREPARING COMPOUNDS OF THE INVENTION

Compounds of formula I may be prepared as described in the following Schemes and Examples.

Precursors to the compounds of the invention are prepared by methods known to one of skill in the art. The compounds employed as initial starting materials in the synthesis of compounds of the invention are well known and, to the extent not commercially available, are readily synthesized by standard procedures commonly employed by those of ordinary skill in the art.

More particularly, the compounds of the invention are produced in accordance with the General Methods 1 through 5 that are described in detail below, or analogous methods thereto. These reactions are often carried out in accordance with known methods, or analogous methods thereto. Examples of such known methods include the methods described in general reference texts such as Organic Functional Group Preparations, $2^{nd}$ Edition, 1989; Comprehensive Organic Transformations, VCH Publishers Inc, 1989; Compendium of Organic Synthetic Methods, Volumes 1–10, 1974–2002, Wiley Interscience; March's Advanced Organic Chemistry, Reactions Mechanisms, and Structure, $5^{th}$ Edition, Michael B. Smith and Jerry March, Wiley Interscience, 2001, Advanced Organic Chemistry, $4^{th}$ Edition, Part B, Reactions and Synthesis, Francis A. Carey and Richard J. Sundberg, Kluwer Academic/Plenum Publishers, 2000, etc., and references cited therein.

General Method 1: Coupling of the Basic Group

The compounds of Formula 3 can be prepared by the General Method 1, described in General Scheme 1, via coupling of a compound of Formula 2 containing a basic group with a group of Formula 1, where during the course of the coupling reaction the coupling groups are retained or lost to form the linker $L_2$ between the basic group and the phenyl ring. $Ar^1$, $L^1$, $Ar^2$, $L^2$, and basic group are defined as above. In the schemes that follow $Ar^3$ of formula I has been depicted as a phenyl group for convenience only and is not intended to be limiting. Also, $L_a$ is defined as a group that when the coupling process occurs results in the formation of the linker $L^2$ defined above. Furthermore, in the schemes that follow, the group $L^1$ is depicted by the combination of group or groups interspacing or linking the groups $Ar^1$ and $Ar^2$. Similarly, the group $L^2$ is depicted by the combination of group or groups interspacing or linking the groups $Ar^3$ and the basic group. The basic group of the compounds of the following schemes in general mean the group $-N(R^1R^2)$ unless otherwise indicated. Examples of the General Method 1 are a Displacement Process (Scheme 1a) and a Reductive Amination Process (Scheme 1b).

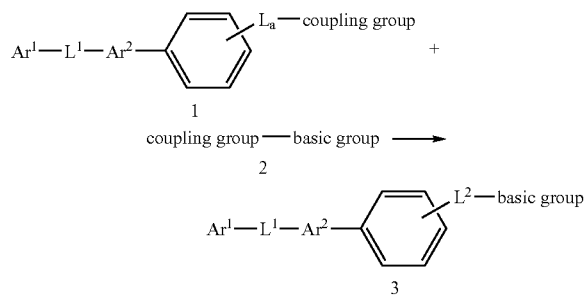

As outlined in Scheme 1a below, the coupling process of General Method 1 may consist of a displacement process whereby nucleophilic displacement of a leaving group, such as, but not limited to halogen, triflate, tosylate, brosylate, mesylate, nosylate, nonaflate, tresylate, and the like, of Formula 4, by a nucleophilic basic group of Formula 5 affords the compounds of the invention. A leaving group is defined in one or more of the general reference texts described previously.

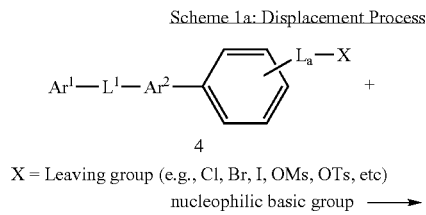

One to five equivalents of the nucleophilic basic group of Formula 5 and one to five equivalents of the reactive derivative of Formula 4 may be reacted in the presence, or absence, of an inert solvent.

If necessary, the reaction may be carried out in the presence of a catalytic quantity to about five equivalents of a non-interfering base. A non-interfering base is a base suitable for the intended reaction by virtue of the base not deleteriously affecting the reaction. One to two equivalents of base is normally preferable. The reaction is normally carried out between 0° C. and 120° C. Reaction time is normally 4 to 24 hours.

Nucleophilic basic groups would include, but would not be limited to ammonia, primary and secondary amines, guanidines, and the like. Specific nucleophilic basic groups include ammonia, methylamine, dimethylamine, diethylamine, diisopropylamine, pyrrolidine, piperidine, morpholine, azetidine, thiomorpholine, piperazine, imidazole, and the like. Among the above nucleophilic basic groups dimethylamine, pyrrolidine, and piperidine are preferable.

If necessary, the reaction can be carried out with nucleophilic basic group synthon, i.e., a group that could readily be converted to a basic group by methods known to one skilled in the art. Nucleophilic basic group synthons would include, but would not be limited to, azide, phthalimide, protected amines, hexamethylenetetramine, cyanamide, cyanide anion, and the like. Following the displacement reaction, these groups would then be unmasked under standard conditions to afford the basic group. For example, displacement with potassium phthalimide followed by removal of the phthalimide group to afford the primary amine as in the Gabriel synthesis (see, March's Advanced Organic Chemistry, Reactions Mechanisms, and Structure, $5^{th}$ Edition, Michael B. Smith and Jerry March, Wiley Interscience, 2001, Chapter 10, and references cited therein). Application of the synthon equivalent to the basic group applies to the processes described in all of the General Methods 1 through 5. Examples of "inert solvent" include amide solvents (preferably DMF or DMAC), sulfoxide solvents (preferably DMSO), sulfone solvents (preferably sulfolane or dimethylsulfone), nitrile solvents (preferably acetonitrile), halogenated hydrocarbon solvents (preferably dichloromethane), aromatic solvents (preferably toluene or benzene), ether solvents (preferably diethylether or THF), ketone solvents (preferably acetone), ester solvents (preferably ethyl acetate), alcohol solvent (preferably MeOH or EtOH), etc. Two or more of the solvents can be mixed in an appropriate ratio for use. Among the above solvents, DMF and DMSO are preferable.

Examples of "base" include, for instance, hydrides of alkali metals and alkaline earth metals (e.g., lithium hydride, sodium hydride, potassium hydride, and the like), amides of alkali metals and alkaline earth metals (e.g., sodium amide, lithium diisopropyl amide, lithium hexamethyldisilazide, and the like), alkoxides (e.g. sodium methoxide, sodium ethoxide, potassium t-butoxide, and the like), inorganic bases, such as hydroxides of alkali metals or alkaline earth metals (e. g., sodium hydroxide, lithium hydroxide, potassium hydroxide, and the like), carbonates and hydrogen carbonates of alkali metals or alkaline earth metals (e. g., potassium carbonate, sodium bicarbonate, sodium carbonate, cesium carbonate, and the like), amine bases (such as, N-methylmorpholine, DBU, DBN, pyridine, 2,6-lutidine, triethylamine, diisopropylethylamine, and the like). Among the above bases, sodium hydride, potassium carbonate, and cesium carbonate are preferable.

As outlined in Scheme 1b below, the coupling process can consist of a Reductive Amination Process. A compound of Formula 6 is condensed with ammonia, or a primary, or secondary amine under dehydration/reduction conditions. Scheme 1b is a process analogous to that described in for example, Chem Pharm Bull 1999, 47 (8), 1154–1156; Synlett 1999, (11), 1781–1783; and J Med Chem 1999, 42 (26), 5402–5414 and references cited therein.

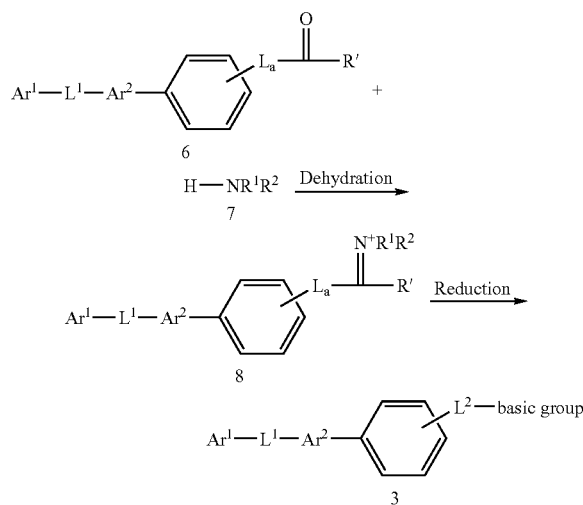

The carbonyl compound of Formula 6 is reacted with an amine of Formula 7 in an inert solvent under conditions that form the iminium species of Formula 8. The iminium species is reduced in-situ to form the compounds of Formula 3. The reaction is normally done in the presence of a dehydrating agent and a reducing agent. Amines of Formula 7 include, but are not be limited to ammonia, primary and secondary amines, and the like. Specific amine groups include ammonia, methylamine, dimethylamine, diethylamine, diisopropylamine, pyrrolidine, piperidine, morpholine, azetidine, thiomorpholine, piperazine, imidazole, and the like. One to five equivalents of the amine group of Formula 7 and one to five equivalents of the reactive derivative of Formula 6 are reacted in the presence, or absence, of an inert solvent. The use of an excess of dehydrating agent is normally preferable. The reaction is carried out in the presence of one to hundred equivalents of a reducing agent. One to three equivalents of reducing agent is preferable. The reaction is normally carried out between 0° C. and 120° C. Reaction time is normally 4 to 24 hours. For the above amination reaction, MeOH and EtOH are preferable as inert solvents.

Examples of "dehydrating agents" include anhydrous molecular sieves beads, anhydrous molecular sieve pellets, powdered anhydrous molecular sieves, anhydrous molecular sieves on supports (such as zeolite), anhydrous magnesium sulfate, anhydrous sodium sulfate, and the like. Among the above dehydrating agents, anhydrous molecular sieves pellets and powdered anhydrous molecular sieves are preferable. Examples of "reducing agents" include hydrogen gas or hydrogen gas precursor and a hydrogenation catalyst. Other "reducing agents" include sodium cyanoborohydride, sodium triacetoxyborohydride, sodium borohydride, sodium borohydride/Ti (Oi-Pr)4, borohydride-exchange resin, and the like. Examples of "hydrogen gas precursors" include formic acid, 1,4-cyclohexadiene, and the like. Examples of "hydrogenation catalyst" include 5–10% palladium on carbon, 1–10% platinum on carbon, rhodium, ruthenium, nickel and the like. The metal can be used as a finely dispersed solid or absorbed on a support, such as carbon or alumina. Among the above reducing agents, sodium cyanoborohydride and sodium triacetoxyborohydride are preferred.

General Method 2: Coupling of the Linker Group

The compounds of Formula 3 can be prepared by the General Method 2, described in General Scheme 2, via reaction of the coupling group of Formula 9 with a coupling group of Formula 10, Examples of the General Method 2 are an Ether/Thioether Alkylation Process (Scheme 2a), an Acylation/Sulfonylation Process (Scheme 2b), Urea/Thiourea/Guanidine Coupling Process (Scheme 2c1, 2c2, 2c3), an Organometallic Process (Scheme 2d), and a Wittig-type Coupling (Scheme 2e).

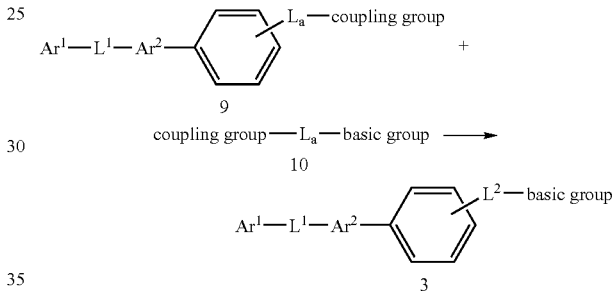

As outlined in Scheme 2a below, the coupling process of General Method 2 can consist of a Ether/Thioether Alkylation Process. Nucleophilic displacement by an alcohol or thiol-containing compound of Formula 11 (or Formula 11') with a compound of Formula 12 (or Formula 12') containing a leaving group affords the ether and thioether compounds of Formula 13. Scheme 2a is a process analogous to that described in The Chemistry of the Ether Linkage; Patai, Wiley, 1967, 446, 460; and in March's Advanced Organic Chemistry, Reactions Mechanisms, and Structure, 5$^{th}$ Edition, Michael B. Smith and Jerry March, Wiley Interscience, 2001, Chapter 10.

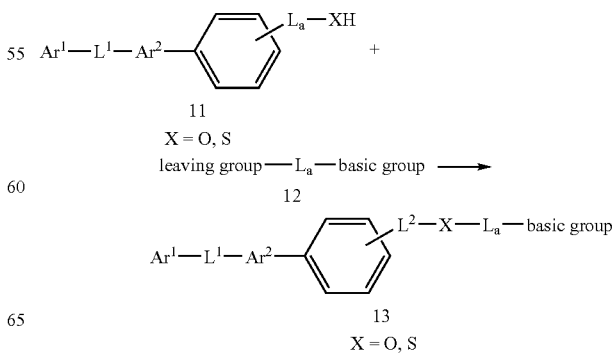

-continued

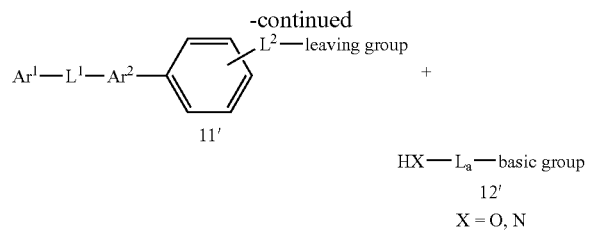

One to five equivalents of the alcohol or thiol of Formula 11 (or Formula 11') and one to five equivalents of the reactive derivative of Formula 12 (or Formula 12') are reacted in the presence, or absence, of an inert solven. If necessary, the reaction can be carried out in the presence of a catalytic quantity to ten equivalents of a non-interfering base. One to three equivalents of base is normally preferable. The reaction is typically carried out between 0° C. and 120° C. Reaction time is typically from about 4 to about 24 hours, but may be shorter or longer depending on the particular substrate. Preferred bases for the above reaction include sodium hydride, potassium carbonate and cesium carbonate.

If necessary, the reaction may be performed with basic group synthon incorporated as the basic group in Formula 12, i.e., a group that could readily be converted to a basic group by methods known to one skilled in the art. Basic group synthons would include, but not be limited to, halogen, protected amine, nitrile, aldehyde, and the like. Following the ether/thioether alkylation reaction, these groups would then be unmasked or converted under standard conditions to afford the basic group. For example, alkylation with 1-iodo-4-chloro-butane would give a 4-chlorobutane derivative of compound 11. The chloride could then be converted by the Displacement Process, described above in Scheme 1a, into the basic group of a compound of Formula 13. Among the inert solvents, DMF and DMSO are preferable.

As outlined in Scheme 2b below, the coupling process of General Method 2 can consist of a Acylation/Sulfonylation Process. Acylation or sulfonylation of an alcohol or amine compound of Formula 14 with a carboxylic acid or sulfonic acid compound of Formula 15, affords the ester, amide, sulfonic ester, or sulfonamide compounds of Formula 16. Alternatively, acylation or sulfonylation of an alcohol or amine compound of Formula 18 with a carboxylic acid or sulfonic acid compound of Formula 17 affords the ester, amide, sulfonic ester, or sulfonamide compounds of Formula 19.

If necessary, the reaction can be carried out with a basic group synthon incorporated as the basic group in Formula 15 or Formula 18, i.e., a group that could readily be converted to a basic group by methods known to one skilled in the art. Basic group synthons would include, but not be limited to, halogen, protected amine, nitrile, aldehyde, and the like. Following the Acylation/Sulfonylation reaction, these groups would then be unmasked or converted under standard conditions to afford the basic group.

Scheme 2b: Acylation/Sulfonylation Process

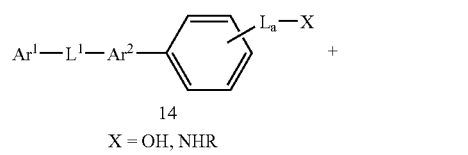

-continued

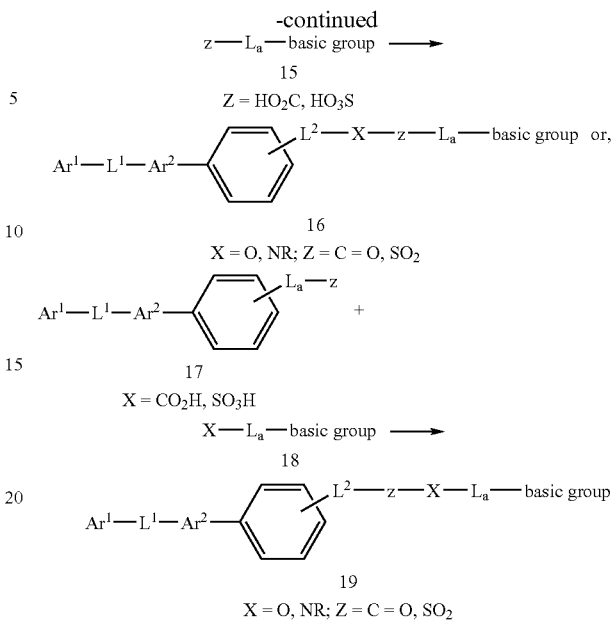

The carboxylic acid (or sulfonic acid) residue of compound 15 (or compound 17) is activated for coupling as a "reactive acylating agent." "Reactive acylating agents" are described in detail in Advanced Organic Chemistry, 4$^{th}$ Edition, Part B, Reactions and Synthesis, Francis A. Carey and Richard J. Sundberg, Kluwer Academic/Plenum Publishers, 2000, Chapter 3, and references cited therein. The "reactive acylating agent" can be formed and isolated, then reacted with the compound of Formula 14 (or 18), or formed in situ and reacted with the compound of Formula 14 (or 18), to form the compound of Formula 16 (or 19). One to five equivalents of the "reactive acylating agent" of compound 15 (or compound 17) and one to five equivalents of compound of Formula 14 (or 18) are reacted in an inert solvent. If necessary the reaction maybe carried out in the presence of one to five equivalents of 1-hydroxybenzotriazole, 1-hydroxy-7-azabenzotriazole, and/or a catalytic quantity to five equivalents of a base. The reaction is normally carried out between 0° C. and 120° C. Reaction time is normally 4 to 48 hours.

Examples of "reactive acylating agent" of compound 15 (or compound 17) include acid halides (e.g., acid chloride, acid bromide, and the like), mixed acid anhydrides (e. g., acid anhydrides with $C_1$–$C_6$ alkyl-carboxylic acid, $C_6$–$C_{10}$ aryl-carboxylic acid, and the like), activated esters (e. g., esters with phenol which may have substituents, 1-hydroxybenzotriazole, N-hydroxysuccinimide, 1-hydroxy-7-azabenzotriazole, and the like), thioesters (such as, 2-pyridinethiol, 2-imidazolethiol, and the like), N-acylimidazoles (e.g., imidazole, and the like), etc.

A "reactive acylation agent" may also be formed reacting the carboxylic acid (or sulfonic acid) residue of compound 15 (or compound 17) with a dehydration/condensation agent. Examples of a "dehydration/condensation agent" include dicyclohexylcarbodiimide (DCC), 1-ethyl-3-(3-dimethylaminopropyl)carbodiimide (EDCI), (2-ethoxy-1-ethoxycarbonyl-1,2-dihydroquinoline (EEDQ), and the like. Preferred solvents for the above reaction include acetonitrile, THF, and dichloromethane. Preferred bases for the above reaction include triethylamine, pyridine, and dimethylaminopyridine.

As outlined in Scheme 2c1, Scheme 2c2, and Scheme 2c3 below, the coupling process of General Method 2 can consist of a Urea/Thiourea/Guanidine/Carbamate-Type Coupling Process. The processes but not the compounds described are analogous to that described in U.S. Pat. Nos. 5,849,769 and 5,593,993, and references cited therein.

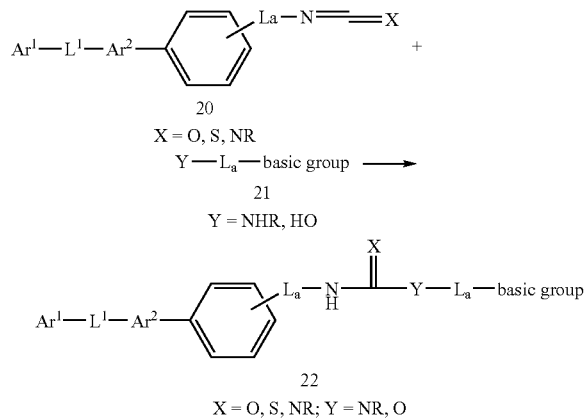

One to five equivalents of the isocyanate, isothiocyanate, or carbodiimide of Formula 20 and one to five equivalents of compound of Formula 21 are reacted in an inert solvent. The reaction is typically carried out between 0° C. and 150° C. Preferred reaction time is between 4 to 48 hours. Preferred solvents for the above reaction include acetonitrile, DMF, DMSO, THF, and dichloromethane.

If necessary, the reaction can be carried out with a basic group synthon incorporated as the basic group wherein a synthon is as described ealier. Following the Urea/Thiourea/Guanidine/Carbamate-Type Coupling Process, these groups would then be unmasked or converted under standard conditions to afford the basic group.

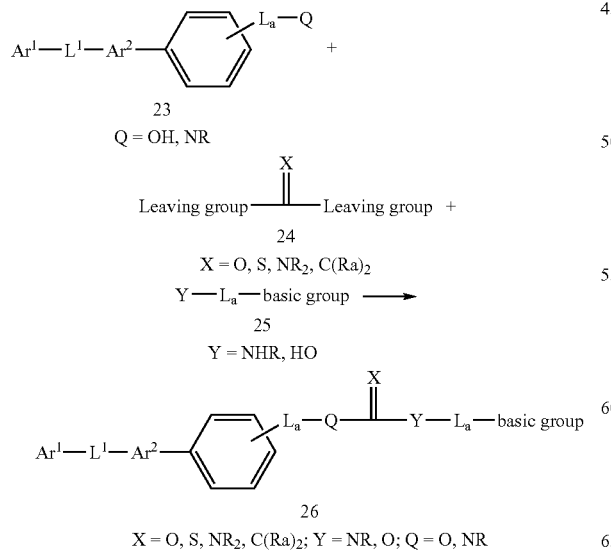

Approximately one equivalent of the compound of Formula 23 and one equivalent of compound of Formula 24 and one equivalent of the compound of Formula 25 are reacted in an inert solvent. The reaction is typically carried out between 0° C. and 150° C. Reaction time is normally 4 to 48 hours. The sequence of addition depends upon the reactivity of the individual reagents. The intermediate addition product may be isolated and subsequently be condensed with the second reagent. The reaction may or may not require the addition of a catalyst. Prefered solvents for the above reaction include acetonitrlle, DMF, DMSO, THF, toluene, isopropanol, and dichloromethane. Acids and bases as described previously may be used to catalyze the above reaction.

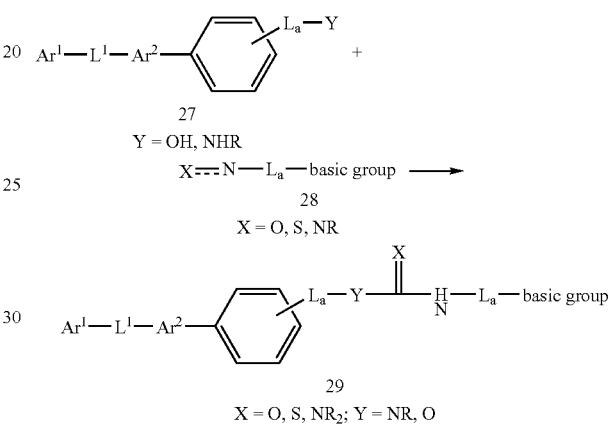

One to five equivalents of the isocyanate, isothiocyanate, carbodiimide of Formula 28 and one to five equivalents of compound of Formula 27 are reacted in an inert solvent. The reaction is normally carried out between 0° C. and 150° C. Reaction time is normally 4 to 48 hours.

As outlined in Schemes 2d below, the coupling process of General Method 2 may consist of an Organometallic Coupling Process.

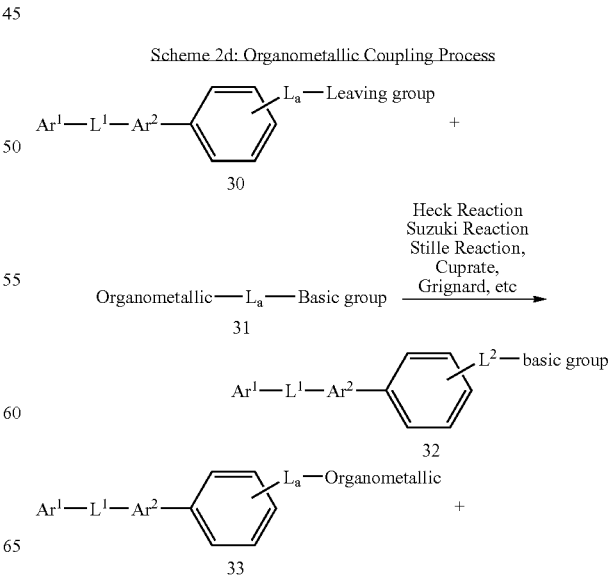

-continued

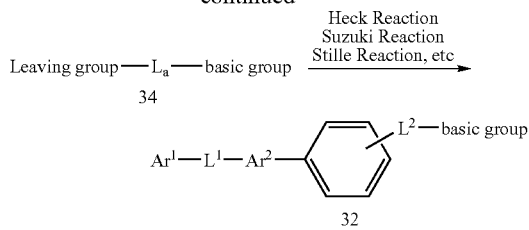

The compound of Formula 30 (or Formula 34) is coupled with an organometallic compound of Formula 31 (or Formula 33) (containing a basic group, or basic group precursor) in an Organometallic Coupling Process to afford the compounds of the invention of Formula 32.

"Organometallic Coupling Processes" include "palladium-catalyzed cross coupling reactions," such as, Heck-type coupling reactions, Suzuki-type coupling reactions and Stille-type coupling reactions. Other organometallic coupling reactions include, organocuprate coupling reactions, Grignard coupling reactions, and the like. A general description of Organometallic Coupling is given in detail in Advanced Organic Chemistry, $4^{th}$ Edition, Part B, Reactions and Synthesis, Francis A. Carey and Richard J. Sundberg, Kluwer Academic/Plenum Publishers, 2000, Chapters 7 and 8, and references cited therein.

In Scheme 2d. the compound of Formula 30 (or Formula 34) is coupled with the organometallic reagent of Formula 31 (or Formula 33) in the presence, or absence, of a transition metal catalyst, and/or a phosphine or arsine, and/or a base in an inert solvent. Other additives, such as, copper salts, silver salts, and the like may be added. Approximately one equivalent of the compound of Formula 30 (or Formula 34) is reacted with one to five equivalents of the compound of Formula 31 (or Formula 33) with the appropriate additives in an inert solvent. The reaction is normally carried out between −78° C. and 200° C. for between 1 to 72 hours. Analytical techniques known ot one of skill in the art are useful for determining completion of reaction.

Examples of "organometallic reagents" include, organomagnesium, organozinc, mixed-organocuprate, organostannane, or organoboron compounds, and the like.

Examples of "transition metal catalysts" include, palladium and nickel catalysts, such as, $Pd(OAc)_2$, $Pd(PPh_3)_4$, $PdCl_2$, $Pd(PPh_3)Cl_2$, $Pd(OCOCF_3)_2$, $(CH_3C_4H_5P)_2PdCl_2$, $[(CH_3CH_2)_3P]_2PdCl_2$, $[(C_6H_{11})_3P]_2PdCl_2$, $[(C_6H_5)_3P]_2PdBr_2$, $Ni(PPh_3)_4$, $(C_6H_4CH=CHCOCH=CHC_6H_5)_3Pd$, and the like.

Among the above transition metal catalysts, $Pd(OAc)_2$, $Ni(PPh_3)_4$, and $Pd(PPh_3)_4$ are preferable.

Examples of "phosphines or arsines" include, a trialkyl or triarylphosphine or arsine, such as triisopropylphosphine, triethylphosphine, tricyclopentylphosphine, triphenylphosphine, triphenylarsine, 2-furylphosphine, tri-o-tolylphosphine, tricyclohexylphosphine, 1,2-bis(diphenylphosphino)ethane, 1,3-bis(diphenylphosphino)propane, 1,4-bis(diphenylphosphino)butane, 2-(Di-t-butylphosphino)biphenyl, and the like.

Among the above "phosphines and arsines," triphenylphosphine, tri-o-tolylphosphine, triphenylarsine, and tricyclohexylphosphine are preferable.

Examples of "other additives" include, copper salts, zinc salts, lithium salts, ammonium salts and the like.

Among the above "other additives," CuI, LiCl, and $n\text{-}Bu_4N^+Cl^-$ are preferable. If necessary, the reaction can be carried out with a basic group synthon incorporated as the basic group as described previously.

As outlined in Schemes 2e below, the coupling process of General Method 2 can consist of a Wittig-type Coupling Process. The compound of Formula 33 (or Formula 37) is coupled with the phosphorus ylene (or ylide) reagent of Formula 34 (or Formula 36) to afford the compounds of Formula 35 of the invention. A general description of Wittig-type Coupling Reactions is given in detail in general reference texts such as Advanced Organic Chemistry, $4^{th}$ Edition, Part B, Reactions and Synthesis, Francis A. Carey and Richard J. Sundberg, Kluwer Academic/Plenum Publishers, 2000, Chapter 2, and references cited therein.

Scheme 2e: Wittig-type Couplings

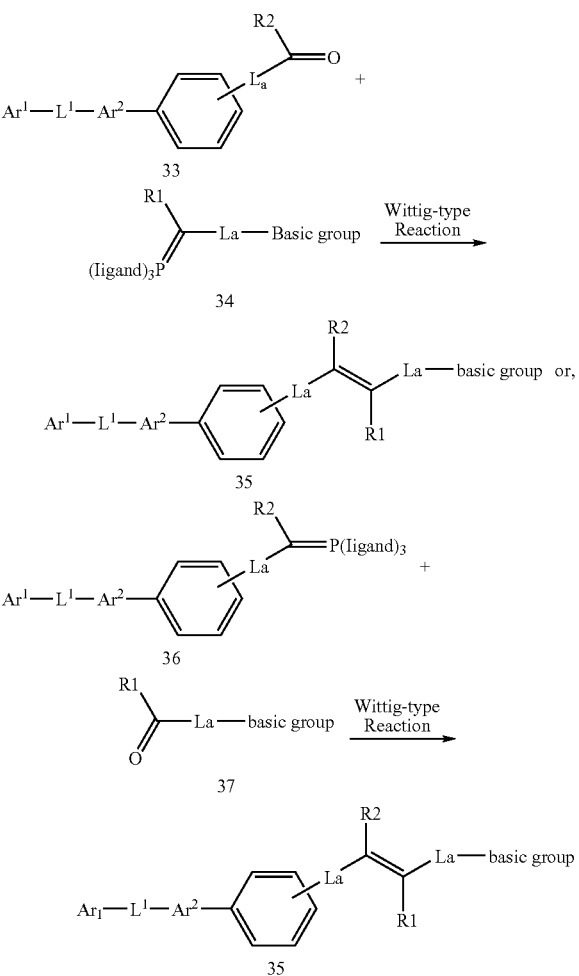

The compound of Formula 33 (or Formula 37) is coupled with the phosphorus ylene (or ylide) reagent of Formula 34 (or Formula 36) in the presence, or absence, of a base in an inert solvent to form the compounds of the invention i.e., Formula 35. Other additives, such as, lithium salts, sodium salts, potassium salts, and the like may be added. Approximately one to five equivalents of the compound of Formula 33 (or Formula 37) is reacted with one to five equivalents of the compound of Formula 34 (or Formula 36) with the appropriate additives in an inert solvent. The reaction is normally carried out between −78° C. and 120° C. for between 2 to 72 hours. The Wittig reaction product may be reduced to form other compounds of the invention using reducing agents known to one of skill in the art and/or described previously. Preferred bases for the above organometallic reactions include sodium hydride, DBU, potassium t-butoxide, and lithium hexamethyldisilazide.

General Method 3: Coupling of the $Ar^2$ and $Ar^3$ Groups

The compounds of Formula 3 can be prepared by the General Method 3, described in General Scheme 3, via coupling of the compounds of Formula 38 with a compound of Formula 39. An example of the General Method 3 is a Aryl Coupling Process (Scheme 3a). The aryl-coupling reaction is carried out in accordance with known methods, or analogous methods thereto, such as those described in the general reference texts discussed previously.

General Scheme 3: Aryl-Coupling Process

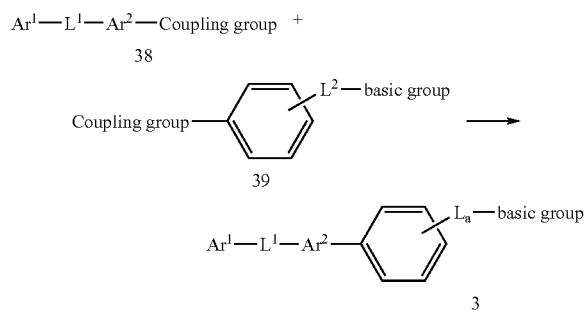

The compound of Formula 44 (or Formula 45) is coupled with an organometallic compound of Formula 43 (or Formula 46) in an Aryl Coupling Process to afford the compounds of the invention of Formula 3.

General Scheme 3a: Aryl Coupling

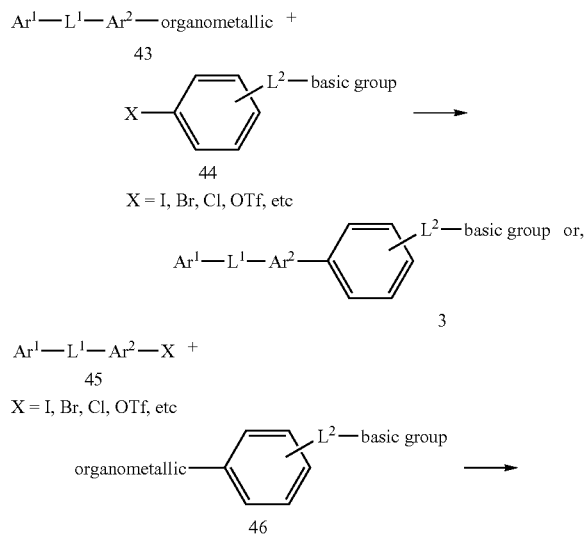

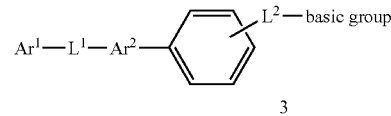

The compound of Formula 44 (or Formula 45) is coupled with the organometallic reagent of Formula 43 (or Formula 46) in the presence, or absence, of a transition metal catalyst, and (or) a phosphine or arsine, and (or) a base in an inert solvent. Other additives, such as, copper salts, silver salts, and the like may be added. Approximately one equivalent of the compound of Formula 44 (or Formula 45) is reacted with one to five equivalents of the compound of Formula 43 (or Formula 46) with the appropriate additives in an inert solvent. The reaction is normally carried out between −78° C. and 200° C. for between 1 to 72 hours. Examples of "organometallic reagents", "transition metal catalysts" "phosphines or arsines" "other additives" and "base" have been described previously.

General Method 4: Heterocycle Formation

The compounds of Formula 3 can be prepared by the General Method 4, described in General Scheme 4, via reaction of the compound of Formula 47 containing a coupling group with a compound of Formula 48 containing a coupling group, wherein during the course of the coupling reaction the coupling groups form the 6-membered ring heterocycle between the linker $L^1$ and the phenyl ring. $Ar^1$, $L^1$, $Ar^2$, $L^2$, and basic group are defined as above. Examples of heterocyclic ring forming reactions are given in Comprehensive Heterocyclic Chemistry, Volumes 1–8, A. P. Katritzky and C. W. Rees Eds, Pergamon Press, 1984; Heterocyclic Chemistry, $3^{rd}$ Ed, Thomas L. Gilchrist, Addison-Wesley-Longman Ltd, 1997; An Introduction to the Chemistry of Heterocyclic Compounds, $3^{rd}$ Ed, R. M. Acheson, Wiley Interscience, 1976; etc, and references cited therein. Specific examples of the General Method 4 include an Oxadiazole Process (Schemes 4a and 4b), a Thiadiazole Process (Scheme 4c), and an Oxazole Process (Scheme 6 a–e).

If necessary, the reaction can be carried out with a basic group synthon incorporated as the basic group, i.e., a group that could readily be converted to a basic group by methods known to one skilled in the art. Basic group synthons would include, but not be limited to, halogen, protected amine, nitrile, aldehyde, and the like. Following the Heterocycle Formation Process, these groups would then be unmasked or converted under standard conditions to afford the basic group.

General Scheme 4: Heterocycle Formation

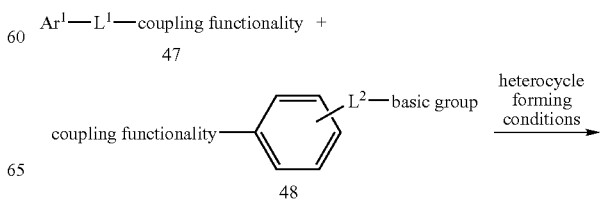

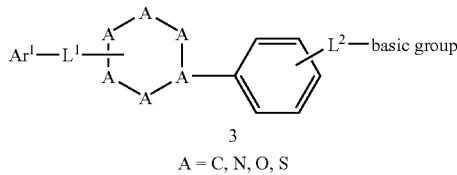

3

A = C, N, O, S

General Method 5: Coupling of Tile Linker Group L1

The compounds of Formula 3 can be prepared by the General Method 5, described in General Scheme 5, via reaction of the coupling group of Formula 49 with a coupling group of Formula 50, where during the course of the coupling reaction the coupling groups are retained, or lost, to form the linker $L^1$ between the 6-membered ring carbocyclic or heterocyclic group and $Ar^1$. $Ar^1$, $L^1$, $Ar^2$, $L^2$, and basic group are defined as above. La is defined as a group that when the coupling process occurs results in the formation of the linker $L^2$ defined above. Examples of the General Method 5 are an Ether/Thioether Alkylation Process (Scheme 5a), an Acylation/Sulfonylation Process Process (Scheme 5b), an Urea/Thiourea/Guanadine Coupling Process (Scheme 5c1, 5c2, 5c3), an Organometallic Process (Scheme 5d), and a Wittig-type Coupling (Scheme 5e).

If necessary, the reactions below may be carried out with a basic group synthon incorporated as the basic group, as described previously. Following the Coupling of the Linker Group ($L^1$) Process, these groups would then be unmasked or converted under standard conditions to afford the basic group.

General Scheme 5: Coupling of Linker Group $L^1$

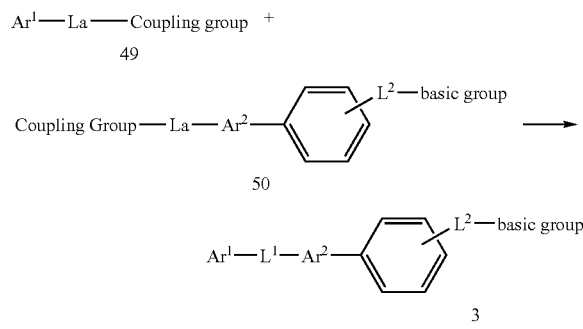

As outlined in Scheme 5a below, the coupling process of General Method 5 can consist of an Ether/Thioether Alkylation Process. Nucleophilic displacement by an alcohol or thiol-containing compound of Formula 51 (or Formula 55) with a compound of Formula 52 (or Formula 54) containing a leaving group affords the ether and thioether compounds of Formula 53 of the invention. The processes are analogous to the process described for the General Method 2, described in Scheme 2a, and carried out in accordance with the above method.

Scheme 5a: Ether/Thioether Alkylation Process

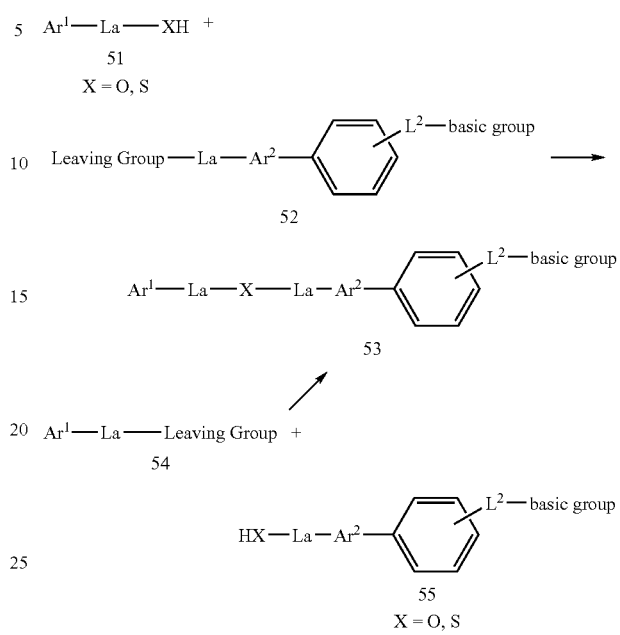

As outlined in Scheme 5b below, the coupling process of General Method 5 can consist of an Acylation/Sulfonylation Process. Acylation or sulfonylation of an alcohol or amine compound of Formula 57 with a carboxylic acid or sulfonic acid compound of Formula 56, affords the ester, amide, sulfonic ester, or sulfonamide compounds of Formula 58. Alternatively, acylation or sulfonylation of an alcohol or amine compound of Formula 59 with a carboxylic acid or sulfonic acid compound of Formula 60 affords the ester, amide, sulfonic ester, or sulfonamide compounds of Formula 61.

The processes are analogous to the process described for the General Method 2, described in Scheme 2b, and are carried out in accordance with the above method.

Scheme 5b: Acylation/Sulfonylation Process

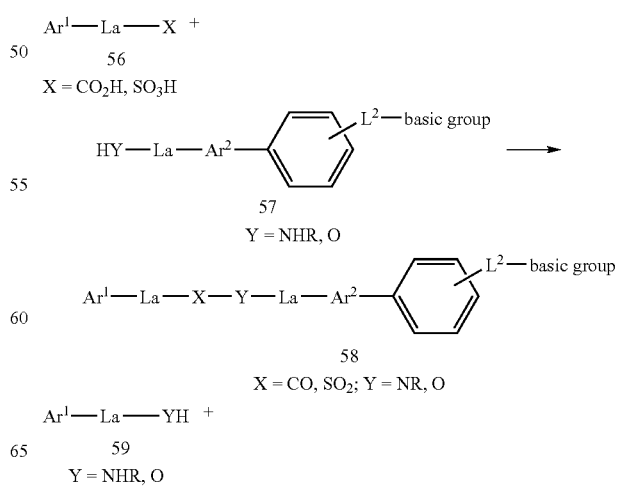

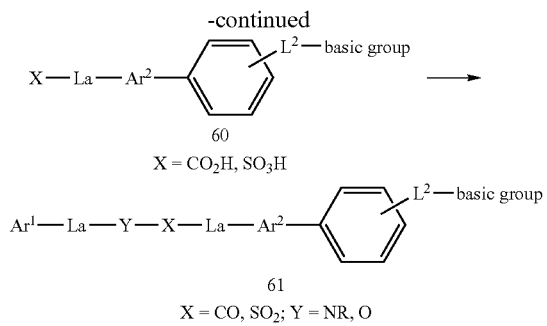

60
X = CO$_2$H, SO$_3$H

61
X = CO, SO$_2$; Y = NR, O

As outlined in Schemes 5c1, 5c2, and 5c3, below, the coupling process of General Method 5 can consist of a Urea/Thiourea/Guanidine/Carbamate-Type Coupling Process to afford the compounds of Formula 64, 68, and 71 of the invention. The processes are analogous to the processes described for the General Method 2, described in Schemes 2c1, 2c2, and 2c3, and are carried out in accordance with the above method.

Scheme 5c1: Urea/Thiourea/Guanidine/Carbamate-Type Coupling

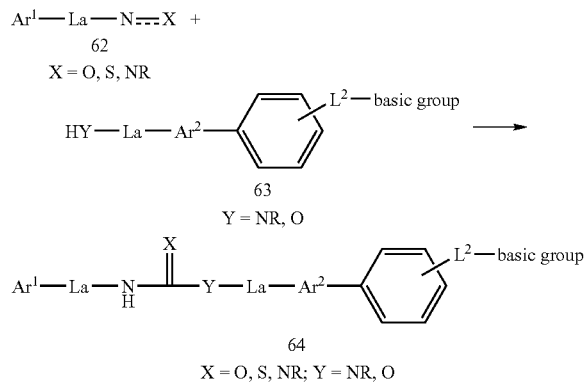

62
X = O, S, NR

63
Y = NR, O

64
X = O, S, NR; Y = NR, O

Scheme 5c2: Urea/Thiourea/Guanidine/Carbamate-Type Coupling

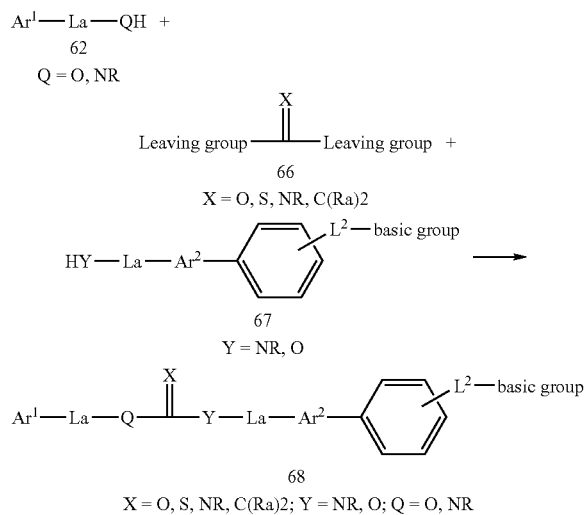

62
Q = O, NR

66
X = O, S, NR, C(Ra)$_2$

67
Y = NR, O

68
X = O, S, NR, C(Ra)$_2$; Y = NR, O; Q = O, NR

Scheme 5c3: Urea/Thiourea/Guanidine/Carbamate-Type Coupling

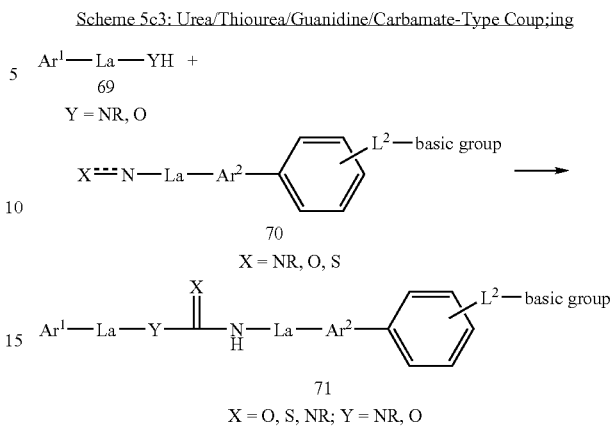

69
Y = NR, O

70
X = NR, O, S

71
X = O, S, NR; Y = NR, O

As outlined in Schemes 5d below, the coupling process of General Method 5 can consist of a Organometallic Coupling Process. The compound of Formula 73 (or Formula 74) is coupled with an organometallic compound of Formula 72 (or Formula 75) in an Organometallic Coupling Process to afford the compounds of Formula 3 of the invention. The processes are analogous to the processes described for the General Method 2, described in Scheme 2d, and are carried out in accordance with the above methods.

Scheme 5d: Organometallic Coupling Process

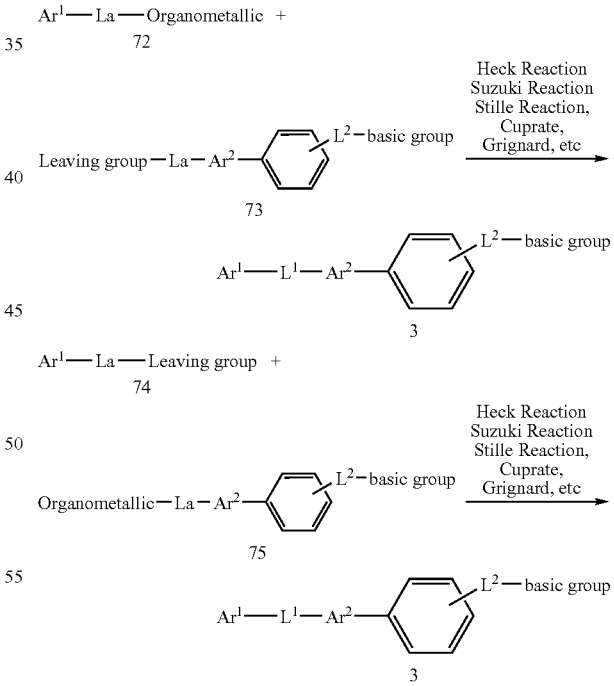

As outlined in Schemes 5e below, the coupling process of General Method 2 can consist of a Wittig-type Coupling Process. The compound of Formula 76 (or Formula 80) is coupled with the phosphorus ylene (or ylide) reagent of Formula 77 (Formula 79) to afford the compounds of Formula 78 of the invention. The processes are analogous to the processes described for the General Method 2, described in Scheme 2e, and are carried out in accordance with the above methods.

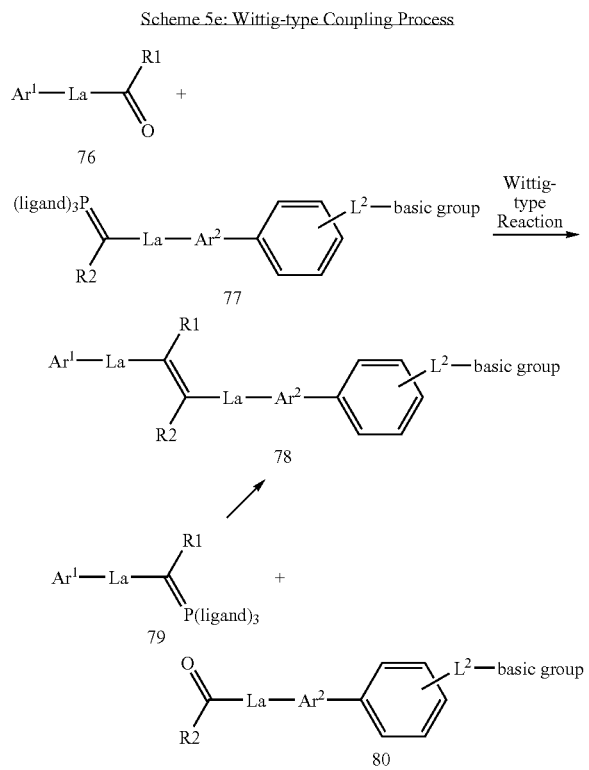

Scheme 5e: Wittig-type Coupling Process

Demonstration of Function

In order to demonstrate that compounds of the present invention have the capacity to bind to and inhibit the function of MCHR1, binding and functional assays were established. All ligands, radioligands, solvents and reagents employed in these assays are readily available from commercial sources or can be readily prepared by those skilled in the art.

The full-length cDNA for human MCHR1 was cloned from a human adult brain cDNA library (Edge Biosystems, Cat. 38356) by standard polymerase chain reaction (PCR) methodology employing the following primers: sense, 5'-GCCACCATGGACCT GGAAGCCTCGCTGC-3'; antisense, 5'-TGGTGCCCTGACTTGGAGGTGTGC-3'. The PCR reaction was performed in a final volume of 50 µL containing 5 µL of a 10× stock solution of PCR buffer, 1 µL of 10 mM dNTP mixture (200 µM final), 2 µL of 50 mM Mg(SO$_4$) (2 mM final), 0.5 µL of 20 µM solutions of each primer (0.2 µM final), 5 µL of template cDNA containing 0.5 ng DNA, 0.5 µL of Platinum Taq High Fidelity DNA polymerase (Gibco Life Technologies) and 36 µL of H$_2$O. PCR amplification was performed on a Perkin Elmer 9600 thermocycler. After denaturation for 90 sec at 94° C., the amplification sequence consisting of 94° C. for 25 sec, 55° C. for 25 sec and 72° C. for 2 min was repeated 30 times, followed by a final elongation step at 72° C. for 10 min. The desired PCR product (1.1 Kb) was confirmed by agarose gel electrophoresis and the band was extracted from the gel by Geneclean (Bio101) following the manufacturer's instructions. Following extraction, the cDNA fragment was cloned into pCR2.1-TOPO plasmid (Invitrogen) to confirm the identity and sequence.

In order to generate cell lines stably expressing MCHR1, the insert was then subcloned into the Xba I and Not I sites of pcDNA(+)-3.1-neomycin (Invitrogen). After purification by Qiagen Maxi-prep kit (QIAGEN, Inc.), the plasmid was transfected by Fugene 6 (Roche Applied Science) into AV12 cells that had been previously transfected with the promiscuous G protein $G_{\alpha 15}$. The transfected cells were selected by G418 (800 µg/mL) for 10–14 days and single colonies were isolated from culture plates. The G418-resistant colonies were further selected for MCHR1 expression by measuring MCH-stimulated Ca$^{2+}$ transients with a fluorometric imaging plate reader (FLIPR, Molecular Devices).

Typically, individual clones are plated out in 96-well plates at 60,000 cells per well in 100 µL of growth medium (Dulbecco's modified Eagle's medium (DMEM), 5% fetal bovine serum, 2 mM L-glutamine, 10 mM HEPES, 1 mM sodium pyruvate, 0.5 mg/ml Zeocin, and 0.5 mg/mL Geneticin). After 24 hrs at 37° C., medium is removed and replaced with 50 µL of dye loading buffer (Hank's balanced salt solution (HBSS) containing 25 mM HEPES, 0.04% Pluronate 127 and 8 µM Fluo3 Both from Molecular Probes)). After a 60 min loading period at room temperature, dye loading buffer is aspirated and replaced with 100 µL of HEPES/HBBS. Plate is placed in FLIPR and basal readings are taken for 10 sec, at which point 100 µL of buffer containing 2 µM MCH (1 µM final) is added and measurements are taken over 105 sec. To correct for variations between clones in numbers of cells per well, the MCH response is normalized to the response induced by epinephrine.

Both the $^{125}$I-MCH binding and functional GTPγ$^{35}$S binding assays employed membranes isolated from a clone designated as clone 43. Typically, cells from 20 confluent T225 flasks were processed by washing the monolayers in cold phosphate-buffered saline (PBS), scraping the cells into same and re-suspending the cell pellet in 35 mL of 250 mM Sucrose, 50 mM HEPES, pH 7.5, 1 mM MgCl$_2$, 24 µg/mL DNase I, and protease inhibitors (1 Complete® tablet, per 50 ml of buffer prepared, Roche Diagnostics). After incubation on ice for 5 min, cells were disrupted with 20–25 strokes of a Teflon/Glass homogenizer attached to an overhead motorized stirrer, and the homogenate was centrifuged at 40,000 rpm in Beckman Type 70.1 Ti rotor. The pellets were re-suspended in 250 mM Sucrose, 50 mM HEPES, pH 7.5, 1.5 mM CaCl$_2$, 1 mM MgSO$_4$ and protease inhibitors by Teflon/Glass homogenization to achieve a protein concentration of ~3–5 mg/ml (Pierce BCA assay with Bovine serum albumin as standard). Aliquots were stored at −70° C.

Binding of compounds to MCHR1 was assessed in a competitive binding assay employing $^{125}$I-MCH, compound and clone 43 membranes. Briefly, assays are carried out in 96-well Costar 3632 white opaque plates in a total volume of 200 µl containing 25 mM HEPES, pH 7.5, 10 mM CaCl$_2$, 2 mg/ml bovine serum albumin, 0.5% dimethyl sulfoxide (DMSO), 4 µg of clone 43 membranes, 100 pM $^{125}$I-MCH (NEN), 1.0 mg of wheat germ agglutinin scintillation proximity assay beads (WGA-SPA beads, Amersham) and a graded dose of test compound. Non-specific binding is assessed in the presence of 1 μM unlabeled MCH. Bound $^{125}$I-MCH is determined by placing sealed plates in a Microbeta Trilux (Wallac) and counting after a 5 hr delay.

$IC_{50}$ values (defined as the concentration of test compound required to reduce specific binding of $^{125}$I-MCH by 50%) are determined by fitting the concentration-response data to a 4-parameter model (max response, min response, Hill coefficient, $IC_{50}$) using Excel. $K_i$ values are calculated from $IC_{50}$ values using the Cheng-Prusoff approximation as described by Cheng et al. (Relationship between the inhibition constant ($K_i$) and the concentration of inhibitor which causes 50% inhibition ($IC_{50}$) of an enzymatic reaction, *Biochem. Pharmacol.*, 22: 3099–3108 (1973)). The $K_d$ for $^{125}$I-MCH is determined independently from a saturation binding isotherm.

Functional antagonism of MCH activity is assessed by measuring the ability of test compound to inhibit MCH-stimulated binding of GTPγ$^{35}$S to clone 43 membranes. Briefly, assays are carried out in Costar 3632 white opaque plates in a total volume of 200 μl containing 25 mM Hepes, pH 7.5, 5 mM MgCl$_2$, 10 μg/ml saponin, 100 mM NaCl, 3 μM GDP, 0.3 nM GTPγ$^{35}$S, 40 nM MCH (approximately equal to $EC_{90}$), 20 μg of clone 43 membranes, 1.0 mg of wheat germ agglutinin scintillation proximity assay beads (WGA-SPA beads, Amersham) and a graded dose of test compound. The plates are sealed and left for 16–18 hrs at 4° C. After a 1 hr delay to allow plates to equilibrate to ambient temperature, bound GTPγ$^{35}$S is determined by counting in a Microbeta Trilux (Wallac).

$IC_{50}$ values (defined as the concentration of test compound required to reduce MCH-stimulated GTPγ$^{35}$S binding by 50%) are determined by fitting the concentration-response data to a 4-parameter model (max response, min response, Hill coefficient, $IC_{50}$) using Excel. $K_b$ values are calculated from $IC_{50}$ values using a modification of the Cheng-Prusoff approximation as described by Leff and Dougal (Further concerns over Cheng-Prusoff analysis, *Trends Pharmacol. Sci.* 14: 110–112 (1993)) after verifying competitive antagonism by Schild analysis. The $EC_{50}$ for MCH alone is determined independently. The MCHR1 binding activities of representative examples of compounds of the invention (tested in duplicate) are shown in Table 1

TABLE 1

| Compound of Example # | MOLSTRUCTURE | MCHr Binding Ki (uM) |
|---|---|---|
| 1 | [structure with oxalate salt] | 5.04 |
| 4 | [structure] | 11.7 |
| 2 | [structure with oxalate salt] | 7.52 |

TABLE 1-continued

| Compound of Example # | MOLSTRUCTURE | MCHr Binding Ki (uM) |
|---|---|---|
| 24 | | 6.13 |
| 23 | | 7.2 |
| 6 | | 10.1 |
| 3 | | 10.67 |

TABLE 1-continued

| Compound of Example # | MOLSTRUCTURE | MCHr Binding Ki (uM) |
|---|---|---|
| 25 | | 6.89 |
| 14 | | 1.47 |
| 15 | | 1.95 |
| 4 | | 11.73 |
| 20 | | 11.37 |

TABLE 1-continued

| Compound of Example # | MOLSTRUCTURE | MCHr Binding Ki (uM) |
|---|---|---|
| 21 | | 8.55 |
| 22 | | 10.84 |
| 13 | | 8.76 |
| 16 | | 8.96 |
| 9 | | 16.3 |

Utilities

As an antagonist of the MCH receptor-1 binding, a compound of the present invention is useful in treating conditions in human and non-human animals in which the MCH receptor-1 has been demonstrated to play a role. The diseases, disorders or conditions for which compounds of the present invention are useful in treating or preventing include, but are not limited to, diabetes mellitus, hyperglycemia, obesity, hyperlipidemia, hypertriglyceridemia, hypercholesterolemia, atherosclerosis of coronary, cerebrovascular and peripheral arteries, gastrointestinal disorders including peptid ulcer, esophagitis, gastritis and duodenitis, (including that induced by H. pylori), intestinal ulcerations (including inflammatory bowel disease, ulcerative colitis, Crohn's disease and proctitis) and gastrointestinal ulcerations, neurogenic inflammation of airways, including cough, asthma, depression, prostate diseases such as benign prostate hyperplasia, irritable bowel syndrome and other disorders needing decreased gut motility, diabetic retinopathy, neuropathic bladder dysfunction, elevated intraocular pressure and glaucoma and non-specific diarrhea dumping syndrome. Compounds of the present invention have also shown some affinity for the R2 isoform of MCHR. In treating humans, the compounds of the present invetion are useful in treating and/or preventing obesity, excessive weight gain and diseases related to or exercerbated b excessive weight gain.

In treating non-human, non-companion animals, the compounds of the present invention are useful for reducing weight gain and/or improving the feed utilization efficiency and/or increasing lean body mass.

Formulation

The compound of formula I is preferably formulated in a unit dosage form prior to administration. Therefore, yet another embodiment of the present invention is a pharmaceutical formulation comprising a compound of formula I and a pharmaceutical carrier.

The present pharmaceutical formulations are prepared by known procedures using well-known and readily available ingredients. In making the formulations of the present invention, the active ingredient (compound of formula I) will usually be mixed with a carrier, or diluted by a carrier, or enclosed within a carrier which may be in the form of a liquid, tablet, capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders. Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by methods known to one of the art.

FORMULATION EXAMPLES

Formulation 1

Tablets

| Ingredient | Quantity (mg/tablet) |
|---|---|
| Active Ingredient | 5–500 |
| Cellulose, microcrystalline | 200–650 |
| Silicon dioxide, fumed | 10–650 |
| Stearate acid | 5–15 |

The components are blended and compressed to form tablets.

Formulation 2

Suspensions

| Ingredient | Quantity (mg/5 ml) |
|---|---|
| Active Ingredient | 5–500 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve (approximately 355 micron opening) and mixed with the sodium carboxymethyl cellulose and syrup to form a smooth paste. The benzoic acid solution, flavor, and color are diluted with some of the water and added, with stirring. Sufficient water is then added to produce the required volume.

Formulation 3

Intravenous Solution

| Ingredient | Quantity |
|---|---|
| Active Ingredient | 25 mg |
| Isotonic saline | 1,000 ml |

The solution of the above ingredients is intravenously administered to a patient at a rate of about 1 ml per minute.

Dose

The specific dose administered is determined by the particular circumstances surrounding each situation. These circumstances include but are not limited to, the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances, or by the veterinarian for non-human recipients.

Generally, an effective minimum daily dose of a compound of formula I is about 5, 10, 15, 40 or 60 mg. Typically, an effective maximum dose is about 500, 100, 60, 50, or 40 mg. Most typically, the dose ranges between 5 mg and 60 mg. The exact dose may be determined, in accordance with the standard practice in the medical arts of "dose titrating" the recipient; that is, initially administering a low dose of the compound, and gradually increasing the dose until the desired therapeutic effect is observed.

Route of Administration

The compounds may be administered by a variety of routes including the oral, rectal, transdermal, subcutaneous, topical, intravenous, intramuscular or intranasal routes.

Combination Therapy

A compound of formula I may be used in combination with other drugs or therapies that are used in the treatment/ prevention/suppression or amelioration of the diseases or conditions for which compounds of formula I are useful. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients that may be combined with a compound of formula I, and either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847;
  (ii) biguanides such as metformin and phenformin;
(b) insulin or insulin mimetics;
(c) sulfonylureas such as tolbutamide and glipizide;
(d) alpha-glucosidase inhibitors (such as acarbose);
(e) cholesterol lowering agents such as
  i. HMG-CoA reductase inhibitors (lovastatin, simvastatin and pravastatin, fluvastatin, atorvastatin, and other statins),
  ii. sequestrants (cholestyramine, colestipol and a dialkylaminoalkyl derivatives of a cross-linked dextran),
  iii. nicotinyl alcohol nicotinic acid or a salt thereof,
  iv. proliferator-activator receptor a agonists such as fenofibric acid derivatives (gemfibrozil, clofibrat, fenofibrate and benzafibrate),
  v. inhibitors of cholesterol absorption for example β-sitosterol and (acyl CoA:cholesterol acyltransferase) inhibitors for example melinamide,
  vi. probucol,
  vii. vitamin E, and
  viii. thyromimetics;
(f) PPARδ agonists such as those disclosed in WO97/28149;
(g) antiobesity compounds such as fenfluramine, dexfenfluramine, phentermine, sibutramine, orlistat, and other β3 adrenergic receptor agonists;
(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;
(i) PPARα agonists such as described in WO 97/36579 by Glaxo;
(j) PPARγ antagonists as described in WO97/10813; and
(k) serotonin reuptake inhibitors such as fluoxetine and sertraline.

Experimental

The following examples are only illustrative of the prepration protocols and Applicants' ability to prepare compounds of the present invention based on the schemes presented or modifications thereof. The examples are not intended to be exclusive or exhaustive of compounds made or obtainable.

General Preparations

Preparation of 4'-(2-phenoxy-ethylsulfanylmethyl)-biphenyl-3-carboxylic acid from 4-methylbenzeneboronic acid and ethyl 3-bromobenzoate

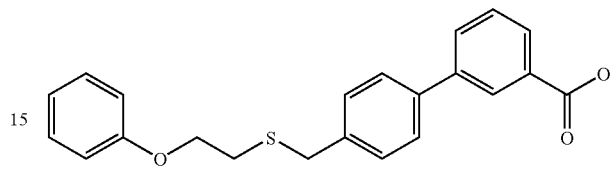

a) 4'-Methyl-biphenyl-3-carboxylic acid ethyl ester

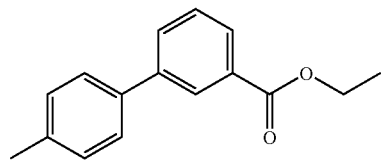

A solution of 4-methylbenzeneboronic acid (4.45 g, 32.75 mmol, 1.5 eq.) and ethyl 3-bromobenzoate (5.0 g, 21.83 mmol, 1 eq.) in THF (100 mL) was treated with 2M aqueous sodium carbonate (24 mL, 48.03 mmol, 2.2 eq.) followed by palladium(II) acetate (0.49 g, 2.18 mmol, 10 mol %), triphenylphosphine (2.52 g, 9.59 mmol, 4.4×Pd eq.), and copper(I) iodide (catalyst, 0.13 g, 0.68 mmol) as solids. The solution was then heated to 65° C. overnight.

The dark reaction was cooled and diluted with water and extracted 2×200 mL with EtOAc. The organic layers were combined, dried over MgSO$_4$, filtered, and the solvent removed in vacuo leaving a dark oil.

The oil was purified by preparative HPLC (Waters LC-2000) using a gradient starting with 100% hexane and going to 5% EtOAc in hexane over 30 minutes. Fractions containing the product were pooled and the solvent removed leaving 4'-methyl-biphenyl-3-carboxylic acid ethyl ester as a faint yellow oil (5.01 g, 95% yield).

$^1$H NMR (DMSO-d6) δ8.17 (m, 1H), 7.92 (m, 2H), 7.61 (m, 3H), 7.30 (d, 2H, J=8 Hz), 4.35 (q, 2H, 7 Hz), 2.36 (s, 3H), and 1.35 (t, 3H, J=7 Hz). IR (CHCl$_3$, cm$^{-1}$)1715, 1369, 1310, 1300, 1249, 1110. MS (ES$^+$)m/z 241. Anal. Calcd for C$_{16}$H$_{16}$O$_2$ C, 79.97; H, 6.71; N, 0.00. Found C, 79.84; H, 6.48; N, 0.14.

b 4'-Bromomethyl-biphenyl-3-carboxylic acid ethyl ester

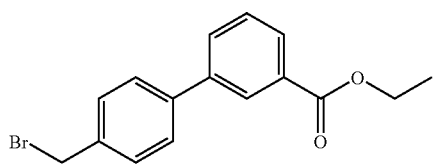

A solution of 4'-methyl-biphenyl-3-carboxylic acid ethyl ester (2.5 g, 10.4 mmol, 1 eq.) in CCl$_4$ (150 mL) was treated with N-bromosuccinimide (2.78 g, 15.6 mmol, 1.5 eq.) in a round bottom flask equipped with a stir bar, septum, and N$_2$ line with bubbler. The yellow solution was heated to 50° C.

with a heating mantle. After the temperature of the reaction had reached 50° C., 2,2'-azobisisobutyronitrile (0.17 g, 1.04 mmol, 10%) was added as a solid and the reaction heated to 76° C.

After 2 hours at 76° C., the reaction was diluted with water and the organic layer removed. The aqueous layer was extracted with CH₂Cl₂. The organic layers were combined, dried over MgSO₄, filtered, and the solvent removed in vacuo leaving a yellow oil.

The oil was purified by preparative HPLC (Waters LC-2000) using a gradient starting with 100% hexane and going to 10% EtOAc in hexane over 30 minutes. Fractions containing the product were pooled and the solvent removed in vacuo leaving 4'-bromomethyl-biphenyl-3-carboxylic acid ethyl ester as a yellow oil (3.11 g, 94% yield).

¹H NMR (DMSO-d6) δ 8.22–7.5 (m, 8H), 4.81 (s, 2H), 4.36 (q, 2H, J=7 Hz), 1.36 (t, 3H, J=7 Hz). MS (FD⁺) m/z 320, 318. Anal. Calcd for C₁₆H₁₅BrO₂ C, 60.21; H, 4.74; N, 0. Found C, 58.08; H, 4.47; N, 0.14.

c) 4'-(2-Hydroxy-ethylsulfanylmethyl)-biphenyl-3-carboxylic acid ethyl ester

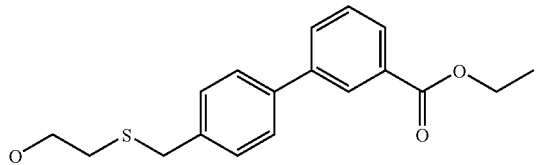

A solution of 4'-bromomethyl-biphenyl-3-carboxylic acid ethyl ester (3.05 g, 9.55 mmol, 1.02 eq.) in anhydrous DMF (50 mL) was treated with solid potassium carbonate (3.88 g, 28.08 mmol, 3 eq.) followed by 2-mercaptoethanol (0.73 g, 0.66 mL, 9.36 mmol, 1 eq.). The reaction was allowed to stir at room temperature overnight.

The reaction was diluted with water and extracted 2×100 mL with EtOAc. The organic layers were combined and washed with 50% brine. The organic layer was collected, dried over MgSO₄, filtered, and the solvent removed in vacuo leaving a yellow oil.

Purified the oil by preparative HPLC (Waters LC-2000) using a gradient starting with 5% EtOAc in hexane and going to 40% EtOAc in hexane over 30 minutes. Fractions containing the product were pooled and the solvent removed in vacuo leaving 4'-(2-hydroxy-ethylsulfanylmethyl)-biphenyl-3-carboxylic acid ethyl ester as a yellow oil (1.39 g, 47% yield).

¹H NMR (DMSO-d6) δ 8.18 (m, 1H), 7.95 (m, 2H), 7.65 (m, 3H), 7.44 (m, 2H), 4.79 (t, 1H, J=6 Hz), 4.35 (q, 2H, J=7 Hz), 3.82 (s, 2H), 3.54 (q, 2H, J=7 Hz), 2.51 (t, 2H, J=7 Hz), 1.35 (t, 3H, J=7 Hz). IR (CHCl₃, cm⁻¹) 3501, 3016, 1714, 1369, 1309, 1243, 1272, 1110, 1058, 1044. MS (FD₊) m/e 316. Anal. Calcd for C₁₈H₂₀O₃S C, 68.33; H, 6.37; N, 0. Found C, 66.76; H, 6.04; N, 0.19.

d) 4'-(2-Phenoxy-ethylsulfanylmethyl)-biphenyl-3-carboxylic acid ethyl ester

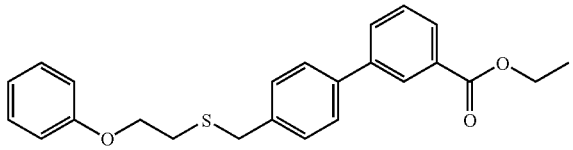

4'-(2-Hydroxy-ethylsulfanylmethyl)-biphenyl-3-carboxylic acid ethyl ester (1.35 g, 4.27 mmol, 1 eq.) was dissolved in anhydrous THF (50 mL) with triphenyphosphine (1.57 g, 5.98 mmol, 1.4 eq.) and phenol (0.56 g, 5.98 mmol, 1.4 eq.). To this solution, diisopropyl azidocarboxylate (1.21 g, 1.18 mL, 5.98 mmol, 1.4 eq.) was added dropwise via syringe over 5 minutes. After addition was complete, The reaction was stirred at room temperature for 2 hours and then at 50° C. for another hour.

The reaction was diluted with EtOAc and washed with 0.5M aqueous NaOH. The organic layer was collected, dried over MgSO₄, filtered, and the solvent removed in vacuo leaving a yellow oil.

The oil was purified via silica gel flash chromatography using 15% EtOAc in hexane as the mobile phase. Fractions containing the product were pooled and the solvent removed in vacuo leaving 4'-(2-phenoxy-ethylsulfanylmethyl)-biphenyl-3-carboxylic acid ethyl ester (1.23 g, 73% yield) as a yellow oil.

¹H NMR (DMSO-d6) δ 8.18 (m, 1H), 7.94 (m, 2H), 7.65 (m, 3H), 7.47 (d, 2H, J=8 Hz), 7.27 (m, 2H), 6.91 (m, 3H), 4.35 (q, 2H, J=7 Hz), 4.11 (t, 2H, J=7 Hz), 3.91 (s, 2H), 2.80 (t, 2H, J=7 Hz), 1.35 (t, 3H, J=7 Hz). IR (CHCl₃, cm₋₁) 1714, 1601, 1498, 1308, 1244, 1110. MS(FD⁺) m/e 392. Anal. Calcd for C₂₄H₂₄O₃S C, 73.44; H, 6.16; N, 0. Found C, 70.51; H, 6.03; N, 0.91.

e) 4'-(2-Phenoxy-ethylsulfanylmethyl)-biphenyl-3-carboxylic acid

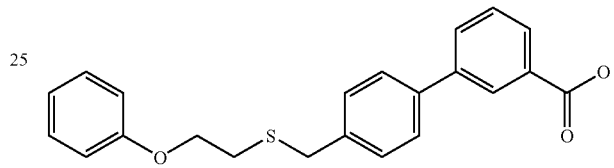

Dissolved 4'-(2-phenoxy-ethylsulfanylmethyl)-biphenyl-3-carboxylic acid ethyl ester (1.61 g, 4.10 mmol, 1 eq.) in 30% aqueous THF (25 mL) and treated with lithium hydroxide (0.29 g, 12.3 mmol, 3 eq.). The reaction was then stirred overnight at 60° C.

Diluted the reaction with water and acidified to pH 2 with 1 M HCl. Extracted the reaction with 2×150 mL Et₂O. The organic layers were combined, dried over MgSO₄, filtered, and the solvent removed in vacuo leaving 4'-(2-phenoxy-ethylsulfanylmethyl)-biphenyl-3-carboxylic acid (1.49 g, 100% yield) as abrown oil which crystallized on standing.

1H NMR (DMSO-d6) δ 13.12 (s, 1H), 8.18 (m, 1H), 7.92 (m, 2H), 7.62 (m, 3H), 7.43 (m, 2H), 7.25 (m, 2H), 6.91 (m, 3H), 4.12 (t, 2H, J=7 Hz), 3.95 (s, 2H), 2.81 (t, 2H, J=7 Hz). IR (CHCl₃, cm⁻¹) 3062, 2926, 2874, 2657, 1696, 1601, 1497, 1243, 1226, 1173, 1033. MS (ES⁻) m/e 363. Anal. Calcd for C₂₂H₂₀O₃S C, 72.50; H, 5.53; N, 0. Found C, 72.10; H, 5.54; N, 0.15.

Example 1

Preparation of 4'-(2-phenoxy-ethylsulfanylmethyl)-biphenyl-3-carboxylic acid(3-dimethylamino-propyl)-amide oxalate

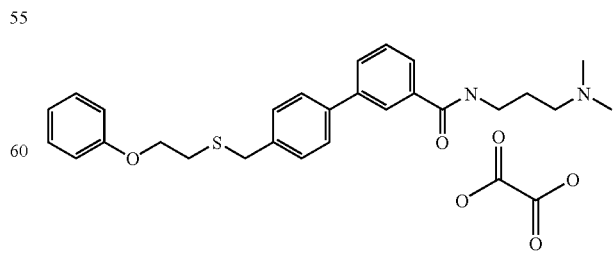

A solution of 4'-(2-phenoxy-ethylsulfanylmethyl)-biphenyl-3-carboxylic acid (0.91 g, 2.5 mmol, 1 eq.) in anhydrous THF (10 mL) was treated with 1,1'-carbonyldiimidazole (0.41 g, 2.55 mmol, 1.02 eq.) and the resulting solution heated to 60° C. for 25 minutes.

The solution was then allowed to cool and the 3-(dimethylamino)propylamine (0.31 g, 0.38 mL, 3 mmol, 1.2 eq.) was added via syringe. The reaction was allowed to stir at room temperature.

After 2 hours, the reaction was diluted with water and extracted with 2×150 mL EtOAc. The organic layers were combined, dried over MgSO$_4$, filtered, and the solvent removed in vacuo leaving 4'-(2-phenoxy-ethylsulfanylmethyl)-biphenyl-3-carboxylic acid (3-dimethylamino-propyl)-amide (0.97 g, 87% yield) as a yellow oil.

Dissolved 4'-(2-phenoxy-ethylsulfanylmethyl)-biphenyl-3-carboxylic acid(3-dimethylamino-propyl)-amide (0.48 g, 1.07 mmol, 1 eq.) in acetone (10 mL) and treated the solution dropwise with oxalic acid(0.12 g, 1.28 mmol, 1.2 eq.) in acetone (5 mL). Added Et$_2$O until cloudy and then placed in the freezer to induce crystallization. The resulting white solid was collected by filtration and washed with Et$_2$O to give 4'-(2-phenoxy-ethylsulfanylmethyl)-biphenyl-3-carboxylic acid(3-dimethylamino-propyl)-amide oxalate (0.2217 g).

$^1$H NMR (DMSO-d6) δ 8.74 (br t, 1H), 8.12 (s, 1H), 7.83 (m, 2H), 7.69 (d, 2H, J=8 Hz), 7.56 (t, 1H, J=8 Hz), 7.47 (d, 2H, J=8 Hz), 7.28 (t, 2H, J=8 Hz), 6.92 (m, 3H), 4.12 (t, 2H, J=7 Hz), 3.92 (s, 2H), 3.35 (br, 2H), 3.04 (br, 2H), 2.80 (t, 2H, J=7 Hz), 2.73 (s, 6H), 1.89 (br, 2H). IR (KBr, cm$^{-1}$) 3357, 3042, 1718, 1644, 1601, 1542, 1243. MS (ES$^+$) m/e 449. Analysis calcd for C$_{29}$H$_{34}$N$_2$O$_6$S C, 64.66; H, 6.36; N, 5.20. Found C, 64.11; H, 6.25; N, 5.20. Analytical HPLC 94.3%. MP 132–133.5° C.

Example 2

Preparation of 4'-(2-phenoxy-ethylsulfanylmethyl)-biphenyl-3-carboxylic acid (2-dimethylamino-ethyl)-amide oxalate

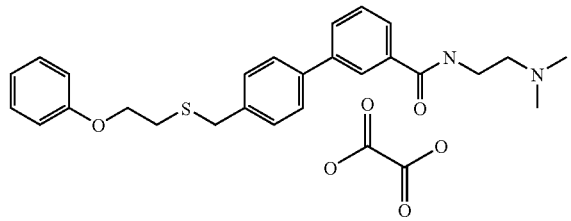

Prepared in the same manner as described for example 1. A solution of 4'-(2-phenoxy-ethylsulfanylmethyl)-biphenyl-3-carboxylic acid(0.68 g, 1.87 mmol, 1 eq.) was treated with 1,1'-carbonyldiimidazole (0.31 g, 1.91 mmol, 1.02 eq.) and warmed as described. The reaction was allowed to cool and then treated with N',N-dimethylethylenediamine (0.20 g, 2.24 mmol, 1.2 eq.). The reaction was treated as described in example 1 to give 4'-(2-phenoxy-ethylsulfanylmethyl)-biphenyl-3-carboxylic acid(2-dimethylamino-ethyl)-amide (0.76 g, 94% yield) as a faint yellow oil.

The free base was converted to the oxalate salt as described in example 1 using 0.20 g of oxalic acid giving 4'-(2-phenoxy-ethylsulfanylmethyl)-biphenyl-3-carboxylic acid (2-dimethylamino-ethyl)-amide oxalate (0.5584 g) as a white solid.

$^1$H NMR (DMSO-d6) δ 8.89 (br, 1H), 8.14 (s, 1H), 7.84–7.26 (m, 9H), 6.91 (m, 3H), 4.12 (t, 2H, J=7 Hz), 3.95 (s, 2H), 3.63 (br, 2H), 3.23 (br, 2H), 2.8 (m, 8H). IR (KBr, cm$^{-1}$) 3423, 3270, 1721, 1637, 1600, 1585, 1539, 1496, 1242, 756. MS (ES$^+$) m/e 435. MS (ES$^-$) m/e 433. Anal. Calcd for C$_{28}$H$_{32}$N$_2$O$_6$S C, 64.10; H, 6.15; N, 5.34. Found C, 62.70; H, 5.78; N, 5.06. Analytical HPLC 96.9% pure. MP 88–93° C.

Example 3

Preparation of 4'-(2-phenoxy-ethylsulfanylmethyl)-biphenyl-3-carboxylic acid (4-dimethylamino-butyl)-amide oxalate

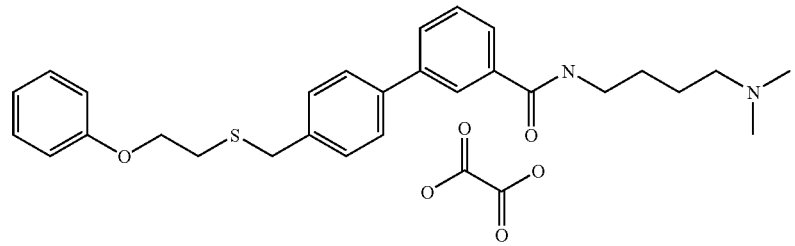

Prepared in the same manner as described for example 1. A solution of 4'-(2-phenoxy-ethylsulfanylmethyl)-biphenyl-3-carboxylic acid (0.71 g, 1.95 mmol, 1 eq.) was treated with 1,1'-carbonyldiimidazole (0.32 g, 1.99 mmol, 1.02 eq.) and warmed as described. The reaction was allowed to cool and then treated with 4-dimethylaminobutylamine (0.25 g, 2.15 mmol, 1.1 eq.). The reaction was treated as described in example 1 to give a faint yellow oil.

The oil was purified by silica gel chromatography by loading a CH$_2$Cl$_2$ solution of the amine onto the column and running 10% 2M NH$_3$ in MeOH in CHCl$_3$ as the mobile phase. Fractions containing the product were pooled and the solvent removed in vacuo leaving 4'-(2-phenoxy-ethylsulfanylmethyl)-biphenyl-3-carboxylic acid (4-dimethylamino-butyl)-amide (0.72 g, 71% yield) as a faint yellow oil.

The product was converted to the oxalate salt by adding solid oxalic acid (0.15 g) to an EtOAc solution of 4'-(2-phenoxy-ethylsulfanylmethyl)-biphenyl-3-carboxylic acid (4-dimethylamino-butyl)-amide giving 4'-(2-phenoxy-ethylsulfanylmethyl)-biphenyl-3-carboxylic acid (4-dimethylamino-butyl)-amide oxalate (0.4129 g) as a white solid.

$^1$H NMR (DMSO-d6) δ 8.66 (br, 1H), 8.10 (s, 1H), 7.81–7.25 (m, 9H), 6.91 (m, 3H), 4.12 (t, 2H, J=7 Hz), 3.94

(s, 2H), 3.31 (br, 2H), 3.03 (br, 2H), 2.81 (t, 2H, J=7 Hz), 2.72 (s, 6H), 1.61 (br, 4H). IR (KBr, cm$^{-1}$) 3348, 1718, 1703, 1638, 1600, 1585, 1539, 1240. MS (ES$^+$) m/e 463. MS (ES$^-$) m/e 461. Anal. Calcd for $C_{30}H_{36}N_2O_6S$ C, 65.2; H, 6.57; N, 5.07. Found C, 63.98; H, 6.60; N, 5.00. Analytical HPLC 98.1% purity. MP 144–147° C.

Preparation of 4'-(2-phenoxy-ethylsulfanylmethyl)-biphenyl-4-carboxylic acid from 4-methylbenzeneboronic acid and ethyl 4-iodobenzoate

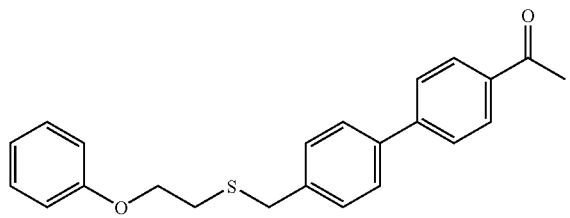

a) 4'-Methyl-biphenyl-4-carboxylic acid ethyl ester

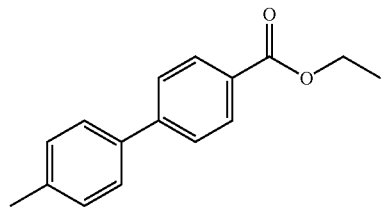

This compound was synthesized essentially as described for 4'-methyl-biphenyl-3-carboxylic acid ethyl ester. 4Methylbenzeneboronic acid (2.95 g, 21.73 mmol, 1.2 eq.) was combined with ethyl 4-iodobenzoate (5.0 g, 18.11 mmol, 1 eq.) in anhydrous THF (100 mL) as described. Treated this solution with 2M aqueous sodium carbonate (23.9 mL, 47.81 mmol, 2.2 eq.), palladium(II) acetate (0.49 g, 2.17 mmol, 10 mol %), triphenylphosphine (2.5 g, 9.55 mmol, 4.4×Pd), and copper(I) iodide (0.41 g, 2.17 mmol, 10%). The reaction was carried out and worked up as described for 4'-methyl-biphenyl-3-carboxylic acid ethyl ester to leave a dark oil.

The oil was purified by preparative HPLC (Waters LC-2000) as described for 4'-methyl-biphenyl-3-carboxylic acid ethyl ester leaving 4'-methyl-biphenyl-4-carboxylic acid ethyl ester as a white solid (3.66 g, 84% yield).

$^1$H NMR (DMSO-d6) δ 8.02 (d, 2H, J=9 Hz), 7.78 (d, 2H, J=9 Hz), 7.64 (d, 2H, J=8 Hz), 7.31 (d, 2H, J=8 Hz), 4.34 (q, 2H, J=7 Hz), 2.36 (s, 3H), 1.34 (t, 3H, J=7 Hz). IR (CHCl$_3$, cm$_{-1}$) 1712, 1609, 1292, 1279, 1112, 820. MS (ES$^+$) m/e 241. MS (ES$^-$) m/e 239. Anal. calcd. for $C_{16}H_{16}O_2$ C, 79.97; H, 6.71; N, 0. Found C, 79.83; H, 6.77; N, 0.16.

b) 4'-Bromomethyl-biphenyl-4-carboxylic acid ethyl ester

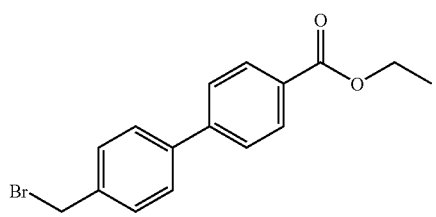

4'-Bromomethyl-biphenyl-4-carboxylic acid ethyl ester was prepared as described for 4'-bromomethyl-biphenyl-3-carboxylic acid ethyl ester. 4'-Methyl-biphenyl-4-carboxylic acid ethyl ester (3.4 g, 14.15 mmol, 1 eq.) was reacted with N-bromosuccinimide (3.27 g, 18.4 mmol, 1.3 eq.) and 2,2'-azobisisobutyronitrile (0.12 g, 0.71 mmol, 5 mol %) in carbon tetrachloride (150 mL). When complete, the reaction was worked up as described to produce 4'-bromomethyl-biphenyl-4-carboxylic acid ethyl ester (3.74 g, 83% yield) as a yellow solid.

$^1$H NMR (DMSO-d6) δ 8.04 (m, 2H), 7.84 (m, 2H), 7.74 (d, 2H, J=8 Hz), 7.57 (d, 2H, J=8 Hz), 4.78 (s, 2H), 4.34 (q, 2H, J=7 Hz), 1.34 (t, 3H, J=7 Hz). MS (ES+) m/e 319, 321.

c) 4'-(2-Hydroxy-ethylsulfanylmethyl)-biphenyl-4-carboxylic acid ethyl ester

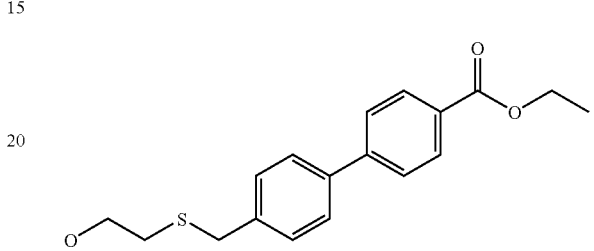

4'-(2-Hydroxy-ethylsulfanylmethyl)-biphenyl-4-carboxylic acid ethyl ester was prepared as described for 4'-(2-hydroxy-ethylsulfanylmethyl)-biphenyl-3-carboxylic acid ethyl ester. 4'-Bromomethyl-biphenyl-4-carboxylic acid ethyl ester (4.2 g, 13.16 mmol, 1 eq.) in anhydrous DMF (100 mL) was treated with potassium carbonate (5.46 g, 39.48 mmol, 3 eq.) and 2-mercaptoethanol (1.23 g, 15.79 mmol, 1.2 eq.). When the reaction was complete, the reaction was worked up as described leaving a yellow oil upon removal of the solvent.

The oil was purified via silica gel flash chromatography using a step gradient of EtOAc in hexanes as the mobile phase. Fractions containing the product were pooled and the solvent removed in vacuo leaving 4'-(2-hydroxy-ethylsulfanylmethyl)-biphenyl-4-carboxylic acid ethyl ester (2.41 g, 58% yield) as a white solid.

$^1$H NMR (DMSO-d6) δ 8.03 (d, 2H, J=8 Hz), 7.82 (d, 2H, J=8 Hz), 7.70 (d, 2H, J=8 Hz), 7.45 (d, 2H, J=8 Hz), 4.78 (t, 1H, J=6 Hz), 4.33 (q, 2H, J=7 Hz), 3.81 (s, 2H), 3.52 (q, 2H, J=7 Hz), 2.50 (br, 2H), 1.34 (t, 3H, J=7 Hz). IR (CHCl$_3$, cm$^{-1}$) 3599, 3506 (br), 1710, 1609, 1369, 1281, 1111, 1006. MS (FD)m/e 316. Anal. Calcd for $C_{18}H_{20}O_3S$ C, 68.33; H, 6.37; N, 0. Found C, 68.14; H, 6.32; N, 0.19.

d) 4'-(2-Phenoxy-ethylsulfanylmethyl)-biphenyl-4-carboxylic acid ethyl ester

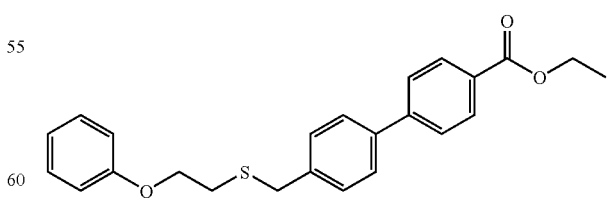

4'-(2-Phenoxy-ethylsulfanylmethyl)-biphenyl-4-carboxylic acid ethyl ester was prepared as described for 4'-(2-phenoxy-ethylsulfanylmethyl)-biphenyl-3-carboxylic acid ethyl ester. 4'-(2-Hydroxy-ethylsulfanylmethyl)-biphenyl-4-carboxylic acid ethyl ester (3.11 g, 9.83 mmol, 1 eq.) in anhydrous THF (100 mL) was treated with phenol (1.29 g, 13.76 mmol, 1.4 eq.), triphenylphosphine (3.61 g, 13.76 mmol, 1.4 eq.), and diisopropyl azidocarboxylate (2.78 g, 2.71 mL, 13.76 mmol, 1.4 eq.) as described. When the reaction was complete, the reaction was worked up and the product purified via silica gel flash chromatography leaving 4'-(2-phenoxy-ethylsulfanylmethyl)-biphenyl4-carboxylic acid ethyl ester (3.82 g, 99% yield) as a yellow oil.

$^1$H NMR (DMSO-d6) δ 8.03 (d, 2H, J=8 Hz), 7.82 (d, 2H, J=8 Hz), 7.70 (d, 2H, J=8 Hz), 7.48 (d, 2H, J=8 Hz), 7.27 (m, 2H), 6.93 (m, 3H), 4.33 (q, 2H, J=7 Hz), 4.11 (t, 2H, J=7 Hz), 3.91 (s, 2H), 2.80 (t, 2H, J=7 Hz), 1.34 (t, 3H, J=7 Hz). IR (CHCl$_3$, cm$^{-1}$) 1710, 1609, 1601, 1497, 1369, 1311, 1281, 1179, 1173, 1111, 1030, 1007. MS (FD) m/e 392. Anal. Calcd for $C_{24}H_{24}O_3S$ C, 73.44; H, 6.16; N, 0. Found C, 71.92; H, 6.15; N, 0.51.

e) 4'-(2-Phenoxy-ethylsulfanylmethyl)-biphenyl-4-carboxylic acid

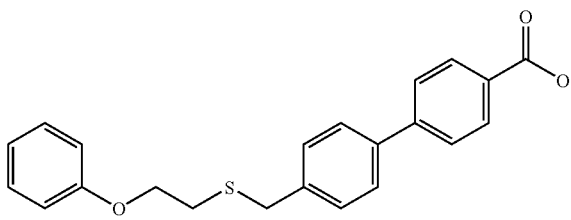

4'-(2-phenoxy-ethylsulfanylmethyl)-biphenyl-4-carboxylic acid was prepared as described for 4'-(2-phenoxy-ethylsulfanylmethyl)-biphenyl-3-carboxylic acid. 4'-(2-Phenoxy-ethylsulfanylmethyl)-biphenyl-4-carboxylic acid ethyl ester (3.75 g, 9.55 mmol, 1 eq.) in 30% aqueous THF was reacted with lithium hydroxide (0.69 g, 28.65 mmol, 3 eq.). When complete, the reaction was worked up as described leaving a light yellow solid which was recrystallized from acetone/diethyl ether to afford 4'-(2-phenoxy-ethylsulfanylmethyl)-biphenyl-4-carboxylic acid (2.28 g, 65% yield) as a light yellow solid.

$^1$H NMR (DMSO-d6) δ 12.9 (s, 1H), 8.02 (m, 2H), 7.76 (m, 4H), 7.47 (m, 2H), 7.29 (m, 2H), 6.94 (m, 3H), 4.11 (t, 2H, J=7 Hz), 3.91 (s, 2H), 2.80 (t, 2H, J=7 Hz). IR (KBr, cm$^{-1}$) 3411, 1685, 1676, 1603, 1608, 1497, 1427, 1302, 1290, 1246, 1234, 858, 776, 754. MS (ES$^-$) m/e 363. Analytical composition calculated for $C_{22}H_{20}O_3S$ C, 72.50; H, 5.53; N, 0. Found C, 73.95; H, 5.70; N, 0.21.

Example 4

Preparation of 4'-(2-phenoxy-ethylsulfanylmethyl)-biphenyl-4-carboxylic acid (2-dimethylamino-ethyl)-amide oxalate

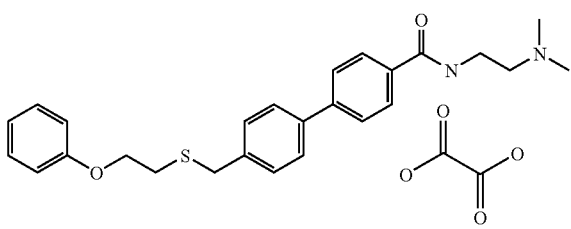

4'-(2-Phenoxy-ethylsulfanylmethyl)-biphenyl-4-carboxylic acid (2-dimethylamino-ethyl)-amide was prepared as described in example 1. 4'-(2-Phenoxy-ethylsulfanylmethyl)-biphenyl-4-carboxylic acid (0.8 g, 2.19 mmol, 1 eq.) in THF was treated with 1,1'-carbonyldiimidazole (0.36 g, 2.23 mmol, 1.02 eq.). The resulting acyl imidazole was then treated with N,N-dimethylethylenediamine (0.23 g, 2.63 mmol, 1.2 eq). When complete, the reaction was worked up and the resulting yellow oil purified as described in example 3 to give 4'-(2-phenoxy-ethylsulfanylmethyl)-biphenyl-4-carboxylic acid (2-dimethylamino-ethyl)-amide (0.82 g, 86% yield) as a yellow oil.

The free base was converted to the oxalate as by adding a solution of oxalic acid (0.20 g, 1.2 eq.) in EtOAc dropwise to an EtOAc solution of the amine giving 4'-(2-phenoxy-ethylsulfanylmethyl)-biphenyl-4-carboxylic acid (2-dimethylamino-ethyl)-amide oxalate (0.84 g) as a white solid.

$^1$H NMR (DMSO-d6) δ 8.78 (t, 1H, J=5 Hz), 7.96 (d, 2H, J=8 Hz), 7.78 (d, 2H, J=8 Hz), 7.70 (d, 2H, J=8 Hz), 7.46 (d, 2H, J=8 Hz), 7.27 (m, 2H), 6.93 (m, 3H), 4.12 (t, 2H, J=7 Hz), 3.91 (s, 2H), 3.62 (m, 2H), 3.21 (t, 2H, J=7 Hz), 2.79 (m, 8H). IR (KBr, cm$^{-1}$) 3436, 1718, 1654, 1605, 1534, 1494. MS (ES$^+$) m/e 435. Analytical composition calculated for $C_{28}H_{32}N_2O_6S$ C, 64.10; H, 6.15; N, 5.34. Found C, 62.91; H, 6.03; N, 5.26. Analytical HPLC 98.1% purity. MP 122–126° C.

Example 5

Preparation of 4'-(2-phenoxy-ethylsulfanylmethyl)-biphenyl4-carboxylic acid (3-dimethylamino-propyl)-amide hydrochloride

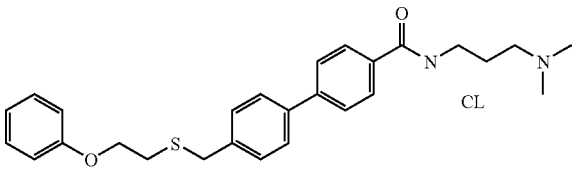

4'-(2-Phenoxy-ethylsulfanylmethyl)-biphenyl-4-carboxylic acid (3-dimethylamino-propyl)-amide was prepared as described in example 1. 4'-(2-Phenoxy-ethylsulfanylmethyl)-biphenyl-4-carboxylic acid (0.6 g, 1.65 mmol, 1 eq.) in THF was treated with 1,1'-carbonyldiimidazole (0.27 g, 1.68 mmol, 1.02 eq.). The resulting acyl imidazole was then treated with 3-(dimethylamino)propylamine (0.20 g, 1.98 mmol, 1.2 eq.). When complete, the reaction was worked up and the resulting yellow oil purified as described in example 3 to give 4'-(2-phenoxy-ethylsulfanylmethyl)-biphenyl4-carboxylic acid (3-dimethylamino-propyl)-amide (0.55 g, 74% yield) as a white solid.

The free base was converted to the hydrochloride salt by adding HCl (0.38 mL of 4 M HCl in 1,4-dioxane) dropwise to a CH$_2$Cl$_2$/Et$_2$O solution of the amine. Addition of more Et$_2$O with vigorous stirring produced 4'-(2-phenoxy-ethylsulfanylmethyl)-biphenyl-4-carboxylic acid (3-dimethylamino-propyl)-amide hydrochloride (0.43 g) as a yellow solid.

$^1$H NMR (DMSO-d6) δ 8.75 (t, 1H, J=5 Hz), 7.97 (d, 2H, J=8 Hz), 7.77 (d, 2H, J=8 Hz), 7.70 (d, 2H, J=8 Hz), 7.46 (d, 2H, J=8 Hz), 7.27 (m, 2H), 6.93 (m, 3H), 4.12 (t, 2H, J=7

Hz), 3.91 (s, 2H), 3.36 (m, 2H), 3.09 (m, 2H), 2.80 (t, 2H, J=7 Hz), 2.75 (s, 6H), 1.93 (m, 2H). IR (KBr, cm$^{-1}$) 3432, 3311, 1652, 1601, 1540, 1495, 1303, 1242. MS (ES$^+$) m/e 449. MS (ES$^-$) m/e 447. Analytical composition calculated for $C_{27}H_{33}ClN_2O_2S$ C, 66.85; H, 6.86; N, 5.77. Found C, 66.06; H, 6.69; N, 5.84. Analytical HPLC 100% purity. MP 112–115° C.

Example 6

Preparation of 4'-(2-phenoxy-ethylsulfanylmethyl)-biphenyl-4-carboxylic acid (4-dimethylamino-butyl)-amide oxalate

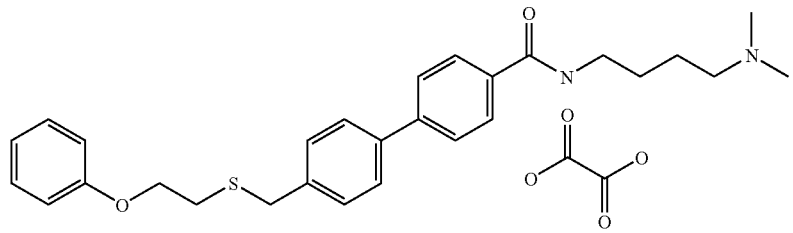

4'-(2-Phenoxy-ethylsulfanylmethyl)-biphenyl-4-carboxylic acid (4-dimethylamino-butyl)-amide was prepared as described in example 1. 4'-(2-Phenoxy-ethylsulfanylmethyl)-biphenyl-4-carboxylic acid (0.8 g, 2.19 mmol, 1 eq.) in THF was treated with 1,1'-carbonyldiimidazole (0.36 g, 2.23 mmol, 1.02 eq.). The resulting acyl imidazole was then treated with 4-dimethylaminobutylamine (0.28 g, 2.41 mmol, 1.1 eq.). When complete, the reaction was worked up to leave a yellow oil (0.72 g, 71% yield) which solidified on standing. The free base was converted to the oxalate as described in example 3 to give 4'-(2-phenoxy-ethylsulfanylmethyl)-biphenyl-4-carboxylic acid (4-dimethylamino-butyl)-amide oxalate (0.61 g) as a white solid.

$^1$H NMR (DMSO-d6) δ 8.78 (t, 1H, J=5 Hz), 7.93 (d, 2H, J=8 Hz), 7.76 (d, 2H, J=8 Hz), 7.69 (d, 2H, J=8 Hz), 7.46 (d, 2H, J=8 Hz), 7.27 (m, 2H), 6.93 (m, 3H), 4.12 (t, 2H, J=7 Hz), 3.91 (s, 2H), 3.30 (m, 2H), 3.05 (m, 2H), 2.80 (t, 2H, J=7 Hz), 2.74 (s, 6H), 1.61 (m, 4H). IR (KBr, cm$^{-1}$) 3314, 2945, 2702, 1719, 1703, 1631, 1610, 1601, 1495. MS (ES$^+$) m/e 463. MS (ES$^-$) m/e 461. Analytical composition calculated for $C_{30}H_{36}N_2O_6S$ C, 65.20; H, 6.57; N, 5.07. Found C, 63.48; H, 6.40; N, 5.67. Analytical HPLC 98.3% purity. MP 142–147° C.

Preparation of 4'-(2-phenoxy-ethylsulfanylmethyl)-biphenyl-2-carboxylic acid from 4-methylbenzeneboronic acid and ethyl 2-bromobenzoate

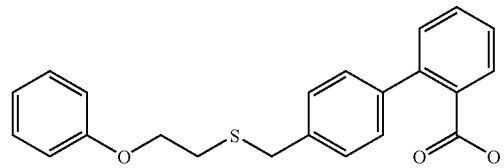

a) 4'-Methyl-biphenyl-2-carboxylic acid ethyl ester

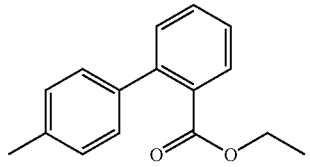

4'-Methyl-biphenyl-2-carboxylic acid ethyl ester was prepared in a similar fashion to 4'-methyl-biphenyl-3-carboxylic acid ethyl ester as described. Ethyl 2-bromobenzoate (5.0 g, 21.83 mmol, 1 eq.) and 4-methylbenzeneboronic acid (3.12 g, 22.92 mmol, 1.05 eq.) in THF and aqueous 2M sodium carbonate (24 mL, 2.2 eq.) were treated with palladium(II) acetate (0.49 g, 2.18 mmol, 10 mol %), triphenylphosphine (2.52 g, 9.59 mmol, 4.4×Pd), and copper(I) iodide (0.14 g). When complete, the reaction was worked up as described leaving an orange oil, which was purified, via silica gel flash chromatography using a step gradient of EtOAc in hexane as the mobile phase. Fractions containing the product were pooled leaving 4'-methyl-biphenyl-2-carboxylic acid ethyl ester (5.24 g, 99% yield) as a yellow oil.

$^1$H NMR (DMSO-d6) δ 7.76–7.34 (m, 5H), 7.20 (m, 3H), 4.32 and 4.04 (quartets, 2H total, J=7 Hz, atropisomerism of ester), 2.35 (s, 3H), 1.32 and 0.98 (triplets, 3H total, J=7 Hz, atropisomerism of ester). IR (CHCl$_3$, cm$^{-1}$) 2985, 1717, 1590, 1446, 1434, 1368, 1292, 1252, 1135, 1110, 1091, 1030. MS (ES$^+$) m/e 241.

b) 4'-Bromomethyl-biphenyl-2-carboxylic acid ethyl ester

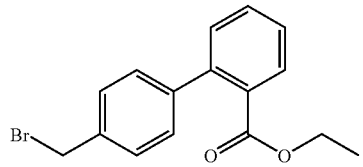

4'-Bromomethyl-biphenyl-2-carboxylic acid ethyl ester was prepared in a similar fashion to 4'-bromomethyl-biphenyl-3-carboxylic acid ethyl ester as described. 4'-Methyl-biphenyl-2-carboxylic acid ethyl ester (5.58 g, 23.22 mmol, 1 eq.) in carbon tetrachloride was treated with N-bromosuccinimide (4.96 g, 27.86 mmol, 1.2 eq.) and 2,2'-azobisisobutyronitrile (0.19 g, 1.16 mmol, 5 mol %). When complete, the reaction was worked up as described to give a yellow oil. The oil was purified by silica gel flash chromatography using 5% EtOAc in hexane as the mobile phase. Fractions containing the product were pooled and the solvent removed in vacuo to give 4'-bromomethyl-biphenyl-2-carboxylic acid ethyl ester (7.32 g, 99% yield) as a yellow oil.

¹H NMR (DMSO-d6) δ 7.75 (m, 1H), 7.65 (m, 2H), 7.49 (m, 3H), 7.32 (m, 2H), 4.77 (s, 2H), 4.32 and 4.02 (quartets, 2H, J=7 Hz, atropisomerism of ester), 1.32 and 0.92 (triplets, 3H, J=7 Hz, atropisomerism of ester). IR (CHCl₃, cm⁻¹) 1716, 1592, 1447, 1367, 1290, 1252, 1135. MS (ES⁺) m/e 319/321 and 239 (M−Br)⁺. Analytical composition calculated for C₁₆H₁₅BrO₂ C, 60.21; H, 4.74; N, 0. Found C, 50.23; H, 3.75; N, 0.22.

c) 4'-(2-Hydroxy-ethylsulfanylmethyl)-biphenyl-2-carboxylic acid ethyl ester

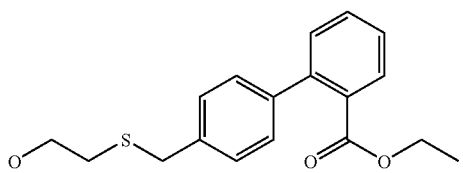

4'-(2-Hydroxy-ethylsulfanylmethyl)-biphenyl-2-carboxylic acid ethyl ester was prepared as described for 4'-(2-hydroxy-ethylsulfanylmethyl)-biphenyl-3-carboxylic acid ethyl ester. 4'-Bromomethyl-biphenyl-2-carboxylic acid ethyl ester (4.1 g, 12.84 mmol, 1 eq.) in anhydrous DMF was treated with 2-mercaptoethanol (1.2 g, 15.41 mmol, 1.2 eq.) and potassium carbonate (5.32 g, 38.52 mmol, 3 eq.). When complete, the reaction was worked up and purified as described for 4'-(2-hydroxy-ethylsulfanylmethyl)-biphenyl4-carboxylic acid ethyl ester to leave 4'-(2-hydroxy-ethylsulfanylmethyl)-biphenyl-2-carboxylic acid ethyl ester (3.05 g, 42% yield) as a light yellow oil.

¹H NMR (DMSO-d6) δ 37.72 (m, 1H), 7.61 (m, 1H), 7.45 (m, 2H), 7.36 (d, 2H, J=8 Hz), 7.23 (d, 2H, J=8 Hz), 4.80 (t, 1H, J=5 Hz), 4.02 (q, 2H, J=7 Hz), 3.80 (s, 2H), 3.55 (m, 2H), 2.52 (t, 2H, J=7 Hz), 0.95 (t, 3H, J=7 Hz). IR (CHCl₃, cm⁻¹) 3631, 3464, 2944 2839, 1712, 1601, 1289, 1245, 1016. MS (FD⁺) m/e 316.

d) 4'-(2-Phenoxy-ethylsulfanylmethyl)-biphenyl-2-carboxylic acid ethyl ester

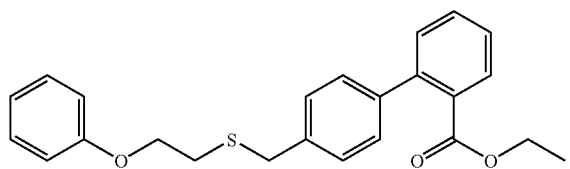

4'-(2-Phenoxy-ethylsulfanylmethyl)-biphenyl-2-carboxylic acid ethyl ester was prepared as described for 4'-(2-phenoxy-ethylsulfanylmethyl)-biphenyl-3-carboxylic acid ethyl ester. 4'-(2-hydroxy-ethylsulfanylmethyl)-biphenyl-2-carboxylic acid ethyl ester (1.65 g, 5.21 mmol, 1 eq.) was treated with phenol (0.69 g, 7.29 mmol, 1.4 eq.), triphenylphosphine (1.91 g, 7.29 mmol, 1.4 eq.), and diisopropyl azidocarboxylate (1.47 g, 1.44 mL, 7.29 mmol, 1.4 eq.). When complete, the reaction was worked up and the product purified by silica gel flash chromatography using 7.5% EtOAc in hexane as the mobile phase. Fractions containing the product were pooled and the solvent removed in vacuo leaving 4'-(2-phenoxy-ethylsulfanylmethyl)-biphenyl-2-carboxylic acid ethyl ester (1.40 g, 68% yield) as a yellow oil.

¹H NMR (DMSO-d6) δ 7.72 (m, 1H), 7.60 (m, 1H), 7.42 (m, 4H), 7.26 (m, 4H), 6.93 (m, 3H), 4.13 (t, 2H, J=7 Hz), 4.01 (q, 2H, J=7 Hz), 3.90 (s, 2H), 2.80 (t, 2H, J=7 Hz), 0.94 (t, 3H, J=7 Hz). IR (CHCl₃, cm⁻¹) 1712, 1600, 1498, 1288, 1244. MS (FD⁺) m/e 392. Analytical composition calculated for C₂₄H₂₄O₃S C, 73.44; H, 6.16; N, 0. Found C, 72.61; H, 5.78; N, 0.20.

e) 4'-(2-Phenoxy-ethylsulfanylmethyl)-biphenyl-2-carboxylic acid

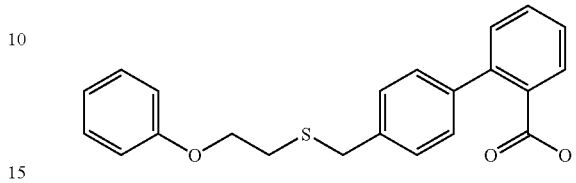

4'-(2-Phenoxy-ethylsulfanylmethyl)-biphenyl-2-carboxylic acid was prepared as described for 4'-(2-phenoxy-ethylsulfanylmethyl)-biphenyl-3-carboxylic acid. 4'-(2-Phenoxy-ethylsulfanylmethyl)-biphenyl-2-carboxylic acid ethyl ester (1.6 g, 4.08 mmol, 1 eq.) in 30% aqueous THF was treated with lithium hydroxide (0.29 g, 12.24 mmol, 3 eq.). When complete, the reaction was worked up as described and the resulting oil purified via silica gel flash chromatography using 50% EtOAc in hexane as the mobile phase. Fractions containing the product were pooled and the solvent removed in vacuo leaving 4'-(2-phenoxy-ethylsulfanylmethyl)-biphenyl-2-carboxylic acid (1.44 g, 97% yield) as an orange oil.

¹H NMR (DMSO-d6) δ 12.68 (s, 1H), 7.71 (m, 1H), 7.56 (m, 1H), 7.42 (m, 4H), 7.29 (m, 4H), 6.93 (m, 3H), 4.12 (t, 2H, J=7 Hz), 3.90 (s, 2H), 2.82 (t, 2H, J=7 Hz). IR (CHCl₃, cm⁻¹) 1701, 1600, 1498, 1484, 1290, 1244. MS (ES⁺) m/e 382 [M+NH₄]⁺. MS (ES⁺) m/e 363.

Example 7

Preparation of 4'-(2-phenoxy-ethylsulfanylmethyl)-biphenyl-2-carboxylic acid (2-dimethylamino-ethyl)-amide oxalate

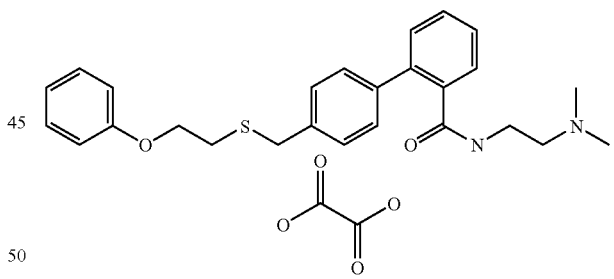

Prepared in the same manner as described for example 1. A solution of 4'-(2-phenoxy-ethylsulfanylmethyl)-biphenyl-2-carboxylic acid (0.70 g, 1.92 mmol, 1 eq.) in anhydrous THF was treated with 1,1'-carbonyldiimidazole (0.32 g, 1.96 mmol, 1.02 eq.) and warmed as described. The reaction was allowed to cool and then treated with N,N-dimethylethylenediamine (0.20 g, 2.35 mmol, 1.2 eq.). The reaction was treated as described in example 1 to give a yellow oil. The oil was purified by silica gel flash chromatography using 5% 2M NH₃ in methanol in chloroform as the mobile phase. Fractions containing the product were pooled and the solvent removed in vacuo leaving 4'-(2-phenoxy-ethylsulfanylmethyl)-biphenyl-2-carboxylic acid (2-dimethylamino-ethyl)-amide (0.50 g, 60% yield) as a bright yellow oil.

The free base was converted to the oxalate salt by adding 0.11 g (1.1 eq.) of oxalic acid to an EtOAc/Et₂O solution of the amine. After stirring for 1.5 hours, 4'-(2-phenoxy-ethyl-sulfanylmethyl)-biphenyl-2-carboxylic acid (2-dimethylamino-ethyl)-amide oxalate (0.3396 g) was obtained by filtration as a white solid.

$^1$H NMR (DMSO-d6) δ 8.37 (t, 1H, J=5 Hz), 7.44 (m, 10H), 6.94 (m, 3H), 4.13 (t, 2H, J=7 Hz), 3.90 (s, 2H), 3.37 (m, 2H), 2.93 (t, 2H, J=7 Hz), 2.83 (t, 2H, J=7 Hz), 2.65 (s, 6H). IR (KBr, cm$^{-1}$)3382, 1730, 1648, 1599, 1585, 1513, 1498, 1463, 1237, 1172, 1032, 1015, 752, 695. MS (ES$^+$) m/e 435. MS (ES$^-$) m/e 493 [M+OAc]−, 433. Analytical composition calculated for $C_{28}H_{32}N_2O_6S$ C, 64.10; H, 6.15; N, 5.34. Found C, 63.08; H, 5.52; N, 5.03. Analytical HPLC 96.9% purity. MP 109–113° C.

Example 8

Preparation of 4'-(2-phenoxy-ethylsulfanylmethyl)-biphenyl-2-carboxylic acid (3-dimethylamino-propyl)-amide

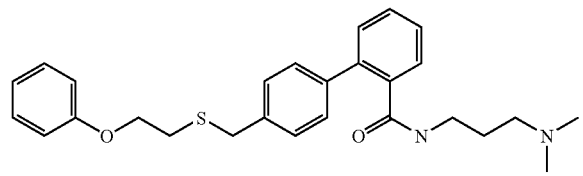

Prepared in the same manner as described for example 1. A solution of 4'-(2-phenoxy-ethylsulfanylmethyl)-biphenyl-2-carboxylic acid (0.38 g, 1.04 mmol, 1 eq.) in anhydrous THF was treated with 1,1'-carbonyldiimidazole (0.17 g, 1.06 mmol, 1.02 eq.) and warmed as described. The reaction was allowed to cool and then treated with 3-(dimethylamino)propylamine (0.13 g, 1.25 mmol, 1.2 eq.). The reaction was treated as described in example 1 to give a yellow oil. The oil was purified by silica gel flash chromatography using 10% 2M NH$_3$ in methanol in diethyl ether as the mobile phase. Fractions containing the product were pooled and the solvent removed in vacuo leaving 4'-(2-phenoxy-ethylsulfanylmethyl)-biphenyl-2-carboxylic acid (3-dimethylamino-propyl)-amide (0.40 g, 85% yield) as a light yellow oil.

$^1$H NMR (DMSO-d6) δ 8.05 (t, 1H, J=5 Hz), 7.38 (m, 10H), 6.93 (m, 3H), 4.12 (t, 2H, J=7 Hz), 3.88 (s, 2H), 3.05 (m, 2H), 2.81 (t, 2H, J=7 Hz), 2.04 (m, 8H), 1.39 (m, 2H). IR (CHCl$_3$, cm$^{-1}$) 3439, 3007, 2949, 2865, 2824, 2780, 1649, 1601, 1498, 1243. MS (ES$^+$) m/e 449. MS(ES$^-$) m/e 447. Analytical composition calculated for $C_{27}H_{32}N_2O_2S$ C, 72.29; H, 7.19; N, 6.24. Found C, 71.88; H, 7.27; N, 6.44. Analytical HPLC 100% purity.

Example 9

Preparation of 4'-(2-phenoxy-ethylsulfanylmethyl)-biphenyl-2-carboxylic acid (4-dimethylamino-butyl)-amide oxalate

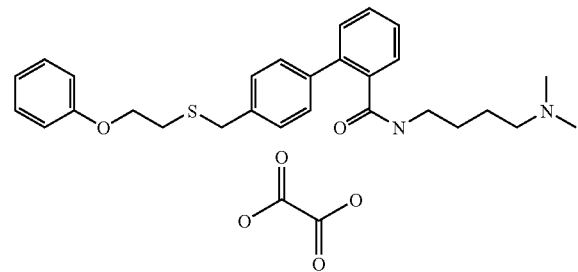

Prepared in the same manner as described for example 1. A solution of 4'-(2-phenoxy-ethylsulfanylmethyl)-biphenyl-2-carboxylic acid (0.85 g, 2.33 mmol, 1 eq.) in anhydrous THF was treated with 1,1'-carbonyldiimidazole (0.40 g, 2.45 mmol, 1.05 eq.) and warmed as described. The reaction was allowed to cool and then treated with 4-dimethylaminobutylamine (0.33 g, 2.80 mmol, 1.2 eq.). The reaction was treated as described in example 1 to give a yellow oil. The oil was purified by silica gel flash chromatography using 5% 2M NH$_3$ in methanol in chloroform as the mobile phase. Fractions containing the product were pooled and the solvent removed in vacuo leaving 4'-(2-phenoxy-ethylsulfanylmethyl)-biphenyl-2-carboxylic acid (4-dimethylamino-butyl)-amide (1.06 g, 98% yield) as a light yellow oil.

Converted the free base to the oxalate salt as described in example 4 to obtain 4'-(2-phenoxy-ethylsulfanylmethyl)-biphenyl-2-carboxylic acid (4-dimethylamino-butyl)-amide oxalate (0.8135 g) as a white solid.

$^1$H NMR (DMSO-d6) δ 8.15 (t, 1H, J=5 Hz), 7.35 (m, 10H), 6.94 (m, 3H), 4.13 (t, 2H, J=7 Hz), 3.89 (s, 2H), 3.06 (m, 2H), 2.93 (m, 2H), 2.82 (t, 2H, J=7 Hz), 2.69 (s, 6H), 1.47 (m, 2H), 1.31 (m, 2H). IR (KBr, cm$^{-1}$) 3263, 3167, 3141, 3053, 2922, 2854, 2751, 1730, 1635, 1601, 1585, 1496, 1230, 711. MS (ES$^+$) m/e 463. MS (ES$^-$) 521 [M+OAc]$^-$, 461. Analytical composition calculated for $C_{30}H_{36}N_2O_6S$ C, 65.20; H, 6.57; N, 5.07. Found C, 59.90; H, 6.00; N, 7.54. Analytical HPLC 100% purity. MP 72–76° C.

Preparation of 3'-2-phenoxy-ethylsulfanylmethyl)-biphenyl-2-carboxylic acid from ethyl 3-bromobenzoate and 3-methylbenzeneboronic acid

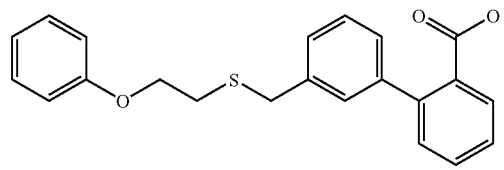

a) 3'-Methyl-biphenyl-2-carboxylic acid ethyl ester

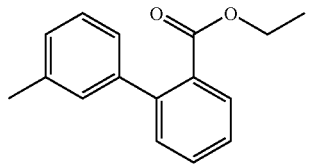

This compound was synthesized essentially as described for the synthesis of 4'-methyl-biphenyl-3-carboxylic acid ethyl ester. Ethyl 2-bromobenzoate (5.61 g, 24.51 mmol, 1 eq.) and 3-methylbenzeneboronic acid (3.5 g, 25.74 mmol, 1.05 eq.) in anhydrous THF were treated with palladium(II) acetate (0.55 g, 2.45 mmol, 10 mol %), triphenylphosphine (2.83 g, 10.78 mmol, 4.4×Pd), copper(I) iodide (0.17 g, 0.89 mmol, catalyst), and aqueous 2M sodium carbonate (26.96 mL, 53.92 mmol, 2.2 eq.). When complete, the reaction was worked up as described leaving a dark orange/brown oil.

The oil was purified by preparative HPLC (Waters LC-2000) using a gradient starting with 100% hexane and going to 8% EtOAc in hexane over 30 minutes. Fractions containing the product were pooled and the solvent removed in vacuo leaving 3'-methyl-biphenyl-2-carboxylic acid ethyl ester (4.36 g, 74% yield) as an orange oil.

$^1$H NMR (DMSO-d6) δ 7.73 (m, 2H), 7.60 (m, 1H), 7.47 (m, 2H), 7.30 (m, 1H), 7.18 (m, 1H), 7.07 (m, 1H), 4.32 and 4.03 (q, 2H total, J=7 Hz, atropisomerism of ester), 2.34 (s, 3H), 1.32 and 0.95 (t, 3H total, J=7 Hz, atropisomerism of ester). IR (CHCl$_3$, cm$^{-1}$) 1715, 1292, 1251, 1134. MS (ES$^+$) m/e 241, 195 [M–OEt]$^+$. Analytical composition calculated for C$_{16}$H$_{16}$O$_2$ C, 79.97; H, 6.71; N, 0. Found C, 69.74; H, 5.74; N, 0.32.

b) 3'-Bromomethyl-biphenyl-2-carboxylic acid ethyl ester

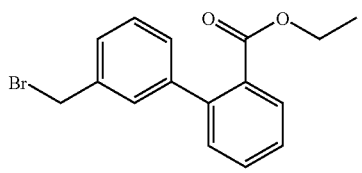

3'-Bromomethyl-biphenyl-2-carboxylic acid ethyl ester was synthesized as described for 4'-bromomethyl-biphenyl-3-carboxylic acid ethyl ester. 3'-Methyl-biphenyl-2-carboxylic acid ethyl ester (4.3 g, 17.89 mmol, 1 eq.) in carbon tetrachloride was treated with N-bromosuccinimide (3.82 g, 21.47 mmol, 1.2 eq.) and 2,2'-azobisisobutyronitrile (0.15 g, 0.89 mmol, 5 mol %). When complete, the reaction was worked up as described leaving a tan oil.

The oil was purified by silica gel flash column chromatography using a step gradient starting with 100% hexane (2 L) and going to 2.5% EtOAc in hexane (2 L) and then 5% EtOAc in hexane (2 L). Fractions containing the product were pooled and the solvent removed in vacuo leaving 3'-bromomethyl-biphenyl-2-carboxylic acid ethyl ester (5.49 g, 96% yield) as a light yellow oil.

$^1$H NMR (DMSO-d6) δ 7.76 (m, 1H), 7.64 (m, 1H), 7.46 (m, 4H), 7.33 (m, 1H), 7.24 (m, 1H), 4.75 (s, 2H), 4.32 and 4.03 (q, 2H, J=7 Hz, atropisomerism of ester), 1.32 and 0.91 (t, 3H, J=7 Hz, atropisomerism of ester). IR (CHCl$_3$, cm$^{-1}$) 1714, 1600, 1293, 1251, 1135. MS (ES$^+$) m/e 319, 321; 239 [M–Br]$^+$. Analytical composition calculated for C$_{16}$H$_{15}$BrO$_2$ C, 60.21; H, 4.74. Found C, 51.93; H, 3.92.

c) 3'-(2-Hydroxy-ethylsulfanylmethyl)-biphenyl-2-carboxylic acid ethyl ester

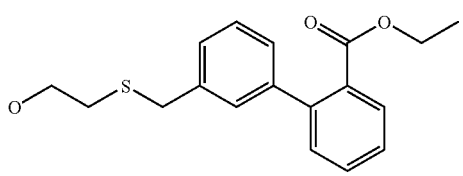

3'-(2-Hydroxy-ethylsulfanylmethyl)-biphenyl-2-carboxylic acid ethyl ester was prepared as described for 4'-(2-hydroxy-ethylsulfanylmethyl)-biphenyl-3-carboxylic acid ethyl ester. 3'-Bromomethyl-biphenyl-2-carboxylic acid ethyl ester (5.4 g, 16.92 mmol, 1 eq.). in anhydrous DMF was treated with 2-mercaptoethanol (1.59 g, 20.30 mmol, 1.2 eq.) and potassium carbonate (7.02 g, 50.76 mmol, 3 eq.). When complete, the reaction was worked up as described leaving a light yellow oil.

The oil was purified via silica gel flash chromatography using a step gradient of EtOAc in hexane as the mobile phase. Fractions containing the product were pooled and the solvent removed in vacuo leaving 3'-(2-hydroxy-ethylsulfanylmethyl)-biphenyl-2-carboxylic acid ethyl ester (2.15 g, 40% yield) as a light yellow oil.

$^1$H NMR (DMSO-d6) δ 7.72 (m, 1H), 7.61 (m, 1H), 7.49 (m, 1H), 7.37 (m, 3H), 7.24 (s, 1H), 7.16 (m, 1H), 4.77 (t, 1H, J=5 Hz), 4.03 (q, 2H, J=7 Hz), 3.79 (s, 2H), 3.53 (m, 2H), 2.50 (m, 2H), 0.94 (t, 3H, J=7 Hz). IR (CHCl$_3$, cm$^{-1}$) 3506, 1712, 1600, 1473, 1288, 1250, 1134, 1094, 1052. MS (ES$^+$) m/e 299 [M–OH]$^+$; 271 [M–OEt]$^+$; 239 [M–SCH$_2$CH$_2$OH]$^+$. Analytical composition calculated for C$_{18}$H$_2$O$_3$S C, 68.33; H, 6.37. Found C, 68.13; H, 6.29.

d) 3'-(12-Phenoxy-ethylsulfanylmethyl)-biphenyl-2-carboxylic acid ethyl ester

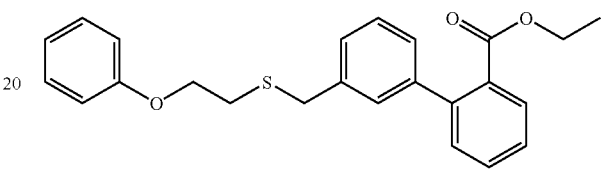

3'-(2-Phenoxy-ethylsulfanylmethyl)-biphenyl-2-carboxylic acid ethyl ester was prepared as described for 4'-(2-phenoxy-ethylsulfanylmethyl)-biphenyl-3-carboxylic acid ethyl ester. 3'-(2-Hydroxy-ethylsulfanylmethyl)-biphenyl-2-carboxylic acid ethyl ester (2.1 g, 6.64 mmol, 1 eq.) in anhydrous THF was treated with phenol (0.88 g, 9.30 mmol, 1.4 eq.), triphenylphosphine (2.44 g, 9.30 mmol, 1.4 eq.), and diisopropyl azidocarboxylate (1.88 g, 1.83 mL, 9.30 mmol, 1.4 eq.). When complete, the reaction was worked up as described leaving a yellow oil The oil was purified by silica gel flash chromatography using 5% EtOAc in hexane as the mobile phase. Fractions containing the product were pooled and the solvent removed in vacuo leaving 3'-(2-phenoxy-ethylsulfanylmethyl)-biphenyl-2-carboxylic acid ethyl ester (2.15 g, 82% yield) as a yellow oil.

$^1$H NMR (DMSO-d6) δ57.72 (m, 1H), 7.60 (m, 1H), 7.48 (m, 1H), 7.38 (m, 2H), 7.26 (m, 3H), 7.17 (m, 2H), 6.92 (m, 2H), 6.76 (m, 1H), 4.11 (t, 2H, J=7 Hz), 4.02 (q, 2H, J=7 Hz), 3.89 (s, 2H), 2.79 (t, 2H, J=7 Hz), 0.93 (t, 3H, J=7 Hz). IR (CHCl$_3$, cm$^{-1}$) 1714, 1599, 1498, 1291, 1245. MS (FD$^+$) m/e 392. Analytical composition calculated for C$_{24}$H$_{24}$O$_3$S C, 73.44; H, 6.16. Found C, 66.49; H, 5.55.

e) 3'-(2-Phenoxy-ethylsulfanylmethyl)-biphenyl-2-carboxylic acid

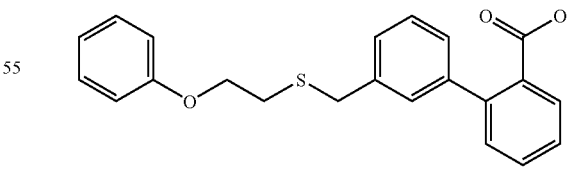

3'-(2-Phenoxy-ethylsulfanylmethyl)-biphenyl-2-carboxylic acid was synthesized as described for 4'-(2-phenoxy-ethylsulfanylmethyl)-biphenyl-3-carboxylic acid. 3'-(2-Phenoxy-ethylsulfanylmethyl)-biphenyl-2-carboxylic acid ethyl ester (2.1 g, 5.35 mmol, 1 eq.) in 30% aqueous THF was treated with lithium hydroxide (0.38 g, 16.05 mmol, 3 eq.). When complete, the reaction was worked up as described leaving 3'-(2-phenoxy-ethylsulfanylmethyl)-biphenyl-2-carboxylic acid (1.94, 99% yield) as a yellow oil.

$^1$H NMR (DMSO-d6) δ 12.7 (s, 1H), 7.73 (m, 1H), 7.55 (m, 1H), 7.45 (m, 1H), 7.26 (m, 7H), 6.92 (m, 2H), 6.76 (m, 1H), 4.10 (t, 2H, J=7 Hz), 3.88 (s, 2H), 2.79 (t, 2H, J=7Hz). IR (CHCl$_3$, cm$^{-1}$) 3030, 1702, 1599, 1587, 1498, 1470, 1294, 1244, 1173. MS (ES$^+$) m/e 271 [M−OPh]$^+$. MS (ES$^-$) m/e 363. Analytical composition calculated for C$_{22}$H$_{20}$O$_3$S C, 72.50; H, 5.53. Found C, 61.78; H, 4.59.

Example 10

Preparation of 3'-(2-phenoxy-ethylsulfanylmethyl)-biphenyl-2-carboxylic acid (2-dimethylamino-ethyl)-amide hydrochloride

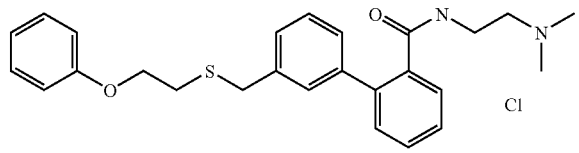

3'-(2-Phenoxy-ethylsulfanylmethyl)-biphenyl-2-carboxylic acid (2-dimethylamino-ethyl)-amide was synthesized as described for 4'-(2-phenoxy-ethylsulfanylmethyl)-biphenyl-3-carboxylic acid (3-dimethylamino-propyl)-amide. 3'-(2-phenoxy-ethylsulfanylmethyl)-biphenyl-2-carboxylic acid (1.02 g, 2.8 mmol, 1 eq.) in anhydrous THF was treated with 1,1-carbonyldiimidazole (0.46 g, 2.86 mmol, 1.02 eq.) and N,N-dimethylethylenediamine (0.30 g, 3.36 mmol, 1.2 eq.) as described. When complete, the reaction was worked up as described leaving a yellow oil.

The oil was purified via silica gel flash chromatography using 5% 2M NH$_3$ in methanol in chloroform as the mobile phase. Fractions containing the product were pooled and the solvent removed in vacuo leaving 3'-(2-phenoxy-ethylsulfanylmethyl)-biphenyl-2-carboxylic acid (2-dimethylamino-ethyl)-amide (0.92 g, 75% yield) as a light yellow oil.

The free base was converted to the hydrochloride salt by adding a solution of acetyl chloride (0.18 mL, 1.2 eq.) in EtOH (1 mL) dropwise to an ether solution of the free base. The resulting white solid (0.69 g) was collected by filtration and dried in a vacuum oven.

$^1$H NMR (DMSO-d6) δ 10.48 (s, 1H), 8.49 (t, 1H, J=5 Hz), 7.55–7.24 (m, 10H), 6.93 (m, 3H), 4.11 (t, 2H, J=7 Hz), 3.89 (s, 2H), 3.44 (m, 2H), 3.03 (t, 2H, J=7 Hz), 2.82 (t, 2H, J=7 Hz), 2.69 (s, 6H). IR (CHCl$_3$, cm$^{-1}$) 3424, 3247, 2975, 1658, 1600, 1521, 1498, 1471, 1243. MS (ES$^+$) m/e 435. MS (ES$^-$) m/e 433. Analytical composition calculated for C$_{26}$H$_{31}$ClN$_2$O$_2$S C, 66.29; H, 6.63; N, 5.95. Found C, 65.94; H, 6.90; N, 5.79. MP 150–153° C.

Example 11

Preparation of 3'-(2-phenoxy-ethylsulfanylmethyl)-biphenyl-2-carboxylic acid (3-dimethylamino-propyl)-amide

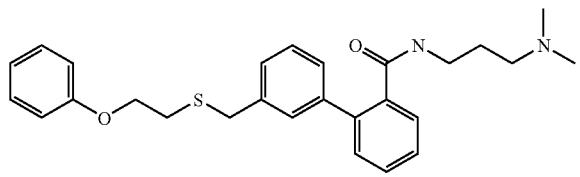

3'-(2-Phenoxy-ethylsulfanylmethyl)-biphenyl-2-carboxylic acid (3-dimethylamino-propyl)-amide was synthesized as described for 4'-(2-phenoxy-ethylsulfanylmethyl)-biphenyl-3-carboxylic acid (3-dimethylamino-propyl)-amide. 3'-(2-Phenoxy-ethylsulfanylmethyl)-biphenyl-2-carboxylic acid (0.95 g, 2.61 mmol, 1 eq.) in anhydrous THF was treated with 1,1-carbonyldiimidazole (0.43 g, 2.66 mmol, 1.02 eq.) and 3-(dimethylamino)propylamine (0.32 g, 3.13 mmol, 1.2 eq.) as described. When complete, the reaction was worked up as described leaving a yellow oil.

The oil was purified via silica gel flash chromatography using 10% 2M NH$_3$ in methanol in diethyl ether as the mobile phase. Fractions containing the product were pooled and the solvent removed in vacuo leaving 3'-(2-phenoxy-ethylsulfanylmethyl)-biphenyl-2-carboxylic acid (3-dimethylamino-propyl)-amide (0.42 g, 36% yield) as a light yellow oil.

$^1$H NMR (DMSO-d6) δ 8.09 (t, 1H, J=5 Hz), 7.46 (m, 1H), 7.41–7.23 (m, 9H), 6.92 (m, 3H), 4.10 (t, 2H, J=7 Hz), 3.87 (s, 2H), 3.06 (t, 2H, J=7 Hz), 2.80 (t, 2H, J=7 Hz), 2.04 (m, 8H), 1.41 (m, 2H). IR (CHCl$_3$, cm$^{-1}$) 3439, 3004, 2949, 2865, 2824, 2780, 1649, 1600, 1520, 1497, 1470, 1244, 1033. MS (ES$^+$) m/e 449. MS (ES$^-$) m/e 447. Analytical composition calculated for C$_{27}$H$_{32}$N$_2$O$_2$S C, 72.29; H, 7.19; N, 6.24. Found C, 72.13; H, 7.25; N, 6.25.

Example 12

Preparation of 3'-(2-phenoxy-ethylsulfanylmethyl)-biphenyl-2-carboxylic acid (4-dimethylamino-butyl)-amide

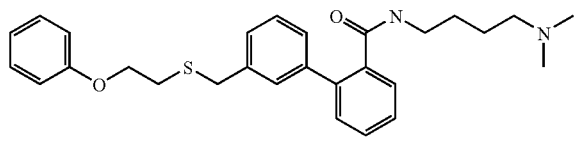

3'-(2-Phenoxy-ethylsulfanylmethyl)-biphenyl-2-carboxylic acid (4-dimethylamino-butyl)-amide was synthesized as described for 4'-(2-phenoxy-ethylsulfanylmethyl)-biphenyl-3-carboxylic acid (3-dimethylamino-propyl)-amide. 3'-(2-Phenoxy-ethylsulfanylmethyl)-biphenyl-2-carboxylic acid (0.95 g, 2.61 mmol, 1 eq.) in anhydrous THF was treated with 1,1-carbonyldiimidazole (0.43 g, 2.66 mmol, 1.02 eq.) and 4-dimethylaminobutylamine (0.36 g, 3.13 mmol, 1.2 eq.) as described. When complete, the reaction was worked up as described leaving a yellow oil.

Purified the oil via silica gel flash chromatography using 10% 2M NH$_3$ in methanol in diethyl ether as the mobile phase. Fractions containing the product were pooled and the solvent removed in vacuo leaving 3'-(2-phenoxy-ethylsulfanylmethyl)-biphenyl-2-carboxylic acid (4-dimethylamino-butyl)-amide (0.40 g, 33% yield) as a light yellow oil.

$^1$H NMR (DMSO-d6) δ 8.15 (t, 1H, J=5 Hz), 7.46 (m, 1H), 7.41–7.23 (m, 9H), 6.92 (m, 3H), 4.09 (t, 2H, J=7 Hz), 3.87 (s, 2H), 3.05 (m, 2H), 2.80 (t, 2H, J=7 Hz), 2.09 (m, 2H), 2.05 (s, 6H), 1.28 (m, 4H). IR (CHCl$_3$, cm$^{-1}$) 2944, 2864, 2824, 1650, 1601, 1497, 1221, 1219, 1211. MS (ES$^+$) m/e 463. MS (ES$^-$) m/e 461. Analytical composition calculated for C$_{28}$H$_{34}$N$_2$O$_2$S C, 72.69; H, 7.41; N, 6.05. Found C, 68.07; N, 6.91; N, 5.74. Analytical HPLC 95% pure.

Preparation of 3'-(2-phenoxy-ethylsulfanylmethyl)-biphenyl-3-carboxylic acid from 3-methylbenzeneboronic acid and ethyl 3-bromobenzoate

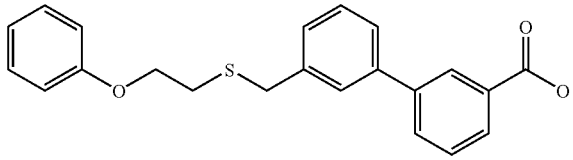

a) 3'-Methyl-biphenyl-3-carboxylic acid ethyl ester

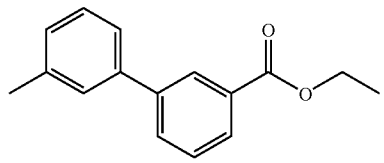

3'-Methyl-biphenyl-3-carboxylic acid ethyl ester was synthesized as described for 4'-methyl-biphenyl-3-carboxylic acid ethyl ester. Ethyl 3-bromobenzoate (3.83 g, 16.72 mmol, 1 eq.) and 3-methylbenzeneboronic acid (2.5 g, 18.39 mmol, 1.1 eq.) in THF were treated with aqueous sodium carbonate (2M solution, 18.4 mL, 36.78 mmol, 2.2 eq.), palladium(II) acetate (0.37 g, 1.67 mmol, 10 mol %), triphenylphosphine (1.93 g, 7.35 mmol, 4.4×Pd), and copper (I) iodide (0.1 g, catalyst). When complete, the reaction was worked up as described leaving a brown oil.

The oil was purified by preparative HPLC (Waters LC-2000) using a gradient of EtOAc in hexane as the mobile phase. Fractions containing the product were pooled and the solvent removed in vacuo leaving 3'-methyl-biphenyl-3-carboxylic acid ethyl ester (3.04 g, 76% yield) as a faint yellow oil.

$^1$H NMR (DMSO-d6) δ 8.17 (m, 1H), 7.94 (m, 2H), 7.62 (t, 1H, J=8 Hz), 7.48 (m, 2H), 7.39 (t, 1H, J=8 Hz), 7.23 (d, 1H, J=7 Hz), 4.36 (q, 2H, J=7 Hz), 2.40 (s, 2H), 1.35 (t, 3H, J=7 Hz). IR (CHCl$_3$, cm$^{-1}$) 1715, 1369, 1312, 1270, 1254, 1111. MS (ES$^+$) m/e 241. Analytical composition calculated for C$_{16}$H$_{16}$O$_2$ C, 79.97; H, 6.71; N, 0. Found C, 79.65; H, 6.75; N, 0.16.

d) 3'-Bromomethyl-biphenyl-3-carboxylic acid ethyl ester

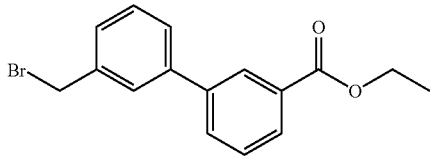

3'-Bromomethyl-biphenyl-3-carboxylic acid ethyl ester was synthesized as described for 4'-bromomethyl-biphenyl-3-carboxylic acid ethyl ester. 3'-Methyl-biphenyl-3-carboxylic acid ethyl ester (4.2 g, 17.48 mmol, 1 eq.) in carbon tetrachloride was treated with N-bromosuccinimide (3.73 g, 20.98 mmol, 1.2 eq.) and 2,2'-azobisisobutyronitrile (0.14 g, 0.87 mmol, 5 mol %). When complete, the reaction was worked up as described leaving an orange oil.

The oil was purified via silica gel flash chromatography using 5% EtOAc in hexane as the mobile phase. Fractions containing the product were pooled and the solvent removed in vacuo leaving 3'-bromomethyl-biphenyl-3-carboxylic acid ethyl ester (4.5 g, 81% yield) as a light yellow oil.

$^1$H NMR (DMSO-d6) δ 8.06 (m, 1H), 7.95 (m, 1H), 7.86 (m, 1H), 7.64 (m, 1H), 7.50 (m, 3H), 4.82 (s, 2H), 4.33 (q, 2H, J=7 Hz), 1.33 (t, 3H, J=7 Hz). IR (CHCl$_3$, cm$^{-1}$) 1716, 1369, 1296, 1297, 1256, 1111. MS (ES$^+$) m/e 319, 321.

Analytical composition calculated for C$_{16}$H$_{15}$BrO$_2$ C, 60.21; H, 4.74. Found C, 53.31; H, 3.29.

c) 3'-(2-Hydroxy-ethylsulfanylmethyl)-biphenyl-3-carboxylic acid ethyl ester

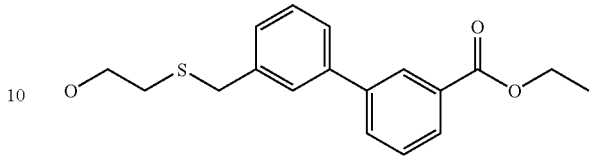

3'-(2-Hydroxy-ethylsulfanylmethyl)-biphenyl-3-carboxylic acid ethyl ester was synthesized as described for 4'-(2-hydroxy-ethylsulfanylmethyl)-biphenyl-3-carboxylic acid ethyl ester. 3'-Bromomethyl-biphenyl-3-carboxylic acid ethyl ester (3.4 g, 10.65 mmol, 1 eq.) in anhydrous DMF was treated with 2-mercaptoethanol (1.0g, 12.78 mmol, 1.2 eq.) and potassium carbonate (4.42 g, 31.95 mmol, 3 eq.). When complete, the reaction was worked up as described leaving a yellow oil.

The oil was purified by silica gel flash chromatography using a step gradient of EtOAc in hexane as the mobile phase. Fractions containing the product were pooled and the solvent removed in vacuo leaving 3'-(2-hydroxy-ethylsulfanylmethyl)-biphenyl-3-carboxylic acid ethyl ester (1.1 g, 33% yield) as a light yellow oil.

$^1$H NMR (DMSO-d6) δ 8.19 (m, 1H), 7.96 (m, 2H), 7.61 (m, 3H), 7.46 (m, 1H), 7.37 (m, 1H), 4.79 (t, 1H, J=5 Hz), 4.36 (q, 2H, J=7 Hz), 3.86 (s, 2H), 3.54 (m, 2H), 2.53 (m, 2H1), 1.35 (t, 3H, J=7 Hz). IR (CHCl$_3$, cm$^{-1}$) 3599, 3507, 3007, 1712, 1254. MS (ES$^+$) m/e 299 [M−OH]$^+$.

d) 3'-(2-Phenoxy-ethylsulfanylmethyl)-biphenyl-3-carboxylic acid ethyl ester

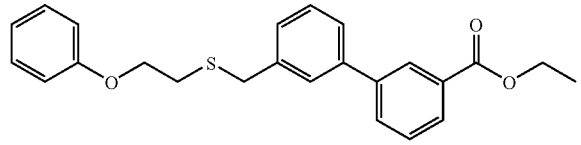

3'-(2-Phenoxy-ethylsulfanylmethyl)-biphenyl-3-carboxylic acid ethyl ester was synthesized as described for 4'-(2-phenoxy-ethylsulfanylmethyl)-biphenyl-3-carboxylic acid ethyl ester. 3'-(2-Hydroxy-ethylsulfanylmethyl)-biphenyl-3-carboxylic acid ethyl ester (1.0 g, 3.16 mmol, 1 eq.) in anhydrous THF was treated with phenol (0.42 g, 4.42 mmol, 1.4 eq.), triphenylphosphine (1.16 g, 4.42 mmol, 1.4 eq.), and diisopropyl azidocarboxylate (0.89 g, 4.42 mmol, 1.4 eq.). When complete, the reaction was worked up as described leaving a yellow oil.

The oil was purified via silica gel flash chromatography using 5% EtOAc in hexane as the mobile phase. Fractions containing the product were pooled and the solvent removed in vacuo leaving 3'-(2-phenoxy-ethylsulfanylmethyl)-biphenyl-3-carboxylic acid ethyl ester (0.75 g, 60% yield) as a light yellow oil.

$^1$H NMR (DMSO-d6) δ 8.18 (m, 1H), 7.94 (m, 2H), 7.62 (m, 3H), 7.44 (m, 2H), 7.25 (m, 2H), 6.91 (m, 3H), 4.35 (q, 2H, J=7 Hz), 4.11 (t, 2H, J=7 Hz), 3.95 (s, 2H), 2.80 (t, 2H, J=7 Hz), 1.34 (t, 3H, J=7 Hz). MS (FD$^+$) m/e 392.

e) 3'-(2-Phenoxy-ethylsulfanylmethyl)-biphenyl-3-carboxylic acid

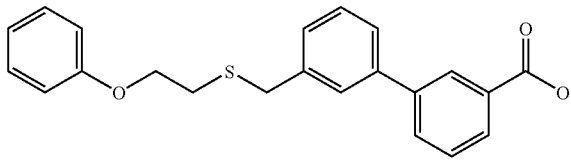

3'-(2-Phenoxy-ethylsulfanylmethyl)-biphenyl-3-carboxylic acid was synthesized as described for 4'-(2-phenoxy-ethylsulfanylmethyl)-biphenyl-3-carboxylic acid. 3'-(2-Phenoxy-ethylsulfanylmethyl)-biphenyl-3-carboxylic acid ethyl ester (0.80 g, 2.04 mmol, 1 eq.) in 30% aqueous THF was treated with lithium hydroxide (0.15 g, 6.12 mmol, 3 eq.). When complete, the reaction was worked up as described leaving 3'-(2-phenoxy-ethylsulfanylmethyl)-biphenyl-3-carboxylic acid (0.73 g, 98% yield) as an orange oil that solidified on standing.

$^1$H NMR (DMSO-d6) δ 13.1 (s, 1H), 8.19 (m, 1H), 7.92 (m, 2H), 7.69 (s, 1H), 7.60 (m, 2H), 7.43 (m, 2H), 7.25 (m, 2H), 6.91 (m, 3H), 4.11 (t, 2H, J=7 Hz), 3.95 (s, 2H), 2.80 (t, 2H, J=7 Hz). IR (KBr, cm$^{-1}$) 1695, 1601, 1498, 1314, 1241, 757, 748, 691. MS (ES$^+$) m/e 382 [M+NH$_4$]$^+$. MS (ES$^-$) m/e 363.

Example 13

Preparation of 3'-(2-phenoxy-ethylsulfanylmethyl)-biphenyl-3-carboxylic acid (3-dimethylamino-propyl)-amide oxalate

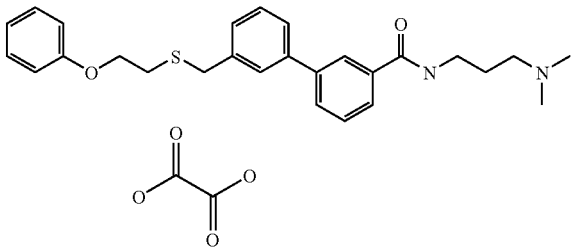

3'-(2-Phenoxy-ethylsulfanylmethyl)-biphenyl-3-carboxylic acid (3-dimethylamino-propyl)-amide was synthesized as described for 4'-(2-phenoxy-ethylsulfanylmethyl)-biphenyl-3-carboxylic acid (3-dimethylamino-propyl)-amide. 3'-(2-Phenoxy-ethylsulfanylmethyl)-biphenyl-3-carboxylic acid (0.7 g, 1.92 mmol, 1 eq.) in anhydrous THF was treated with 1,1-carbonyldiimidazole (0.32 g, 1.96 mmol, 1.02 eq.), and 3-(dimethylamino)propylamine (0.30 g, 2.30 mmol, 1.2 eq.) as described. When complete, the reaction was worked up as described leaving a yellow oil.

Purified the oil via silica gel flash chromatography using 10% 2M NH$_3$ in methanol in chloroform as the mobile phase. Fractions containing the product were pooled and the solvent removed in vacuo leaving 3'-(2-phenoxy-ethylsulfanylmethyl)-biphenyl-3-carboxylic acid (3-dimethylamino-propyl)-amide (0.65 g, 76% yield) as a faint yellow oil. The free base was converted to the oxalate salt by adding oxalic acid (0.14 g, 1.1 eq) in EtOAc dropwise to a solution of the free base in EtOAc. The resulting gum was dissolved in a little methanol and the solution added dropwise to vigorously stirred diethyl ether. The resulting off-white solid was collected by filtration and dried to give 3'-(2-phenoxy-ethylsulfanylmethyl)-biphenyl-3-carboxylic acid (3-dimethylamino-propyl)-amide oxalate (0.5232 g).

$^1$H NMR (DMSO-d6) δ 8.77 (t, 1H, J=5 Hz), 8.13 (s, 1H1), 7.82 (m, 2H), 7.70 (s, 1H), 7.58 (m, 2H), 7.43 (m, 2H), 7.26 (m, 2H), 6.92 (m, 3H), 4.12 (t, 2H, J=7 Hz), 3.95 (s, 2H), 3.35 (m, 2H), 3.04 (m, 2H), 2.81 (t, 2H, J=7 Hz), 2.72 (s, 6H), 1.90 (m, 2H). IR (KBr, cm$^{-1}$) 3413, 3260, 3027, 1717, 1636, 1600, 1241, 691, 434. MS (ES$^+$) m/e 449. MS (ES$^-$) m/e 507 [M+OAc]$^-$. Analytical composition calculated for C$_{29}$H$_{34}$N$_2$O$_6$S C, 64.66; H, 6.36; N, 5.20. Found C, 63.49; H, 6.50; N, 5.50. Analytical HPLC 91.5% purity. MP51–53° C.

Preparation of 3'-(2-phenoxy-ethylsulfanylmethyl)-biphenyl4-carboxylic acid from ethyl 4-iodobenzoate and 3-methylbenzeneboronic acid

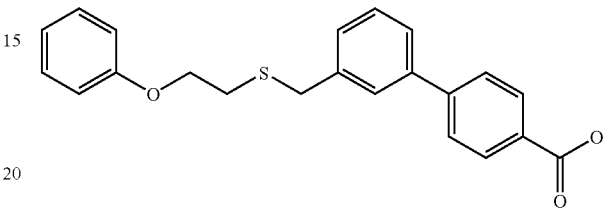

a) 3'-Methyl-biphenyl4-carboxylic acid ethyl ester

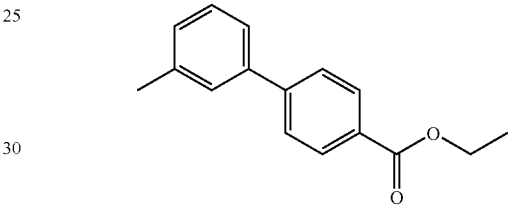

3'-Methyl-biphenyl-4-carboxylic acid ethyl ester was synthesized as described for 4'-methyl-biphenyl-3-carboxylic acid ethyl ester. Ethyl 4-iodobenzoate (4.62 g, 16.72 mmol, 1 eq.) and 3-methylbenzeneboronic acid (2.50 g, 18.39 mmol, 1.1 eq.) in THF and aqueous 2M sodium carbonate (18.4 mL, 2.2 eq.) were treated with palladium(II) acetate (0.37 g, 1.67 mmol, 10 mol %), triphenylphosphine (1.93 g, 7.35 mmol, 4.4×Pd), and copper(I) iodide (0.10 g). When complete, the reaction was worked up as described leaving a brown oil.

The oil was purified by preparative HPLC (Waters LC2000) using a gradient of EtOAc in hexane as the mobile phase. Fractions containing the product were pooled and the solvent removed in vacuo leaving 3'-methyl-biphenyl-4-carboxylic acid ethyl ester (3.91 g, 97% yield) as a yellow oil.

$^1$H NMR (DMSO-d6) δ 8.03 (d, 2H, J=8 Hz), 7.80 (d, 2H, J=8 Hz), 7.53 (m, 2H), 7.39 (t, 1H, J=8 Hz), 7.24 (m, 1H), 4.34 (q, 2H, J=7 Hz), 2.39 (s, 3H), 1.34 (t, 3H, J=7 Hz). IR (CHCl$_3$, cm$^{-1}$) 1709, 1609, 1297, 1110. MS (ES$^+$) m/e 241. Analytical composition calculated for C$_{16}$H$_{16}$O$_2$ C, 79.97; H, 6.71; N, 0. Found C, 78.84; H, 6.29; N, 0.09.

b) 3'-Bromomethyl-biphenyl4-carboxylic acid ethyl ester

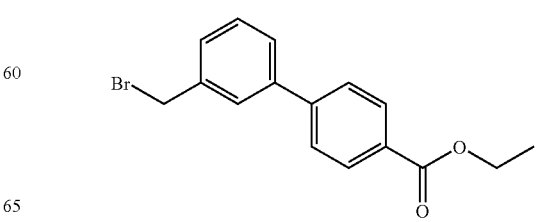

3'-Bromomethyl-biphenyl-4-carboxylic acid ethyl ester was synthesized as described for 4'-bromomethyl-biphenyl-3-carboxylic acid ethyl ester. 3'-Methyl-biphenyl-4-carboxylic acid ethyl ester (3.80 g, 15.81 mmol, 1 eq.) in carbon tetrachloride was treated with N-bromosuccinimide (3.1 g, 17.39 mmol, 1.1 eq.) and 2,2'-azobisisobutyronitrile (0.13 g, 0.79 mmol, 5 mol %). When complete, the reaction was worked up as described leaving 3'-bromomethyl-biphenyl-4-carboxylic acid ethyl ester (4.83 g, 96%) as a yellow oil that crystallized on standing.

$^1$H NMR (DMSO-d6) δ 8.06 (m, 2H), 7.83 (m, 3H), 7.70 (m, 1H), 7.51 (m, 2H), 4.79 (s, 2H), 4.34 (q, 2H, J=7 Hz), 1.35 (t, 3H, J=7 Hz). IR (CHCl$_3$, cm$^{-1}$) 1710, 1610, 1589, 1478, 1369, 1309, 1281, 1184, 1106, 1018. MS (FD$^+$)m/e 320, 318.. Analytical composition calculated for C$_{16}$H$_{15}$BrO$_2$ C, 60.21; H, 4.74; N, 0. Found C, 56.33; H, 4.41; N, 0.16.

c) 3'-(2-Hydroxy-ethylsulfanylmethyl)-biphenyl-4-carboxylic acid ethyl ester

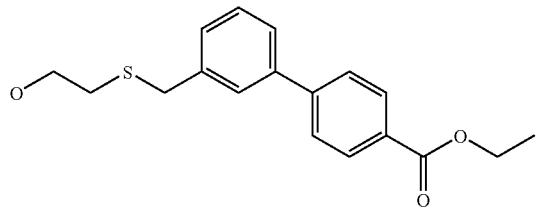

3'-(2-Hydroxy-ethylsulfanylmethyl)-biphenyl-4-carboxylic acid ethyl ester was synthesized as described for 4'-(2-hydroxy-ethylsulfanylmethyl)-biphenyl-3-carboxylic acid ethyl ester. 3'-Bromomethyl-biphenyl-4-carboxylic acid ethyl ester (4.98 g, 15.6 mmol, 1 eq) in anhydrous DMF was treated with 2-mercaptoethanol (2.44 g, 31.20 mmol, 2 eq.) and potassium carbonate (6.47 g, 46.80 mmol, 3 eq.). When complete, the reaction was worked up as described leaving a yellow oil.

The oil was purified by silica gel flash chromatography using a step gradient of EtOAc in hexane as the mobile phase. Fractions containing the product were pooled and the solvent removed in vacuo leaving 3'-(2-hydroxy-ethylsulfanylmethyl)-biphenyl-4-carboxylic acid ethyl ester (2.11 g, 43% yield) as a yellow oil.

$^1$H NMR (DMSO-d6) δ 8.04 (d, 2H, J=8 Hz), 7.82 (d, 2H, J=8 Hz), 7.69 (m, 1H) 7.61 (m, 1H), 7.43 (m, 2H), 4.77 (t, 1H, J=5 Hz), 4.34 (q, 2H, J=7 Hz), 3.84 (s, 2H), 3.52 (m, 2H), 2.50 (m, 2H), 1.34 (t, 3H, J=7 Hz). IR (CHCl$_3$, cm$^{-1}$) 3599, 3497, 1709, 1609, 1281, 1109, 1018. MS (FD$^+$) m/e 316. Analytical composition calculated for C$_{18}$H$_{20}$O$_3$S C, 68.33; H, 6.37; N, 0. Found C, 67.90; H, 6.30; N, 0.27.

d) 3'-(2-Phenoxy-ethylsulfanylmethyl)-biphenyl-4-carboxylic acid ethyl ester

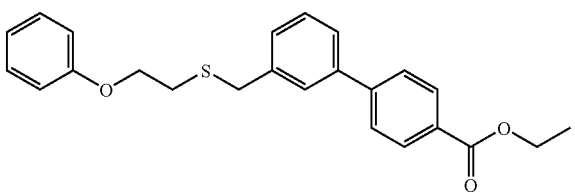

3'-(2-Phenoxy-ethylsulfanylmethyl)-biphenyl-4-carboxylic acid ethyl ester was synthesized as described for 4'-(2-phenoxy-ethylsulfanylmethyl)-biphenyl-3-carboxylic acid ethyl ester. 3'-(2-Hydroxy-ethylsulfanylmethyl)-biphenyl-4-carboxylic acid ethyl ester (1.95 g, 6.16 mmol, 1 eq.) in anhydrous THF was treated with phenol (0.75 g, 8.01 mmol, 1.3 eq.), triphenylphosphine (2.10 g, 8.01 mmol, 1.3 eq.), and diisopropyl azidocarboxylate (1.62 g, 8.01 mmol, 1.3 eq.). When complete, the reaction was worked up as described leaving an orange oil.

The oil was purified by silica gel flash chromatography using EtOAc in hexane as the mobile phase. Fractions containing the product were pooled and the solvent removed in vacuo leaving 3'-(2-phenoxy-ethylsulfanylmethyl)-biphenyl-4carboxylic acid ethyl ester (2.05 g, 85% yield) as a yellow oil.

$^1$H NMR (DMSO-d6) δ 8.03 (d, 2H, J=8 Hz), 7.79 (d, 2H, J=8 Hz), 7.71 (s, 1H), 7.62 (m, 1H), 7.44 (m, 2H), 7.26 (m, 2H), 6.92 (m, 3H), 4.34 (q, 2H, J=7 Hz), 4.12 (t, 2H, J=7 Hz), 3.94 (s, 2H), 2.81 (t, 2H, J=7 Hz), 1.34 (t, 3H, J=7 Hz). IR (CHCl$_3$, cm$^{-1}$) 1933, 1710, 1601, 1498, 1281, 1244, 1108, 1018. MS (FD$^+$)m/e 392. Analytical composition calculated for C$_{24}$H$_{24}$O$_3$S C, 73.44; H, 6.16; N, 0. Found C, 67.16; H, 5.72; N, 0.10.

e) 3'-(2-Phenoxy-ethylsulfanylmethyl)-biphenyl-4-carboxylic acid

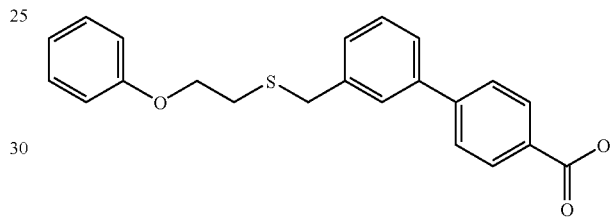

3'-(2-Phenoxy-ethylsulfanylmethyl)-biphenyl-4-carboxylic acid was synthesized as described for 4'-(2-phenoxyethylsulfanylmethyl)-biphenyl-3-carboxylic acid. 3'-(2-Phenoxy-ethylsulfanylmethyl)-biphenyl-4-carboxylic acid ethyl ester (2.0 g, 5.1 mmol, 1 eq.) in 30% aqueous THF was treated with lithium hydroxide (0.37 g, 15.3 mmol, 3 eq.). When complete, the reaction was worked up as described leaving 3'-(2-phenoxy-ethylsulfanylmethyl)-biphenyl-4-carboxylic acid (1.68 g, 90% yield) as a white solid.

$^1$H NMR (DMSO-d6) δ 12.96 (s, 1H), 8.01 (d, 2H, J-8 Hz), 7.77 (d, 2H, J=8 Hz), 7.71 (s, 1H), 7.62 (m, 1H), 7.44 (m, 2H), 7.26 (m, 2H), 6.92 (m, 3H), 4.12 (t, 2H, J=7 Hz), 3.94 (s, 2H), 2.80 (t, 2H, J=7 Hz). IR (KBr, cm$^{-1}$) 1689, 1607, 1422, 1286, 1243, 1170, 759. MS (ES$^-$) m/e 363. Analytical composition calculated for C$_{22}$H$_{20}$O$_3$S C, 72.50; H, 5.53; N, 0. Found C, 72.04; H, 5.55; N, 0.15.

Example 14

Preparation of 3'-(2-phenoxy-ethylsulfanylmethyl)-biphenyl-4-carboxylic acid (2-dimethylamino-ethyl)-amide

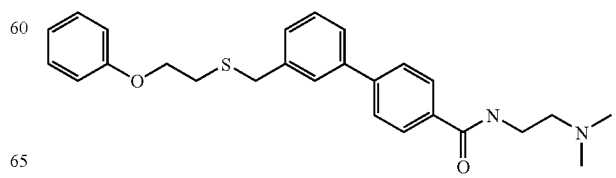

3'-(2-Phenoxy-ethylsulfanylmethyl)-biphenyl-4-carboxylic acid (2-dimethylamino-ethyl)-amide was synthesized as described for 4'-(2-phenoxy-ethylsulfanylmethyl)-biphenyl-3-carboxylic acid (3-dimethylamino-propyl)-amide. 3'-(2-Phenoxy-ethylsulfanylmethyl)-biphenyl-4-carboxylic acid (0.80 g, 2.19 mmol, 1 eq.) in anhydrous THF was treated with 1,1-carbonyldiimidazole (0.36 g, 2.23 mmol, 1.02 eq.) and N,N-dimethylethylenediamine (0.23 g, 2.63 mmol, 1.2 eq.). When complete, the reaction was worked up as described leaving a yellow oil that later solidified.

The solid was purified via silica gel flash chromatography using 5% 2M $NH_3$ in methanol in chloroform as the mobile phase. Fractions containing the product were pooled and the solvent removed in vacuo leaving 3'-(2-phenoxy-ethylsulfanylmethyl)-biphenyl-4-carboxylic acid (2-dimethylamino-ethyl)-amide (0.32 g, 34% yield) as a yellow oil which crystallized.

$^1$H NMR (DMSO-d6) δ 8.43 (t, 1H, J=5 Hz), 7.92 (d, 2H, J=8 Hz), 7.73 (d, 2H, J=8 Hz), 7.70 (m, 1H), 7.61 (m, 1H), 7.42 (m, 2H), 7.26 (m, 2H), 6.92 (m, 3H), 4.12 (t, 2H, J=7 Hz), 3.94 (s, 2H), 3.37 (m, 2H), 2.80 (t, 2H, J=7 Hz), 2.41 (t, 2H, J=7 Hz), 2.19 (s, 6H). IR (KBr, cm$^{-1}$) 3302, 2762, 1635, 1540, 1501, 1249, 1037, 750. MS (ES$^+$) m/e 435. Analytical composition calculated for $C_{26}H_{30}N_2O_2S$ C, 71.86; H. 6.96; N, 6.45. Found C, 70.44; H, 6.91; N, 6.22. Analytical HPLC 99% purity. MP 75–78° C.

Example 15

Preparation of 3'-(2-phenoxy-ethylsulfanylmethyl)-biphenyl4-carboxylic acid (3-dimethylamino-propyl)-amide oxalate

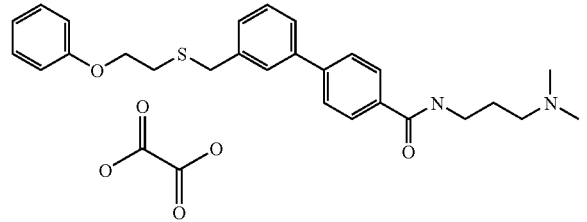

3'-(2-Phenoxy-ethylsulfanylmethyl)-bipheny-4-carboxylic acid (3-dimethylamino-propyl)-amide was synthesized as described for 4'-(2-phenoxy-ethylsulfanylmethyl)-biphenyl-3-carboxylic acid (3-dimethylamino-propyl)-amide. 3'-(2-Phenoxy-ethylsulfanylmethyl)-biphenyl-4carboxylic acid (0.80 g, 2.19 mmol, 1 eq.) in anhydrous THF was treated with 1,1-carbonyldiimidazole (0.36 g, 2.23 mmol, 1.02 eq.) and 3-(dimethylamino)propylamine (0.27 g, 2.63 mmol, 1.2 eq.). When complete, the reaction was worked up as described leaving a yellow oil.

Purified the oil via silica gel flash chromatography using 10% 2M $NH_3$ in methanol in chloroform as the mobile phase. Fractions containing the product were pooled and the solvent removed in vacuo leaving 3'-(2-phenoxy-ethylsulfanylmethyl)-biphenyl-4-carboxylic acid (3-dimethylamino-propyl)-amide (0.87 g, 89% yield) as a faint yellow oil.

The free base was converted to the oxalate salt by adding oxalic acid (1.3 eq, 0.21 g) in EtOAc dropwise to an EtOAc solution of the amine. The resulting solution was treated with diethyl ether and cooled. The resulting white solid was collected by filtration and dried leaving 3'-(2-phenoxy-ethylsulfanylmethyl)-biphenyl-4-carboxylic acid (3-dimethylamino-propyl)-amide oxalate (0.5950 g) as a white solid.

$^1$H NMR (DMSO-d6) δ 8.67 (t, 1H, J=5 Hz), 7.95 (d, 2H, J=8 Hz), 7.75 (d, 2H, J=7 Hz), 7.70 (m, 1H), 7.61 (m, 1H), 7.43 (m, 2H), 7.26 (m, 2H), 6.92 (m, 3H), 4.12 (t, 2H, J=7 Hz), 3.94 (s, 2H), 3.34 (m, 2H), 3.05 (m, 2H), 2.81 (t, 2H, J=7 Hz), 2.74 (s, 6H), 1.89 (m, 2H). IR (KBr, cm$^{-1}$) 3347, 3038, 2940, 1722, 1660, 1644, 1600, 1548, 1490, 1240, 694. MS (ES$^+$) m/e 449. Analytical composition calculated for $C_{29}H_{34}N_2O_6S$ C, 64.66; H, 6.36; N, 5.20. Found C, 64.03; H, 6.36; N, 5.22. Analytical HPLC 100% purity. MP 133–137° C.

Example 16

Preparation of 3'-(2-phenoxy-ethylsulfanylmethyl)-biphenyl4-carboxylic acid (4-dimethylamino-butyl)-amide oxalate

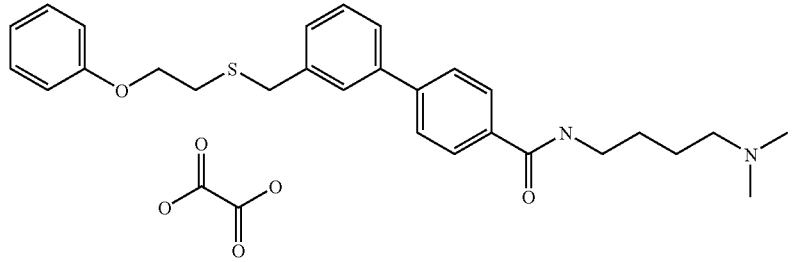

3'-(2-Phenoxy-ethylsulfanylmethyl)-biphenyl-4-carboxylic acid (4-dimethylamino-butyl)-amide was synthesized as described for 4'-(2-phenoxy-ethylsulfanylmethyl)-biphenyl-3-carboxylic acid (3-dimethylamino-propyl)-amide. 3'-(2-Phenoxy-ethylsulfanylmethyl)-biphenyl-4-carboxylic acid (1.50 g, 4.12 mmol, 1 eq.) in anhydrous THF was treated with 1,1-carbonyldiimidazole (0.68 g, 4.20 mmol, 1.02 eq.) and 4-dimethylaminobutylamine (0.57 g, 4.94 mmol, 1.2 eq.). When complete, the reaction was worked up as described leaving a yellow oil.

The oil was purified via silica gel flash chromatography using 5% NH$_3$ in methanol in chloroform as the mobile phase. Fractions containing the product were pooled and the solvent removed in vacuo leaving 3'-(2-phenoxy-ethylsulfanylmethyl)-biphenyl-4-carboxylic acid (4-dimethylaminobutyl)-amide (1.45 g, 76% yield) as a light yellow oil.

The free base was converted to the oxalate salt by adding oxalic acid (0.30 g, 1.05 eq) in EtOAc dropwise to an EtOAc solution of the amine. The resulting white solid was collected by filtration and dried in the vacuum oven.

$^1$H NMR (DMSO-d6) δ 8.59 (t, 1H, J=8 Hz), 7.95 (m, 2H), 7.73 (m, 2H), 7.60 (m, 1H), 7.43 (m, 2H), 7.26 (m, 2H), 7.17 (s, 1H), 6.92 (m, 3H), 4.12 (t, 2H, J=7 Hz), 3.94 (s, 2H), 3.30 (m, 2H), 3.04 (m, 2H), 2.81 (t, 2H, J=7 Hz), 2.73 (s, 6H), 1.60 (m, 4H). IR (CHCl$_3$, cm$^{-1}$) 3441, 3293, 1611, 1602, 1586, 1498, 1231. MS (ES$^+$) m/e 463. MS (ES$^-$) m/e 521 [M+OAc]$^-$, 461. Analytical composition calculated for C$_{30}$H$_{36}$N$_2$O$_6$S C, 65.20; H, 6.57; N, 5.07. Found C, 62.38; H, 6.41; N, 7.86. Analytical HPLC 94.7% purity. MP 85–89° C.

Preparation of 2'-(2-phenoxy-ethylsulfanylmethyl)-biphenyl-2-carboxylic acid from ethyl 2-bromobenzoate and o-tolylboronic acid

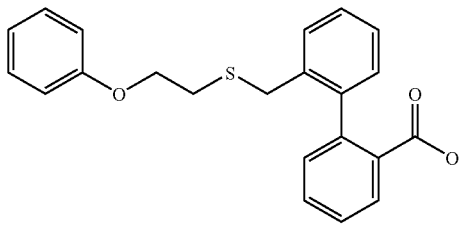

a) 2'-Methyl-biphenyl-2-carboxylic acid ethyl ester

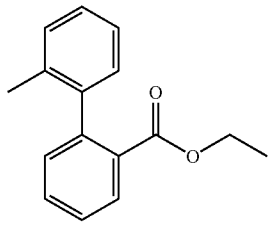

2'-Methyl-biphenyl-2-carboxylic acid ethyl ester was synthesized as described for 4'-methyl-biphenyl-3-carboxylic acid ethyl ester. Ethyl 2-bromobenzoate (9.98 g, 43.57 mmol, 1 eq.) and o-tolylboronic acid (6.22 g, 45.75 mmol, 1.05 eq.) in THF was treated with aqueous 2M sodium carbonate (47.9 mL, 95.85 mmol, 2.2 eq.), palladium(II) acetate (0.98 g, 4.36 mmol, 10 mol %), triphenylphosphine (5.03 g, 19.18 mmol, 4.4×Pd), and copper(I) iodide (0.27, catalyst). When complete, the reaction was worked up as described leaving a dark brown oil.

The oil was purified by silica gel flash chromatography using a step gradient of EtOAc in hexane as the mobile phase. Fractions containing the product were pooled and the solvent removed in vacuo leaving 2'-methyl-biphenyl-2-carboxylic acid ethyl ester (10.45 g, 99% yield) as an orange oil.

$^1$H NMR (DMSO-d6) δ 7.84 (m, 1H), 7.62 (m, 1H), 7.50 (m, 1H), 7.24 (m, 4H), 7.00 (m, 1H), 3.94 (q, 2H, J=7 Hz), 2.01 (s, 3H), 0.86 (t, 3H, J=7 Hz). IR (CHCl$_3$, cm$^{-1}$) 2984, 1709, 1599, 1477, 1368, 1291, 1254, 1135, 1087. MS (EI$^+$) m/e 240. Analytical composition calculated for C$_{16}$H$_{16}$O$_2$ C, 79.97; H, 6.71; N, 0. Found C, 78.01; H, 6.66; N, 0.09.

b) 2'-Bromomethyl-biphenyl-2-carboxylic acid ethyl ester

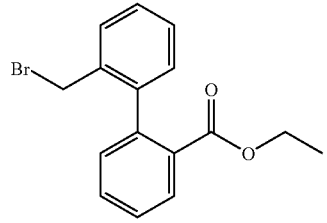

2'-Bromomethyl-biphenyl-2-carboxylic acid ethyl ester was synthesized as described for 4'-bromomethyl-biphenyl-3-carboxylic acid ethyl ester. 2'-Methyl-biphenyl-2-carboxylic acid ethyl ester (10.35 g, 43.07 mmol, 1 eq.) in carbon tetrachloride was treated with N-bromosuccinimide (9.20 g, 51.68 mmol, 1.2 eq.) and 2,2'-azobisisobutyronitrile (0.35 g, 2.15 mmol, 5 mol %). When complete, the reaction was worked up as described leaving an orange oil.

The oil was purified via silica gel flash chromatography using a step gradient of EtOAc in hexane as the mobile phase. Fractions containing the product were pooled and the solvent removed in vacuo leaving 2'-bromomethyl-biphenyl-2-carboxylic acid ethyl ester (13.30, 97% yield) as a yellow oil.

$^1$H NMR (DMSO-d6) δ (complex due to rotational isomerization) 7.93 (m, 1H), 7.62 (m, 3H), 7.36 (m, 3H), 7.07 (m, 1H), 4.48 (d, 1H, J=10 Hz), 4.23 (d, 1H, J=10 Hz), 3.94 (m, 2H), 0.85 (M, 3H). IR (CHCl$_3$, cm$^{-1}$) 1711, 1599, 1475, 1443, 1367, 1291, 1255, 1136. MS (EI$^+$) m/e 239 [M−Br]$^+$. Analytical composition calculated for C$_{16}$H$_{15}$BrO$_2$ C, 60.21; H, 4.74; N, 0. Found C, 56.99; H, 4.30; N, 0.08.

e) 2'-(2-Hydroxy-ethylsulfanylmethyl)-biphenyl-2-carboxylic acid ethyl ester

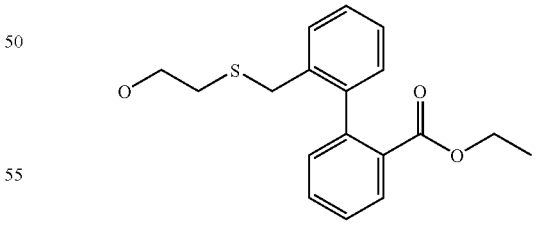

2'-(2-Hydroxy-ethylsulfanylmethyl)-biphenyl-2-carboxylic acid ethyl ester was synthesized as described for 4'-(2-hydroxy-ethylsulfanylmethyl)-biphenyl-3-carboxylic acid ethyl ester. 2'-Bromomethyl-biphenyl-2-carboxylic acid ethyl ester (13.2 g, 41.35 mmol, 1 eq.) in anhydrous DMF was treated with 2-mercaptoethanol (3.88 g, 49.62 mmol, 1.2 eq.) and potassium carbonate (17.14 g, 124.05 mmol, 3 eq.). When complete, the reaction was worked up as described leaving an orange oil.

The oil was purified via silica gel flash chromatography using a step gradient of EtOAc in hexane as the mobile phase. Fractions containing the product were pooled and the solvent removed in vacuo leaving 2'-(2-hydroxy-ethylsulfanylmethyl)-biphenyl-2-carboxylic acid ethyl ester (8.79 g, 67% yield).

$^1$H NMR (DMSO-d6) δ 7.88 (m, 1H), 7.63 (m, 1H), 7.52 (m, 1H), 7.43 (m, 1H), 7.34 (m, 2H), 7.25 (m, 1H), 7.03 (m, 1H), 4.65 (t, 1H, J=5 Hz), 3.93 (q, 2H, J=7 Hz), 3.53 (d, 1H, J=13 Hz), 3.40 (d, 1H, J=13 Hz), 3.32 (m, 2H), 2.38 (m, 2H), 0.85 (t, 3H, J=7 Hz). IR (CHCl$_3$, cm$^{-1}$) 3499, 3019, 3012, 2875, 1709, 1598, 1475, 1444, 1368, 1295, 1254, 1136, 1102, 1052, 1083, 1006. MS (ES$^+$) m/e 317, 334 [M+NH$_4$]$^+$. Analytical composition calculated for C$_{18}$H$_{20}$O$_3$S C, 68.33; H, 6.37; N, 0. Found C, 67.42; H, 5.85; N, 0.

f) 2'-(2-Phenoxy-ethylsulfanylmethyl)-biphenyl-2-carboxylic acid ethyl ester

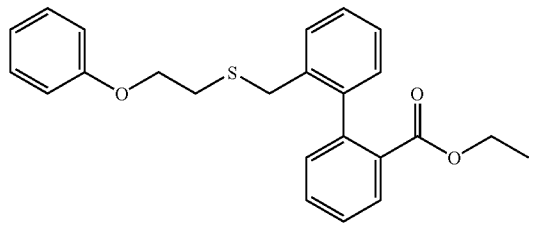

2'-(2-Phenoxy-ethylsulfanylmethyl)-biphenyl-2-carboxylic acid ethyl ester was synthesized as described for 4'-(2-phenoxy-ethylsulfanylmethyl)-biphenyl-3-carboxylic acid ethyl ester. 2'-(2-Hydroxy-ethylsulfanylmethyl)-biphenyl-2-carboxylic acid ethyl ester (5.0 g, 15.80 mmol, 1 eq.) in anhydrous THF was treated with phenol (2.08 g, 22.12 mmol, 1.4 eq.), triphenylphosphine (5.80 g, 22.12 mmol, 1.4 eq.), and diisopropyl azidocarboxylate (4.47 g, 22.12 mmol, 1.4 eq.). When complete, the reaction was worked up as described leaving an orange oil.

The oil was purified via silica gel flash chromatography using a step gradient of EtOAc in hexane as the mobile phase. Fractions containing the product were pooled and the solvent removed in vacuo leaving 2'-(2-phenoxy-ethylsulfanylmethyl)-biphenyl-2-carboxylic acid ethyl ester (4.52 g, 73% yield) as a yellow oil.

$^1$H NMR (DMSO-d6) δ 7.87 (m, 1H), 7.51 (m, 2H), 7.29 (m, 4H), 7.16 (m, 1H), 7.04 (m, 1H), 6.92 (m, 1H), 6.78 (m, 3H), 3.89 (m, 4H), 3.65 (d, 1H, J=13 Hz), 3.52 (d, 1H, J=13 Hz), 2.67 (m, 2H), 0.85 (t, 3H, J=7 Hz). IR (CHCl$_3$, cm_) 1710, 1600, 1498, 1293, 1244. MS (ES$^+$) m/e 393, 410 [M+NH]$^+$. Analytical composition calculated for C$_{24}$H$_{24}$O$_3$S C, 73.44; H, 6.16; N, 0. Found C, 71.91; H, 6.16; N, 0.86.

g) 2'-(2-Phenoxy-ethylsulfanylmethyl)-biphenyl-2-carboxylic acid

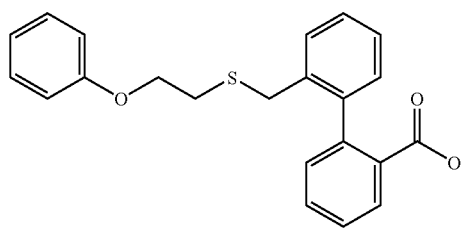

2'-(2-Phenoxy-ethylsulfanylmethyl)-biphenyl-2-carboxylic acid was synthesized as described for 4'-(2-phenoxy-ethylsulfanylmethyl)-biphenyl-3-carboxylic acid. 2'-(2-Phenoxy-ethylsulfanylmethyl)-biphenyl-2-carboxylic acid ethyl ester (4.4 g, 11.21 mmol, 1 eq.) in 30% aqueous THF/dioxane was treated with lithium hydroxide (0.81 g, 33.63 mmol, 3 eq.). When complete, the reaction was worked up as described leaving a brown oil The oil was purified via silica gel flash chromatography using a step gradient of EtOAc in hexane as the mobile phase. Fractions containing the product were pooled and the solvent removed in vacuo leaving 2'-(2-phenoxy-ethylsulfanylmethyl)-biphenyl-2-carboxylic acid (3.65 g, 89% yield) as a red/brown oil.

$^1$H NMR (DMSO-d6) δ 12.58 (s, 1H), 7.87 (m, 1H), 7.49 (m, 3H), 7.27 (m, 4H), 7.06 (m, 1H), 6.92 (m, 1H), 6.78 (m, 3H), 3.85 (t, 2H, J=7 Hz), 3.68 (d, 1H, J=13 Hz), 3.52 (d, 1H, J=13Hz), 2.66 (m, 2H). IR (CHCl$_3$, cm$^{-1}$) 3011, 1701, 1600, 1587, 1573, 1498, 1470, 1301, 801. MS (ES$^+$) m/e 382 [M+NH$_4$]$^+$. MS (ES$^-$) m/e 363.

Example 17

Preparation of 2'-(2-phenoxy-ethylsulfanylmethyl)-biphenyl-2-carboxylic acid (2-dimethylamino-ethyl)-amide oxalate

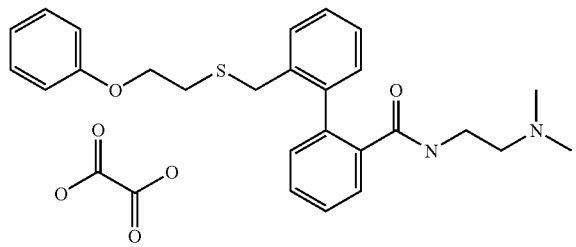

2'-(2-Phenoxy-ethylsulfanylmethyl)-biphenyl-2-carboxylic acid (2-dimethylamino-ethyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-2-carboxylic acid (0.8 g, 2.19 mmol, 1 eq.) in anhydrous THF was treated with 1,1'-carbonyldiimidazole (0.36 g, 2.23 mmol, 1.02 eq.) and warmed as described. The reaction was allowed to cool and then treated with N,N-dimethylethylenediamine (0.23 g, 2.63 mmol, 1.2 eq.). The reaction was treated as described in example 1 to give an orange/brown oil. The oil was purified by silica gel flash chromatography using 10% 2M NH$_3$ in methanol in chloroform as the mobile phase. Fractions containing the product were pooled and the solvent removed in vacuo leaving 2'-(2-phenoxy-ethylsulfanylmethyl)-biphenyl 2-carboxylic acid (2-dimethylamino-ethyl)-amide (0.81 g, 85% yield) as a faint yellow oil.

The free base was converted to the oxalate salt by adding 0.21 g (1.25 eq.) of oxalic acid in EtOAc to an EtOAc/Et$_2$O solution of the amine. After stirring, 2'-(2-phenoxy-ethylsulfanylmethyl)-biphenyl-2-carboxylic acid (2-dimethylamino-ethyl)-amide oxalate (0.81 g) as a white solid was obtained by filtration.

$^1$H NMR (DMSO-d6) δ 8.24 (t, 1H, J=8 Hz), 7.55 (m, 1H), 7.44 (m, 3H), 7.28 (m, 4H), 7.10 (m, 1H), 6.93 (m, 1H), 6.81 (m, 3H), 3.88 (t, 2H, J=7 Hz), 3.73 (d, 1H, J=13 Hz), 3.58 (d, 1H, J=13 Hz), 3.30 (m, 2H), 2.80 (t, 2H, J=7 Hz), 2.69 (m, 2H), 2.60 (s, 6H). IR (KBr, cm$^{-1}$) 3399, 3278, 1703, 1653, 1600, 1586, 1496, 1471, 1302, 1242, 1031, 755. MS (ES$^+$) m/e 435. MS (ES$^-$) m/e 493 [M+OAc]$^-$. Analytical composition calculated for $C_{28}H_{32}N_2O_6S$ C, 64.10; H, 6.15; N, 5.34. Found C, 63.20; H, 5.94; N, 5.31. Analytical HPLC 98.9% purity. MP 46–50° C.

Example 18

Preparation of 2'-(2-phenoxy-ethylsulfanylmethyl)-biphenyl-2-carboxylic acid (3-dimethylamino-propyl)-amide

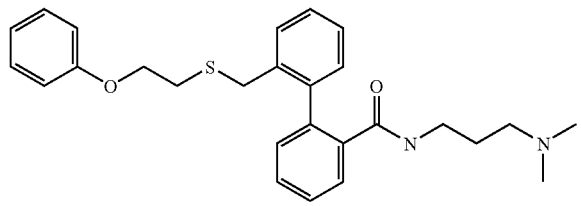

2'-(2-Phenoxy-ethylsulfanylmethyl)-biphenyl-2-carboxylic acid (3-dimethylamino-propyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-2-carboxylic acid (0.7 g, 1.92 mmol, 1 eq.) in anhydrous THF was treated with 1,1-carbonyldiimidazole (0.32 g, 1.96 mmol, 1.02 eq.) and 3-(dimethylamino)propylamine (0.30 g, 2.30 mmol, 1.2 eq.). When complete, the reaction was worked up as described leaving an orange oil.

The oil was purified via silica gel flash chromatography using 5% $NH_3$ in methanol in chloroform as the mobile phase. Fractions containing the product were pooled and the solvent removed in vacuo leaving 2'-(2-phenoxy-ethylsulfanylmethyl)-biphenyl-2-carboxylic acid (3-dimethylamino-propyl)-amide (0.61 g, 71% yield) as a light yellow oil.

$^1$H NMR (DMSO-d6) δ 7.72 (t, 1H, J=8 Hz), 7.43 (m, 4H), 7.28 (m, 5H), 7.11 (m, 1H), 6.92 (m, 1H), 6.81 (m, 2H), 3.88 (t, 2H, J=7 Hz), 3.75 (d, 1H, J=13 Hz), 3.63 (d, 1H, J=13 Hz), 2.96 (m, 2H), 2.69 (m, 2H), 2.01 (s, 6H), 1.95 (t, 2H, J=7 Hz), 1.22 (m, 2H). IR (CHCl$_3$, cm$^{-1}$) 3423, 3311, 1646, 1600, 1497, 1243. MS (ES$^+$) m/e 449. MS (ES$^-$) m/e 507 [M+OAc]$^-$, 447. Analytical composition calculated for $C_{27}H_{32}N_2O_2S$ C, 72.29; H, 7.19; N, 6.24. Found C, 72.00; H, 7.04; N, 6.16. Analytical HPLC 100% purity.

Example 19

Preparation of 2'-(2-phenoxy-ethylsulfanylmethyl)-biphenyl-2-carboxylic acid (4-dimethylamino-butyl)-amide oxalate

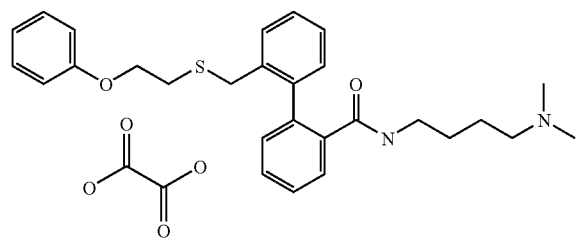

2'-(2-Phenoxy-ethylsulfanylmethyl)-biphenyl-2-carboxylic acid (4-dimethylamino-butyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-2-carboxylic acid (1.0 g, 2.74 mmol, 1 eq.) in anhydrous THF was treated with 1,1-carbonyldiimidazole (0.45 g, 2.79 mmol, 1.02 eq.) and 4-dimethylaminobutylamine (0.35 g, 3.01 mmol, 1.1 eq.). When complete, the reaction was worked up as described leaving a brown oil.

The oil was purified via silica gel flash chromatography using 8% $NH_3$ in methanol in chloroform as the mobile phase. Fractions containing the product were pooled and the solvent removed in vacuo leaving 2'-(2-phenoxy-ethylsulfanylmethyl)-biphenyl-2-carboxylic acid (4-dimethylamino-butyl)-amide (1.23 g, 97% yield) as a faint yellow oil.

The free base was converted to the oxalate salt by adding 0.26 g (1.1 eq.) of oxalic acid in EtOAc to an EtOAc solution of the amine. After stirring, 2'-(2-phenoxy-ethylsulfanylmethyl)-biphenyl-2-carboxylic acid (4-dimethylamino-butyl)-amide oxalate (0.91 g) as a white solid was obtained by filtration.

$^1$H NMR (DMSO-d6) δ 7.91 (t, 1H, J=8 Hz), 7.43 (m, 4H), 7.28 (m, 5H), 7.12 (m, 1H), 6.93 (m, 1H), 6.81 (m, 2H), 3.88 (t, 2H, J=7 Hz), 3.73 (d, 1H, J=13 Hz), 3.61 (d, 1H, J=13 Hz), 2.97 (m, 2H), 2.88 (m, 2H), 2.67 (m, 8H), 1.38 (m, 2H), 1.16 (m, 2H). IR (KBr, cm$^{-1}$) 3409, 3167, 3141, 2944, 1732, 1703, 1601, 1585, 1404, 1229, 711. MS (ES$^+$) m/e 463. Analytical composition calculated for $C_{30}H_{36}N_2O_6S$ C, 65.20; H, 6.57; N; 5.07. Found C, 58.89; H, 5.89; N, 7.87. Analytical HPLC 100% purity. MP 64–70° C.

Preparation of 2'-(2-phenoxy-ethylsulfanylmethyl)-biphenyl-3-carboxylic acid from ethyl 3-bromobenzoate and o-tolylboronic acid

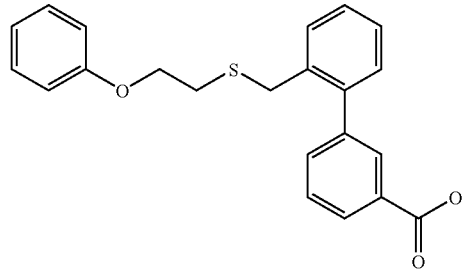

a) 2'-Methyl-biphenyl-3-carboxylic acid ethyl ester

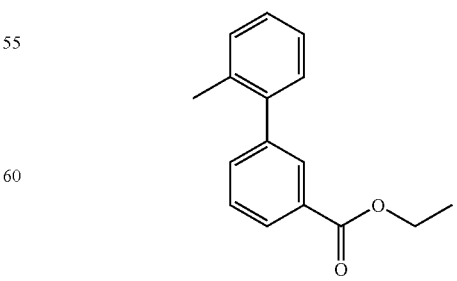

2'-Methyl-biphenyl-3-carboxylic acid ethyl ester was synthesized as described for 4'-methyl-biphenyl-3-carboxylic acid ethyl ester. Ethyl 3-bromobenzoate (8.02 g, 35.03 mmol, 1 eq.) and o-tolylboronic acid (5.0 g, 36.78 mmol, 1.05 eq.) in THF were treated with aqueous 2M sodium carbonate (38.5 mL, 77.07 mmol, 2.2 eq.), palladium(II) acetate (0.79 g, 3.50 mmol, 10 mol %), triphenylphosphine (4.04 g, 15.40 mmol, 4.4×Pd), and copper(I) iodide (0.22 g, catalyst). When complete, the reaction was worked up as described leaving a dark brown oil.

The oil was purified via silica gel flash chromatography using 5% EtOAc in hexane as the mobile phase. Fractions containing the product were pooled and the solvent removed in vacuo leaving 2'-methyl-biphenyl-3-carboxylic acid ethyl ester (8.35 g, 99% yield) as a faint yellow oil.

$^1$H NMR (DMSO-d6) δ 7.97 (m, 1H), 7.88 (s, 1H), 7.62 (m, 2H), 7.29 (m, 4H), 4.33 (q, 2H, J=7 Hz), 2.22 (s, 3H), 1.33 (t, 3H, J=7 Hz). IR (CHCl$_3$, cm$^{-1}$) 1714, 1477, 1308, 1284, 1243, 1226, 1109. MS (ES$^+$) m/e 241. Analytical composition calculated for $C_{16}H_{16}O_2$ C, 79.97; H, 6.71; N, 0. Found C, 79.35; H, 6.45; N, 0.23.

b) 2'-Bromomethyl-biphenyl-3-carboxylic acid ethyl ester

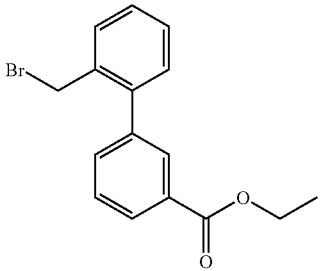

2'-Bromomethyl-biphenyl-3-carboxylic acid ethyl ester was synthesized as described for 4'-bromomethyl-biphenyl-3-carboxylic acid ethyl ester. 2'-Methyl-biphenyl-3-carboxylic acid ethyl ester (8.3 g, 34.54 mmol, 1 eq.) in carbon tetrachloride was treated with N-bromosuccinimide (7.38 g, 41.45 mmol, 1.2 eq.) and 2,2'-azobisisobutyronitrile (0.28 g, 1.73 mmol, 5 mol %). When complete, the reaction was worked up as described leaving an orange oil.

The oil was purified via silica gel flash chromatography using 5% EtOAc in hexane as the mobile phase. Fractions containing the product were pooled and the solvent removed in vacuo leaving 2'-bromomethyl-biphenyl-3-carboxylic acid ethyl ester (10.34 g, 94% yield) as a yellow oil.

$^1$H NMR (DMSO-d6) δ 8.04 (m, 2H), 7.68 (m, 3H), 7.45 (m, 2H), 7.29 (m, 1H), 4.57 (s, 2H), 4.34 (q, 2H, J=7 Hz), 1.33 (t, 3H, J=7 Hz). MS (FD$^+$) m/e 318, 320.

c) 2'-(2-Hydroxy-ethylsulfanylmethyl)-biphenyl-3-carboxylic acid ethyl ester

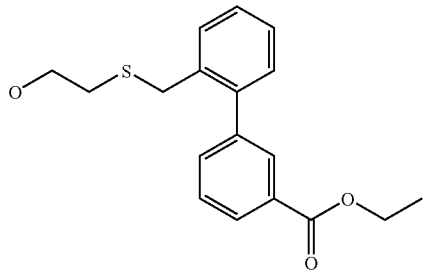

2'-(2-Hydroxy-ethylsulfanylmethyl)-biphenyl-3-carboxylic acid ethyl ester was synthesized as described for 4'-(2-hydroxy-ethylsulfanylmethyl)-biphenyl-3-carboxylic acid ethyl ester. 2'-Bromomethyl-biphenyl-3-carboxylic acid ethyl ester (10.3 g, 32.27 mmol, 1 eq.) in anhydrous DMF was treated with 2-mercaptoethanol (3.03 g, 38.72 mmol, 1.2 eq.) and potassium carbonate (13.38 g, 96.81 mmol, 3 eq.). When complete, the reaction was worked up as described leaving a yellow/orange oil.

The oil was purified via silica gel flash chromatography using a step gradient of EtOAc in hexane as the mobile phase. Fractions containing the product were pooled and the solvent removed in vacuo leaving 2'-(2-hydroxy-ethylsulfanylmethyl)-biphenyl-3-carboxylic acid ethyl ester (8.08 g, 79% yield) as a light yellow oil.

$^1$H NMR (DMSO-d6) δ 7.99 (m, 2H), 7.70 (m, 1H), 7.61 (m, 1H), 7.41 (m, 3H), 7.25 (m, 1H), 4.70 (t, 1H, J=5 Hz), 4.33 (q, 2H, J=7 Hz), 3.68 (s, 2H), 3.39 (m, 2H), 2.46 (m, 2H), 1.33 (t, 3H, J=7 Hz). IR (CHCl$_3$, cm$^{-1}$) 3592, 3518, 1714, 1309, 1296, 1246, 1111. MS (ES$^+$) m/e 334 [M+NH$_4$]$^+$, 299 [M−OH]$^+$. Analytical composition calculated for $C_{18}H_{20}O_3S$ C, 68.33; H, 6.37; N, 0. Found C, 68.01; H, 6.09; N, 0.44.

d) 2'-(2-Phenoxy-ethylsulfanylmethyl)-biphenyl-3-carboxylic acid ethyl ester

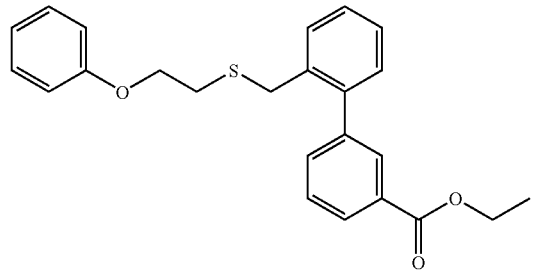

2'-(2-Phenoxy-ethylsulfanylmethyl)-biphenyl-3-carboxylic acid ethyl ester was synthesized as described for 4'-(2-phenoxy-ethylsulfanylmethyl)-biphenyl-3-carboxylic acid ethyl ester. 2'-(2-Hydroxy-ethylsulfanylmethyl)-biphenyl-3-carboxylic acid ethyl ester (4.0 g, 12.64 mmol, 1 eq.) in anhydrous THF was treated with phenol (1.67 g, 17.70 mmol, 1.4 eq.), triphenylphosphine (4.64 g, 17.70 mmol, 1.4 eq.), and diisopropyl azidocarboxylate (3.58 g, 17.70 mmol, 1.4 eq.). When complete, the reaction was worked up as described leaving a yellow oil.

The oil was purified via silica gel flash chromatography using 10% EtOAc in hexane as the mobile phase. Fractions containing the product were pooled and the solvent removed in vacuo leaving 2'-(2-phenoxy-ethylsulfanylmethyl)-biphenyl-3-carboxylic acid ethyl ester (3.74 g, 75% yield) as a light yellow oil.

$^1$H NMR (DMSO-d6) δ 7.96 (m, 2H), 7.69 (m, 1H), 7.54 (m, 2H), 7.38 (m, 2H), 7.25 (m, 3H), 6.92 (m, 1H), 6.76 (m, 2H), 4.30 (q, 2H, J=7 Hz), 3.92 (t, 2H, J=7 Hz), 3.80 (s, 2H), 2.75 (t, 2H, J=7 Hz), 1.30 (t, 3H, J=7 Hz). IR (CHCl$_3$, cm$^{-1}$) 1714, 1600, 1498, 1309, 1297, 1244, 1227, 1225. MS (FD$^+$) m/e 392. Analytical composition calculated for $C_{24}H_{24}O_3S$ C, 73.44; H, 6.16; N, 0. Found C, 71.34; H. 5.88; N, 0.35.

e) 2'-(2-Phenoxy-ethylsulfanylmethyl)-biphenyl-3-carboxylic acid

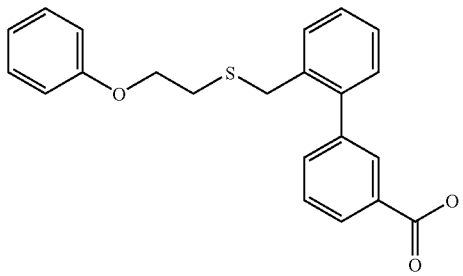

2'-(2-Phenoxy-ethylsulfanylmethyl)-biphenyl-3-carboxylic acid was synthesized as described for 4'-(2-phenoxy-ethylsulfanylmethyl)-biphenyl-3-carboxylic acid. 2'-(2-Phenoxy-ethylsulfanylmethyl)-biphenyl-3-carboxylic acid ethyl ester (3.65 g, 9.30 mmol, 1 eq.) in 30% aqueous THF was treated with lithium hydroxide (0.67 g, 27.9 mmol, 3 eq.). When complete, the reaction was worked up as described leaving 2'-(2-phenoxy-ethylsulfanylmethyl)-biphenyl-3-carboxylic acid (3.39 g, 100% yield) as an off-white solid.

$^1$H NMR (DMSO-d6) δ 13.04 (s, 1H), 7.96 (m, 2H), 7.66 (m, 1H), 7.52 (m, 2H), 7.37 (m, 2H), 7.25 (m, 3H), 6.92 (m, 1H), 6.78 (m, 2H), 3.93 (t, 2H, J=7 Hz), 3.80 (s, 2H), 2.75 (t, 2H, J=7 Hz). IR (CHCl$_3$, cm$^{-1}$) 1695, 1601, 1498, 1303, 1244. MS (ES$^+$) m/e 382 [M+NH$_4$]$^+$. MS (ES$^-$) m/e 363. Analytical composition calculated for C$_{22}$H$_{20}$O$_3$S C, 72.51; H, 5.53; N, 0. Found C, 72.55; H, 5.71; N, 0.42.

Example 20

Preparation of 2'-(2-phenoxy-ethylsulfanylmethyl)-biphenyl-3-carboxylic acid (2-dimethylamino-ethyl)-amide oxalate

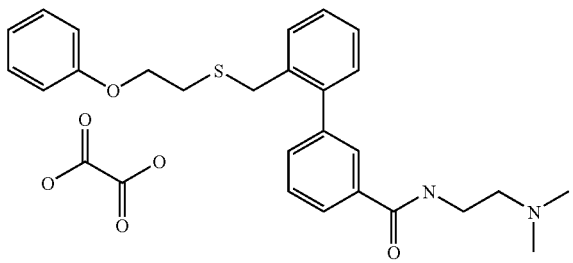

2'-(2-Phenoxy-ethylsulfanylmethyl)-biphenyl-3-carboxylic acid (2-dimethylamino-ethyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-3-carboxylic acid (1.0 g, 2.74 mmol, 1 eq.) in anhydrous THF was treated with 1,1-carbonyldiimidazole (0.45 g, 2.79 mmol, 1.02 eq.) followed by N,N-dimethylethylenediamine (0.29 g, 3.29 mmol, 1.2 eq.) as described. When complete, the reaction was worked up as described leaving a yellow oil.

The oil was purified via silica gel flash chromatography using 10% 2M NH$_3$ in methanol in chloroform as the mobile phase. Fractions containing the product were pooled and the solvent removed in vacuo leaving 2'-(2-phenoxy-ethylsulfanylmethyl)-biphenyl-3-carboxylic acid (2-dimethylamino-ethyl)-amide (1.04 g, 87% yield). The free base was converted to the oxalate salt by adding oxalic acid (0.24 g, 1.1 eq.) in EtOAc dropwise to an EtOAc solution of the free base. 2'-(2-Phenoxy-ethylsulfanylmethyl)-biphenyl-3-carboxylic acid (2-dimethylamino-ethyl)-amide oxalate (0.88 g) was collected by filtration as a white solid.

$^1$H NMR (DMSO-d6) δ 8.77 (t, 1H, J=8 Hz), 7.88 (m, 2H), 7.61 (m, 1H), 7.51 (m, 2H), 7.37 (m, 2H), 7.26 (m, 3H), 6.93 (m, 1H), 6.80 (m, 2H), 3.93 (t, 2H, J=7 Hz), 3.82 (s, 2H), 3.59 (m, 2H), 3.16 (t, 2H, J=7 Hz), 2.75 (m, 8H). IR (KBr, cm$^{-1}$) 3362, 1640, 1600, 1545, 1243, 702, 693. MS (ES$^+$) m/e 435. MS (ES$^-$) m/e 493 [M+OAc]$^{-1}$. Analytical composition calculated for C$_{28}$H$_{32}$N$_2$O$_6$S C, 64.10; H, 6.15; N, 5.34; S, 6.11. Found C, 63.99; H, 6.12; N, 5.37; S, 6.17. Analytical HPLC 98.3% purity. MP 96–100° C.

Example 21

Preparation of 2'-(2-phenoxy-ethylsulfanylmethyl)-biphenyl-3-carboxylic acid (3-dimethylamino-propyl)-amide oxalate

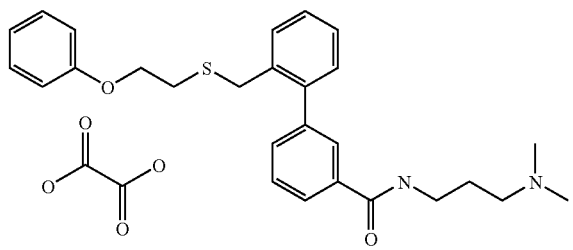

2'-(2-Phenoxy-ethylsulfanylmethyl)-biphenyl-3-carboxylic acid (3-dimethylamino-propyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-3-carboxylic acid (1.0 g, 2.74 mmol, 1 eq.) in anhydrous THF was treated with 1,1-carbonyldiimidazole (0.45 g, 2.79 mmol, 1.02 eq.) followed by 3-(dimethylamino)propylamine (0.34 g, 3.29 mmol, 1.2 eq.) as described. When complete, the reaction was worked up leaving a yellow oil. The oil was purified via silica gel flash chromatography using 10% 2M NH$_3$ in methanol in chloroform as the mobile phase. Fractions containing the product were pooled and the solvent removed in vacuo leaving 2'-(2-phenoxy-ethylsulfanylmethyl)-biphenyl-3-carboxylic acid (3-dimethylamino-propyl)-amide (1.06 g, 86% yield). The free base was converted to the oxalate salt by adding oxalic acid (0.26 g, 1.2 eq.) in EtOAc dropwise to an EtOAc solution of the free base. 2'-(2-Phenoxy-ethylsulfanylmethyl)-biphenyl-3-carboxylic acid (3-dimethylamino-propyl)-amide oxalate (1.08 g) was collected by filtration as a white solid.

$^1$H NMR (DMSO-d6) δ 8.67 (t, 1H, J=8 Hz), 7.87 (m, 2H), 7.59 (m, 1H), 7.50 (m, 2H), 7.38 (m, 2H), 7.26 (m, 3H), 6.93 (m, 1H), 6.80 (m, 2H), 3.93 (t, 2H, J=7 Hz), 3.82 (s, 2H), 3.33 (m, 2H), 3.05 (m, 2H), 2.73 (m, 8H), 1.87 (m, 2H). IR (KBr, cm$^{-1}$) 3384, 1718, 1645, 1601, 1584, 1535, 1497, 1474, 1243, 1231, 1200, 1176, 705. MS (ES$^+$) m/e 449. MS (ES$^-$) m/e 507 [M+OAc]$^-$. Analytical composition calculated for C$_{29}$H$_{34}$N$_2$O$_6$S C, 64.66; H, 6.36; N, 5.20; S, 5.95. Found C, 62.39; H, 6.17; N, 6.22; S, 6.05. Analytical HPLC 98.8% purity. MP 97–100° C. to a glass then 125–128° C.

Example 22

Preparation of 2'-(2-phenoxy-ethylsulfanylmethyl)-biphenyl-3-carboxylic acid (4-dimethylamino-butyl)-amide oxalate

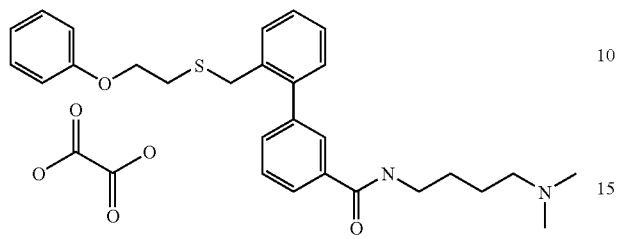

2'-(2-Phenoxy-ethylsulfanylmethyl)-biphenyl-3-carboxylic acid (4-dimethylamino-butyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-3-carboxylic acid (0.50 g, 1.37 mmol, 1 eq.) in anhydrous THF was treated with 1,1-carbonyldiimiidazole (0.23g, 1.40 mmol, 1.02 eq.) followed by 4-dimethylaminobutylamine (0.19 g, 1.64 mmol, 1.2 eq.) as described. When complete, the reaction was worked up leaving a yellow oil. The oil was purified via silica gel flash chromatography using 10% 2M $NH_3$ in methanol in chloroform as the mobile phase. Fractions containing the product were pooled and the solvent removed in vacuo leaving 2'-(2-phenoxy-ethylsulfanylmethyl)-biphenyl-3-carboxylic acid (4-dimethylamino-butyl)-amide (0.31 g, 49% yield). The free base was converted to the oxalate salt by adding oxalic acid (0.07g, 1. 1 eq.) in EtOAc dropwise to an EtOAc solution of the free base. 2'-(2-Phenoxy-ethylsulfanylmethyl)-biphenyl-3-carboxylic acid (4-dimethylamino-butyl)-amide oxalate (0.28 g) was collected by filtration as a white solid.

$^1$H NMR (DMSO-d6) δ 8.59 (t, 1H, 3=8 Hz), 7.86 (m, 2H), 7.57 (m, 1H), 7.50 (m, 2H), 7.37 (m, 2H), 7.26 (m, 3H), 6.92 (m, 1H), 6.80 (m, 2H), 3.92 (t, 2H, J=7 Hz), 3.82 (s, 2H), 3.28 (m, 2H), 3.02 (m, 2H), 2.72 (m, 8H), 1.64 (m, 2H), 1.54 (m, 2H). IR (KBr, cm$^{-1}$) 3381, 1723, 1638, 1601, 1584, 1536, 1231, 702. MS (ES$^+$) m/e 463. MS (ES$^-$) m/e 521 [M+OAc]$^-$. Analytical composition calculated for $C_{30}H_{36}N_2O_6S$ C, 65.20; H, 6.57; N, 5.07. Found C, 60.00; H, 5.94; N, 7.06. Analytical HPLC 96.8% purity. MP 96–104° C.

Preparation of 2'-(2-phenoxy-ethylsulfanylmethyl)-biphenyl4-carboxylic acid from ethyl 4-iodobenzoate and o-tolylboronic acid

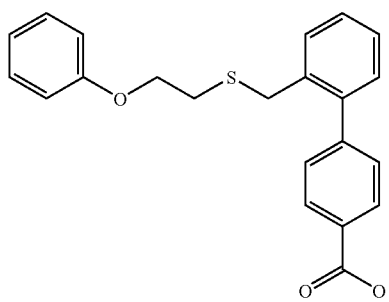

a) 2'-Methyl-biphenyl4-carboxylic acid ethyl ester

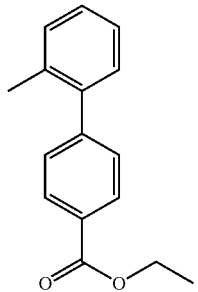

2'-Methyl-biphenyl-4-carboxylic acid ethyl ester was synthesized as described for 4'-methyl-biphenyl-3-carboxylic acid ethyl ester. Ethyl 4-iodobenzoate (6.09 g, 22.06 mmol, 1 eq.) and o-tolylboronic acid (3.3 g, 24.27 mmol, 1.1 eq.) in THF were treated with aqueous 2M sodium carbonate (24.27 mL, 48.53 mmol, 2.2 eq.), palladium(II) acetate (0.50 g, 2.21 mmol, 10 mol %), triphenylphosphine (2.55 g, 9.72 mmol, 4.4×Pd) and copper(I) iodide (0.15 g, catalyst). When complete, the reaction was worked up as described leaving a dark orange oil.

The oil was purified via preparative HPLC using a gradient of EtOAc in hexane as the mobile phase. Fractions containing the product were pooled and the solvent removed in vacuo leaving 2'-methyl-biphenyl-4-carboxylic acid ethyl ester (4.82 g, 91% yield) as an orange oil.

$^1$H NMR (DMSO-d6) δ 8.02 (d, 2H, J=8 Hz), 7.49 (d, 2H, J=8 Hz), 7.29 (m, 4H), 4.34 (q, 2H, J=7 Hz), 2.23 (s, 3H), 1.35 (t, 3H, J=7 Hz). IR (CHCl$_3$, cm$^{-1}$) 1710, 1611, 1280, 1112, 1102. MS (FD$^+$) m/e 240. Analytical composition calculated for $C_{16}H_{16}O_2$ C, 79.97; H, 6.71; N, 0. Found C, 79.66; H, 6.50; N, 0.32.

b) 2'-Bromomethyl-biphenyl-4-carboxylic acid ethyl ester

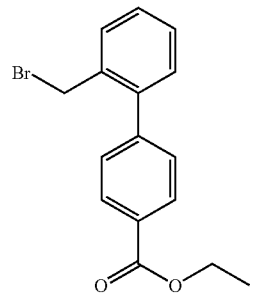

2'-Bromomethyl-biphenyl4-carboxylic acid ethyl ester was synthesized as described for 4'-bromomethyl-biphenyl-3-carboxylic acid ethyl ester. 2'-Methyl-biphenyl-4-carboxylic acid ethyl ester (4.4 g, 18.31 mmol, 1 eq.) in carbon tetrachloride was treated with N-bromosuccinimide (3.58 g, 20.14 mmol, 1.1 eq.), and 2,2'-azobisisobutyronitrile (0.15 g, 0.92 mmol, 5 mol %). When complete, the reaction was worked up as described leaving 2'-bromomethyl-biphenyl-4-carboxylic acid ethyl ester (5.77 g, 99% yield) as a yellow oil.

$^1$H NMR (DMSO-d6) δ 8.08 (m, 2H), 7.60 (m, 3H), 7.46 (m, 2H), 7.28 (m, 1H), 4.60 (s, 2H), 4.34 (m, 2H), 1.35 (t, 3H, J=7 Hz). IR (CHCl$_3$, cm$^{-1}$) 2980, 1713, 1613, 1369, 1310, 1279, 1180, 1104, 1007. MS (FD$^+$) m/e 318, 320.

c) 2'-(2-Hydroxy-ethylsulfanylmethyl)-biphenyl4-carboxylic acid ethyl ester

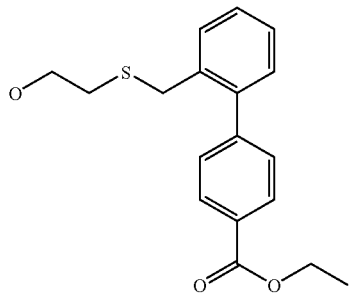

2'-(2-Hydroxy-ethylsulfanylmethyl)-biphenyl-4-carboxylic acid ethyl ester was synthesized as described for 4'-(2-hydroxy-ethylsulfanylmethyl)-biphenyl-3-carboxylic acid ethyl ester. 2'-Bromomethyl-biphenyl-4-carboxylic acid ethyl ester (5.77 g, 18.1 mmol, 1 eq.) in anhydrous DMF was treated with 2-mercaptoethanol (2.83 g, 36.2 mmol, 2 eq.) and potassium carbonate (7.50 g, 54.3 mmol, 3 eq.). When complete, the reaction was worked up as described leaving a yellow oil The oil was purified via silica gel flash chromatography using a step gradient of EtOAc in hexane as the mobile phase. Fractions containing the product were pooled and the solvent removed in vacuo leaving 2'-(2-hydroxy-ethylsulfanylmethyl)-biphenyl-4-carboxylic acid ethyl ester (4.38 g, 76% yield) as a yellow oil.

$^1$H NMR (DMSO-d6) δ 8.03 (d, 2H, J=8 Hz), 7.56 (d, 2H, J=8 Hz), 7.48 (m, 1H), 7.37 (m, 2H), 7.24 (m, 1H), 4.70 (t, 1H, J=5 Hz), 4.34 (q, 2H, J=7 Hz), 3.70 (s, 2H), 3.37 (m, 2H), 2.44 (t, 2H, J=7 Hz), 1.35 (t, 3H, J=7 Hz). IR (CHCl$_3$, cm$^{-1}$) 3599, 3506, 1711, 1611, 1369, 1310, 1279, 1113, 1103, 1056, 1007. MS (FD$^+$) m/e 316. Analytical composition calculated for C$_{18}$H$_{20}$O$_3$S C, 68.33; H, 6.37; N, 0. Found C, 66.50; H, 6.06; N, 0.22.

f) 2'-(2-Phenoxy-ethylsulfanylmethyl)-biphenyl4-carboxylic acid ethyl ester

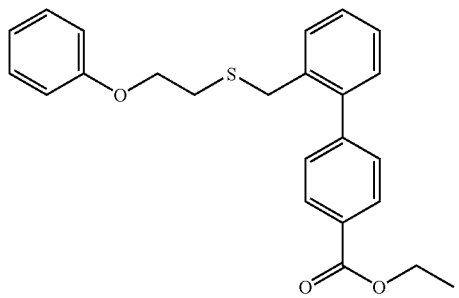

2'-(2-Phenoxy-ethylsulfanylmethyl)-biphenyl-4-carboxylic acid ethyl ester was synthesized as described for 4'-(2-phenoxy-ethylsulfanylmethyl)-biphenyl-3-carboxylic acid ethyl ester. 2'-(2-Hydroxy-ethylsulfanylmethyl)-biphenyl4-carboxylic acid ethyl ester (4.15 g, 13.12 mmol, 1 eq.) in anhydrous THF was treated with phenol (1.61 g, 17.06 mmol, 1.3 eq.), triphenylphosphine (4.47 g, 17.06 mmol, 1.3 eq.), and diisopropyl azidocarboxylate (3.45 g, 17.06 mmol, 1.3 eq.). When complete, the reaction was worked up as described leaving a yellow oil.

The oil was purified via silica gel flash chromatography using 10% EtOAc in hexane as the mobile phase. Fractions containing the product were pooled and the solvent removed in vacuo leaving 2'-(2-phenoxy-ethylsulfanylmethyl)-biphenyl-4-carboxylic acid ethyl ester (4.84 g, 94% yield) as a yellow oil.

1H NMR (DMSO-d6) d7.97 (d, 2H, J=8 Hz), 7.54 (m, 3H), 7.38 (m, 2H), 7.24 (m, 3H), 6.92 (m, 1H), 6.76 (m, 2H), 4.32 (q, 2H, J=7 Hz), 3.89 (t, 2H, J=7 Hz), 3.83 (s, 2H), 2.72 (t, 2H, J=7 Hz), 1.34 (t, 3H, J=7 Hz). IR (CHCl$_3$, cm$^{-1}$) 1711, 1600, 1498, 1279, 1243, 1179, 1104. MS (FD$^+$) m/e 392. Analytical composition calculated for C$_{24}$H$_{24}$O$_3$S C, 73.44; H, 6.16; N, 0. Found C, 71.27; H, 5.96; N, 1.01.

e) 2'-(2-Phenoxy-ethylsulfanylmethyl)-biphenyl-4-carboxylic acid

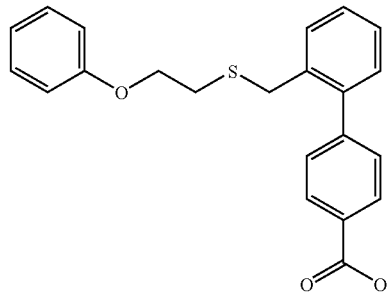

2'-(2-Phenoxy-ethylsulfanylmethyl)-biphenyl-4-carboxylic acid was synthesized as described for 4'-(2-phenoxy-ethylsulfanylmethyl)-biphenyl-3-carboxylic acid. 2'-(2-Phenoxy-ethylsulfanylmethyl)-biphenyl-4-carboxylic acid ethyl ester (4.75 g, 12.10 mmol, 1 eq.) in 30% aqueous THF was treated with lithium hydroxide (0.87 g, 36.30 mmol, 3 eq.). When complete, the reaction was worked up as described leaving a tan solid.

The solid was purified via silica gel flash chromatography using 60% EtOAc in hexane as the mobile phase. Fractions containing the product were pooled and the solvent removed in vacuo leaving 2'-(2-phenoxy-ethylsulfanylmethyl)-biphenyl-4-carboxylic acid (3.35 g, 76% yield) as an off-white solid.

$^1$H NMR (DMSO-d6) δ 12.98 (s, 1H), 7.99 (d, 2H, J=8 Hz), 7.52 (m, 3H), 7.38 (m, 2H), 7.25 (m, 3H), 6.92 (m, 1H), 6.77 (m, 2H), 3.90 (t, 2H, J=7 Hz), 3.83 (s, 2H), 2.73 (t, 2H, J=7 Hz). IR (CHCl$_3$, cm$^{-1}$) 1678, 1609, 1601, 1498, 1324, 1293, 1245, 749. MS (ES$^-$) m/e 363. Analytical composition calculated for C$_{22}$H$_{20}$O$_3$S C, 72.50; H, 5.53; N, 0. Found C, 71.86; H, 5.17; N, 0.22.

Example 23

Preparation of 2'-(2-phenoxy-ethylsulfanylmethyl)-biphenyl4-carboxylic acid (2-dimethylamino-ethyl)-amide

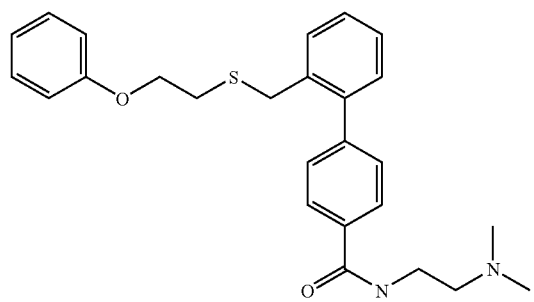

2'-(2-Phenoxy-ethylsulfanylmethyl)-biphenyl-4-carboxylic acid (2-dimethylamino-ethyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-4-carboxylic acid (0.80 g, 2.19 mmol, 1 eq.) in anhydrous THF was treated with 1,1-carbonyldiimidazole (0.36 g, 2.23 mmol, 1.02 eq.) followed by N,N-dimethylethylenediamine (0.23 g, 2.63 mmol, 1.2 eq.) as described. When complete, the reaction was worked up leaving a yellow oil. The oil was purified via silica gel flash chromatography using 140:10:1 (CHCl$_3$/MeOH/NH$_4$OH) as the mobile phase. Fractions containing the product were pooled and the solvent removed in vacuo leaving 2'-(2-phenoxy-ethylsulfanylmethyl)-biphenyl-4-carboxylic acid (2-dimethylamino-ethyl)-amide (0.95 g, 100% yield) as a yellow oil. Recrystallized from diethyl ether to obtain 2'-(2-phenoxy-ethylsulfanylmethyl)-biphenyl-4-carboxylic acid (2-dimethylamino-ethyl)-amide (0.49 g) as a white solid that was collected by filtration.

$^1$H NMR (DMSO-d6) δ8.41 (t, 1H, J=8 Hz), 7.90 (d, 2H, J=8 Hz), 7.50 (m, 3H), 7.37 (m, 2H), 7.25 (m, 3H), 6.91 (m, 1H), 6.78 (m, 2H), 3.91 (t, 2H, J=7 Hz), 3.83 (s, 2H), 3.38 (m, 2H), 2.73 (t, 2H, J=7 Hz), 2.42 (t, 2H, J=7 Hz), 2.19 (s, 6H). IR (CHCl$_3$, cm$^{-1}$) 3395, 1651, 1601, 1527, 1498, 1481, 1243. MS (ES$^+$) m/e 435. MS (ES$^-$) m/e 433. Analytical composition calculated for C$_{26}$H$_{30}$N$_2$O$_2$S C, 71.86; H, 6.96; N, 6.45. Found C, 71.58; H, 6.90; N, 6.36. Analytical HPLC 97.9% purity. MP 93–96° C.

Example 24

Preparation of 2'-(2-phenoxy-ethylsulfanylmethyl)-biphenyl4-carboxylic acid (3-dimethylamino-propyl)-amide

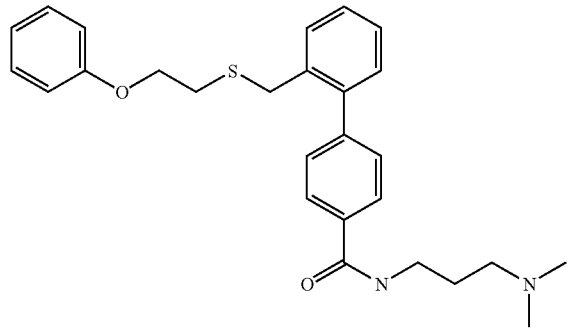

2'-(2-Phenoxy-ethylsulfanylmethyl)-biphenyl-4-carboxylic acid (3-dimethylamino-propyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-4-carboxylic acid (0.80 g, 2.19 mmol, 1 eq.) in anhydrous THF was treated with 1,1-carbonyldiimidazole (0.36g, 2.23 mmol, 1.02 eq.) followed by 3-(dimethylamino)propylamine (0.27 g, 2.63 mmol, 1.2 eq.) as described. When complete, the reaction was worked up leaving a yellow oil that later crystallized. The solid was purified via silica gel flash chromatography using 140:10:1 (CHCl$_3$/MeOH/NH$_4$OH) as the mobile phase. Fractions containing the product were pooled and the solvent removed leaving 2'-(2-phenoxy-ethylsulfanylmethyl)-biphenyl-4-carboxylic acid (3-dimethylamino-propyl)-amide (0.72 g, 74% yield) as a white solid.

$^1$H NMR (DMSO-d6) δ 8.53 (t, 1H, J=8 Hz), 7.89 (d, 2H, J=8 Hz), 7.50 (m, 3H), 7.37 (m, 2H), 7.24 (m, 3H), 6.91 (m, 1H), 6.78 (m, 2H), 3.91 (t, 2H, J=7 Hz), 3.83 (s, 2H), 3.30 (m, 2H), 2.73 (t, 2H, J=7 Hz), 2.27 (t, 2H, J=7 Hz), 2.14 (s, 6H), 1.67 (m, 2H). IR (CHCl$_3$, cm$^{-1}$) 3308, 3059, 2968, 2763, 1630, 1540, 1499, 1247, 1035, 745. MS (ES$^+$) m/e 449. MS (ES$^-$) m/e 447. Analytical composition calculated for C$_{27}$H$_{32}$N$_2$O$_2$S C, 72.29; H, 7.19; N, 6.24. Found C, 71.41; H, 6.91; N, 6.36. Analytical HPLC 97.5% purity. MP 98–100° C.

Example 25

Preparation of 2'-(2-phenoxy-ethylsulfanylmethyl)-biphenyl4-carboxylic acid (4-dimethylamino-butyl)-amide

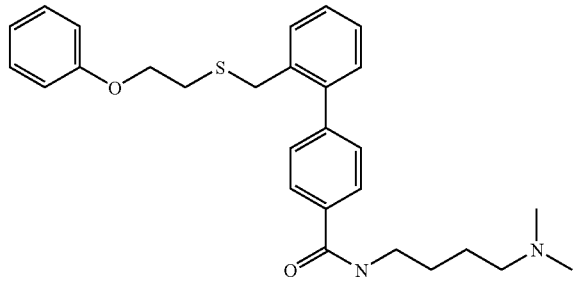

2'-(2-Phenoxy-ethylsulfanylmethyl)-biphenyl-4-carboxylic acid (4-dimethylamino-butyl)-amide was synthesized as described for 4'-(2-phenoxy-ethylsulfanylmethyl)-biphenyl-3-carboxylic acid (3-dimethylamino-propyl)-amide. 2'-(2-Phenoxy-ethylsulfanylmethyl)-biphenyl-4-carboxylic acid (0.80 g, 2.19 mmol, 1 eq.) in anhydrous THF was treated with 1,1-carbonyldiimidazole (0.36g, 2.23 mmol, 1.02 eq.) followed by 4-dimethylaminobutylamine (0.31 g, 2.63 mmol, 1.2 eq.) as described. When complete, the reaction was worked up leaving a yellow oil that later crystallized. The solid was purified via silica gel flash chromatography using 5% 2M NH$_3$ in methanol in chloroform as the mobile phase. Fractions containing the product were pooled and the solvent removed in vacuo leaving 2'-(2-phenoxy-ethylsulfanylmethyl)-biphenyl-4-carboxylic acid (4-dimethylaminobutyl)-amide (0.63 g, 62% yield) as a white solid.

$^1$H NMR (DMSO-d6) δ 8.51 (t, 1H, J=8 Hz), 7.90 (d, 2H, J=8 Hz), 7.50 (m, 3H), 7.37 (m, 2H), 7.25 (m, 3H), 6.91 (m, 1H), 6.78 (m, 2H), 3.91 (t, 2H, J=7 Hz), 3.83 (s, 2H), 3.30 (m, 2H), 2.73 (t, 2H, J=7 Hz), 2.22 (t, 2H, J=7 Hz), 2.11 (s, 6H), 1.49 (m, 4H). IR (KBr, cm$^{-1}$) 3315, 3065, 2921, 2757, 1638, 1542, 1240, 1034, 754. MS (MS$^+$) 463. MS (ES$^-$) 521 [M+OAc]$^{-1}$. Analytical composition calculated for C$_{28}$H$_{34}$N$_2$O$_2$S C, 72.69; H, 7.41; N, 6.05. Found C, 72.46; H, 7.49; N, 6.40. Analytical HPLC 94.7% purity. MP softening staring at 65° C. then 72–75° C.

We claim:
1. A compound of formula I:

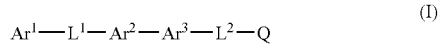

(I)

or a pharmaceutically acceptable salt, solvate, enantiomer, mixture of diastereomers, or prodrug thereof; wherein Ar¹ is phenyl optionally substituted with one to five groups selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, aryl, $C_3$–$C_8$ cycloalkyl, $C_1$–$C_8$ alkylcycloalkyl, cyano, —$(CH_2)_nNR^1R^2$, $C_1$–$C_8$ haloalkyl, halo, $(CH_2)_nCOR^6$, $(CH_2)_nNR^5SO_2R^6$, —$(CH_2)_nC(O)NR^1R^2$, and $C_1$–$C_8$ alkylheterocyclic;

$L^1$ is $OCH_2CH_2SCH_2$ or $SCH_2$;

Ar² is phenyl optionally substituted with one to three substitutents selected from $C_1$–$C_8$ alkyl, $C_2$–$C_8$ alkenyl, $C_2$–$C_8$ alkynyl, hydroxy, $C_1$–$C_8$ alkoxy, $C_1$–$C_8$ alkylaryl, phenyl, aryl, $C_3$–$C_8$ cycloalkyl, $C_1$–$C_8$ alkylcycloalkyl, cyano, $C_1$–$C_8$ haloalkyl, halo, $(CH_2)_nC(O)R^6$, $(CH_2)_nC(O)OR^6$, $(CH_2)_nNR^5SO_2R^6$, $(CH_2)_nC(O)NR^1R^2$, and $C_1$–$C_8$ alkylheterocyclic;

Ar³ is phenyl optionally substituted with one to three substitutents independently selected from halo, —$NHR^5$, $C_1$–$C_8$ haloalkyl, $C_3$–$C_8$ cycloalkyl, $C_1$–$C_8$ alkyl, hydroxy, alkoxy, $(CH_2)_nC(O)R^6$, $(CH_2)_nC(O)OR^6$, $(CH_2)_nNR^5SO_2R^6$, $(CH_2)_nC(O)NR^1R^2$, phenyl, $C_1$–$C_8$ alkylaryl, and aryl; provided that Ar² and Ar³ or positional isomers thereof are linked by a bond;

$L^2$ is $CONHCH_2CH_2$, $CONHCH_2CH_2CH_2$ or $CONHCH_2CH_2CH_2$;

Q is a group represented by —$NR^1R^2$; wherein

R¹ and R² are independently selected from hydrogen, $C_1$–$C_8$ alkyl, $C_2$–$C_8$ alkenyl, $C_3$–$C_8$ cycloalkane, $C_1$–$C_8$ alkylaryl, —$C(O)C_1$–$C_8$ alkyl, —$C(O)OC_1$–$C_8$ alkyl, $C_1$–$C_8$ alkylcycloalkane, $(CH_2)_nC(O)OR^5$, $(CH_2)_nC(O)R^5$, $(CH_2)_nC(O)NR^1R^2$, and $(CH_2)_nNSO_2R^5$; and wherein R¹ and R² may combine together, and with the nitrogen atom to which they are attached or with 0, 1, or 2 atoms adjacent to the nitrogen atom to form a nitrogen containing heterocycle which may have substituents;

R⁵ is hydrogen, $C_1$–$C_8$ alkyl, $C_2$–$C_8$ alkenyl; and

R⁶ is a group independently selected from hydrogen, $C_1$–$C_8$ alkyl, and $C_3$–$C_8$ cycloalkyl;

wherein m is an integer from 0 to 4; and n is an integer from 0 to 3.

2. A compound according to claim 1 wherein for Q, R¹ and R² combine to form piperidinyl, pyrrolidinyl, azepine, or azetidinyl.

3. A compound according to claim 1 wherein R¹ and R² are independently selected from the group consisting of hydrogen, methyl, ethyl, propyl, isopropyl, methylcyclopentane, methylcyclohexane, phenyl, 2-fluorophenyl, benzyl, and C(O)Me.

4. A compound selected from the group consisting of:

4'-(2-phenoxy-ethylsulfanylmethyl)-biphenyl-3-carboxylic acid (3-dimethylamino-propyl)-amide oxalate

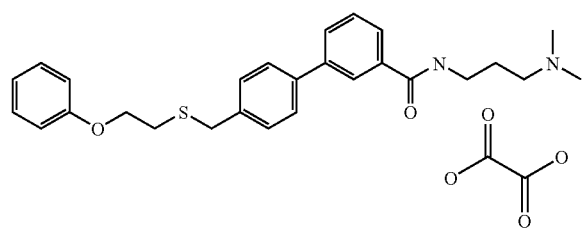

4'-(2-phenoxy-ethylsulfanylmethyl)-biphenyl-3-carboxylic acid (2-dimethylamino-ethyl)-amide oxalate,

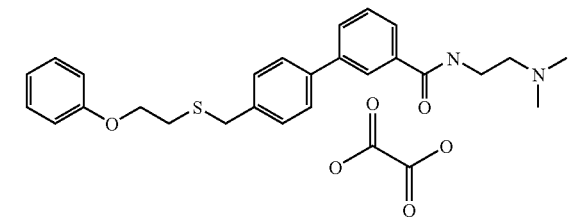

4'-(2-phenoxy-ethylsulfanylmethyl)-biphenyl-3-carboxylic acid (4-dimethylamino-butyl)-amide oxalate,

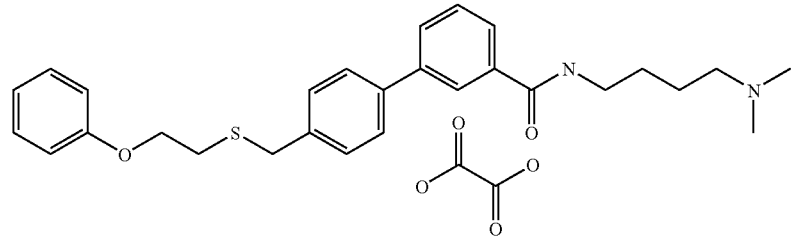

4'-(2-phenoxy-ethylsulfanylmethyl)-biphenyl-4-carboxylic acid (2-dimethylamino-ethyl)-amide oxalate,

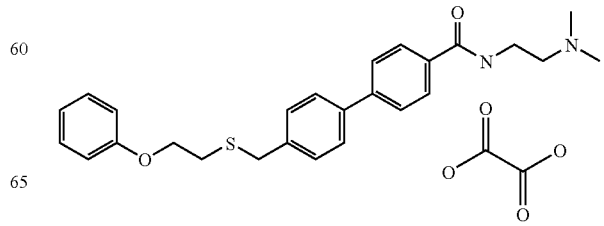

4'-(2-phenoxy-ethylsulfanylmethyl)-biphenyl-4-carboxylic acid (3-dimethylamino-propyl)-amide hydrochloride,

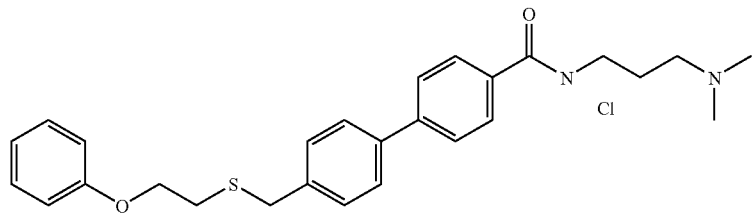

4'-(2-phenoxy-ethylsulfanylmethyl)-biphenyl-4-carboxylic acid (4-dimethylamino-butyl)-amide oxalate,

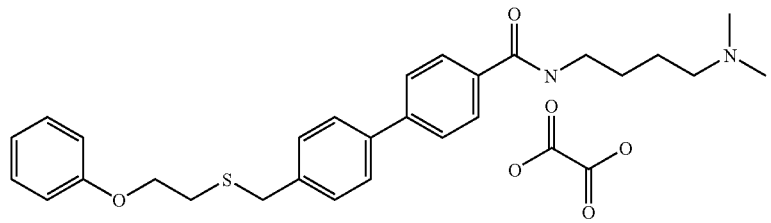

4'-(2-phenoxy-ethylsulfanylmethyl)-biphenyl-2-carboxylic acid (2-dimethylamino-ethyl)-amide oxalate, 4'-(2-phenoxy-ethylsulfanylmethyl)-biphenyl-2-carboxylic acid (3-dimethylamino-propyl)-amide,

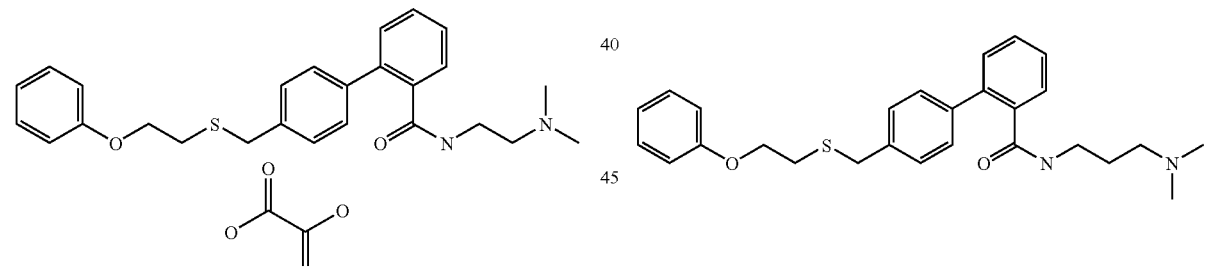

4'-(2-phenoxy-ethylsulfanylmethyl)-biphenyl-2-carboxylic acid (4-dimethylamino-butyl)-amide oxalate,

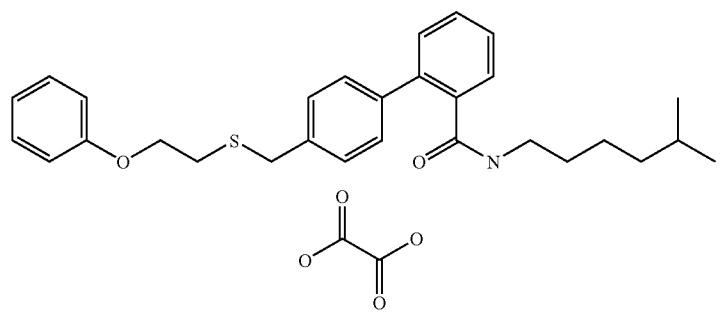

3'-(2-phenoxy-ethylsulfanylmethyl)-biphenyl-2-carboxy-
lic acid (2-dimethylamino-ethyl)-amide hydrochloride,

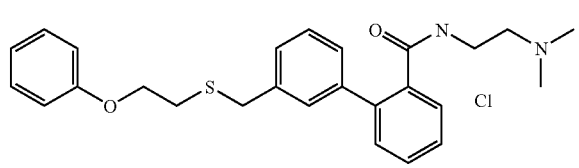

3'-(2-phenoxy-ethylsulfanylmethyl)-biphenyl-2-carboxy-
lic acid (3-dimethylamino-propyl)-amide,

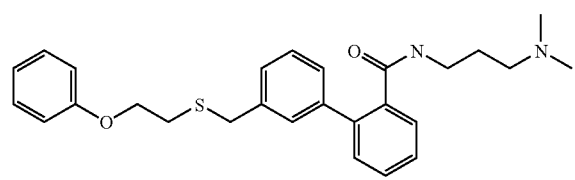

3'-(2-phenoxy-ethylsulfanylmethyl)-biphenyl-2-carboxy-
lic acid (4-dimethylamino-butyl)-amide,

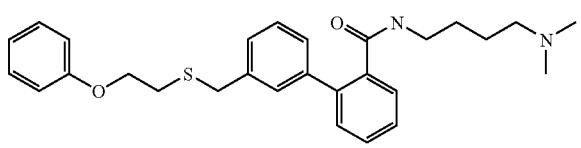

3'-(2-phenoxy-ethylsulfanylmethyl)-biphenyl-3-carboxy-
lic acid (3-dimethylamino-propyl)-amide oxalate,

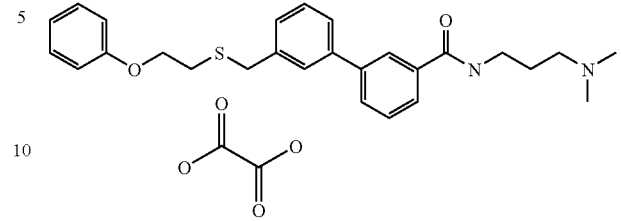

3'-(2-phenoxy-ethylsulfanylmethyl)-biphenyl-4-carboxy-
lic acid (2-dimethylamino-ethyl)-amide,

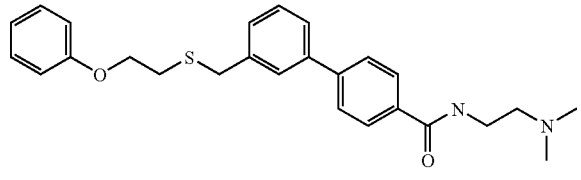

3'-(2-phenoxy-ethylsulfanylmethyl)-biphenyl-4-carboxy-
lic acid (3-dimethylamino-propyl)-amide oxalate,

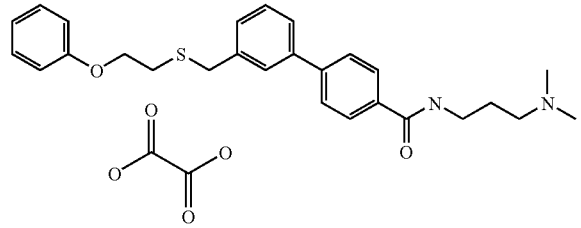

3'-(2-phenoxy-ethylsulfanylmethyl)-biphenyl-4-carboxy-
lic acid (4-dimethylamino-butyl)-amide oxalate,

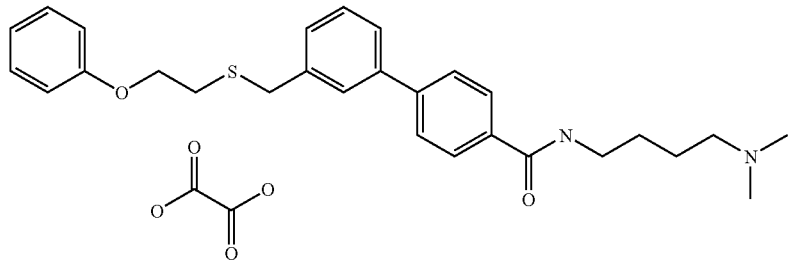

2'-(2-phenoxy-ethylsulfanylmethyl)-biphenyl-2-carboxy-
lic acid (2-dimethylamino-ethyl)-amide oxalate,

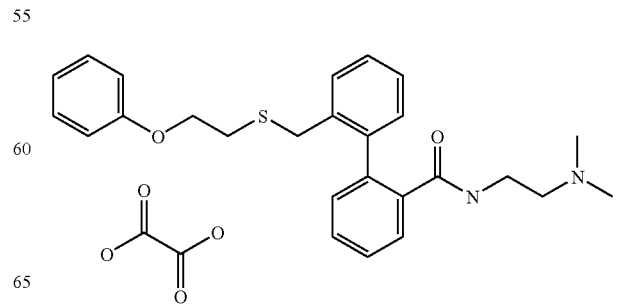

101

2'-(2-phenoxy-ethylsulfanylmethyl)-biphenyl-2-carboxylic acid (3-dimethylamino-propyl)-amide

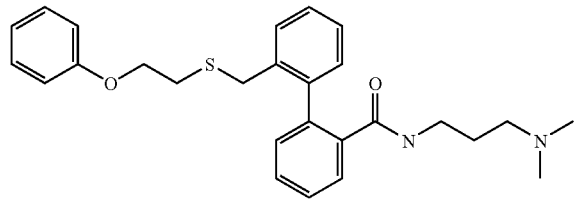

2'-(2-phenoxy-ethylsulfanylmethyl)-biphenyl-2-carboxylic acid (4-dimethylamino-butyl)-amide, oxalate,

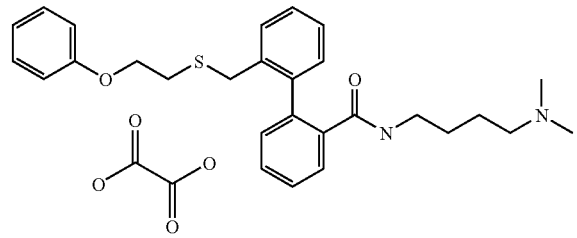

2'-(2-phenoxy-ethylsulfanylmethyl)-biphenyl-3-carboxylic acid (2-dimethylamino-ethyl)-amide oxalate,

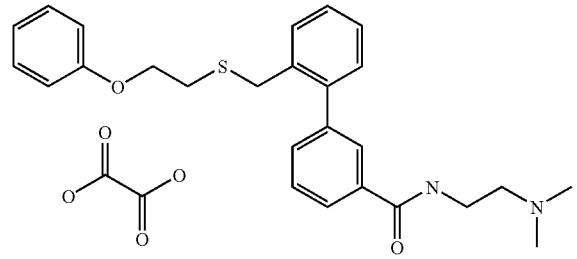

2'-(2-phenoxy-ethylsulfanylmethyl)-biphenyl-3-carboxylic acid (3-dimethylamino-propyl)-amide oxalate,

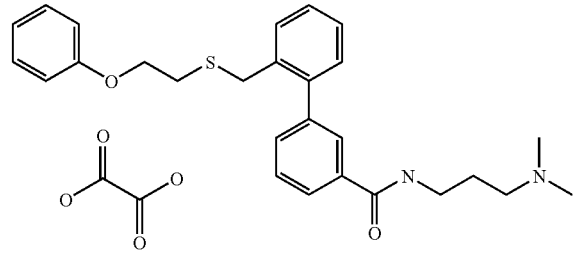

102

2'-(2-phenoxy-ethylsulfanylmethyl)-biphenyl-3-carboxylic acid (4-dimethylamino-butyl)-amide oxalate,

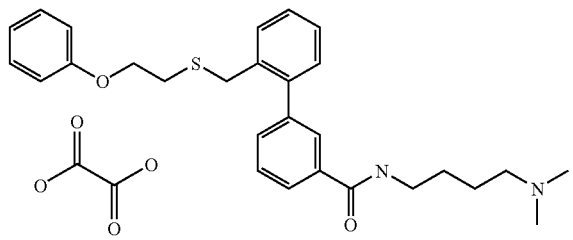

2'-(2-phenoxy-ethylsulfanylmethyl)-biphenyl-4-carboxylic acid (2-dimethylamino-ethyl)-amide,

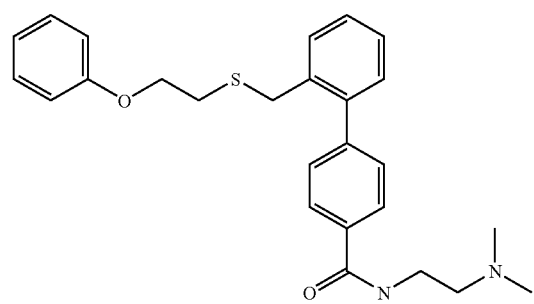

2'-(2-phenoxy-ethylsulfanylmethyl)-biphenyl-4-carboxylic acid (3-dimethylamino-propyl)-amide,

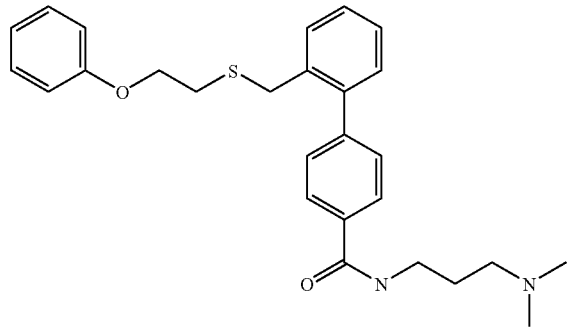

2'-(2-phenoxy-ethylsulfanylmethyl)-biphenyl-4-carboxylic acid (4-dimethylamino-butyl)-amide,

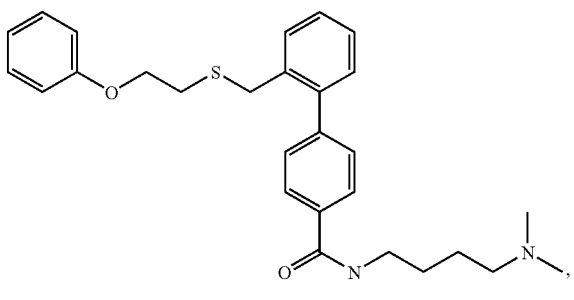

and a pharmaceutically acceptable salt, enatiomer, solvate or prodrug thereof.

5. The compound of claim 1 which is the oxalate salt, the hydrochloride salt, or the bisulfate salt.

6. A method of treating obesity comprising administering to a patient in need thereof a compound of claim 1.

7. A method of treating Type II Diabetes comprising administering to a patient in need thereof a compound of claim 1.

8. A pharmaceutical formulation comprising a compound of claim 1 and a pharmaceutical carrier or diluent.

\* \* \* \* \*